(12) United States Patent
Lahm et al.

(10) Patent No.: US 10,745,696 B2
(45) Date of Patent: Aug. 18, 2020

(54) HC-CDR3-ONLY LIBRARIES WITH REDUCED COMBINATORIAL REDUNDANCY AND OPTIMIZED LOOP LENGTH DISTRIBUTION

(71) Applicant: ITALFARMACO S.P.A., Milan (IT)

(72) Inventors: Armin Lahm, Rome (IT); Christian Steinkuehler, Rome (IT); Gessica Filocamo, Rome (IT)

(73) Assignee: ITALFARMACO S.P.A., Milan (IT)

( * ) Notice: Subject to any disclaimer, the term of this patent is extended or adjusted under 35 U.S.C. 154(b) by 0 days.

(21) Appl. No.: 16/276,557

(22) Filed: Feb. 14, 2019

(65) Prior Publication Data

US 2019/0211326 A1 Jul. 11, 2019

Related U.S. Application Data

(63) Continuation of application No. PCT/EP2017/072315, filed on Jun. 9, 2017.

(30) Foreign Application Priority Data

Sep. 8, 2016 (EP) .................................. 16187884

(51) Int. Cl.
*C40B 40/08* (2006.01)
*C12N 15/10* (2006.01)
*C40B 40/10* (2006.01)
*C07K 16/00* (2006.01)

(52) U.S. Cl.
CPC .......... *C12N 15/1082* (2013.01); *C07K 16/00* (2013.01); *C40B 40/08* (2013.01); *C40B 40/10* (2013.01); *C07K 2317/526* (2013.01)

(58) Field of Classification Search
None
See application file for complete search history.

(56) References Cited

U.S. PATENT DOCUMENTS

2006/0025793 A1 11/2006 Ladner
2011/0082054 A1* 4/2011 Ladner ................ C07K 16/005
506/17

FOREIGN PATENT DOCUMENTS

EP 1979378 A0 10/2008
WO 2008053275 A2 5/2008
(Continued)

OTHER PUBLICATIONS

Carlos F. Barbas III, et al., "Semisynthetic combinatorial antibody libraries: A chemical solution to the diversity problem", Proc. Natl. Acad. Sci. USA, May 1992, vol. 89, pp. 4457-4461.
(Continued)

*Primary Examiner* — Christian C Boesen
(74) *Attorney, Agent, or Firm* — Perkins Coie LLP; Viola Kung

(57) ABSTRACT

The present invention provides for a library of vectors comprising human HC-CDR3 regions of varying length, wherein the diversity of said library is focused on the HC-CDR3 region only and diversity has been optimized such that redundancy is reduced for short HC-CDR3 loops and coverage of HC-CDR3 region variants for longer loop lengths has been increased. The library of the present invention is displayed on phage for selection against target antigens.

7 Claims, 24 Drawing Sheets

Specification includes a Sequence Listing.

(56) References Cited

FOREIGN PATENT DOCUMENTS

| WO | 2009132287 A2 | 10/2009 |
| WO | 2011032181 A2 | 3/2011 |

OTHER PUBLICATIONS

Brandon J Dekosky, et al., "High-throughput sequencing of the paired human immunoglobulin heavy and light chain repertoire" Nature Biotechnology, Jan. 20, 2013, vol. 31, No. 2, pp. 166-171.
Frederic A. Fellouse, et al., "High-throughput Generation of Synthetic Antibodies from Highly Functional Minimalist Phage-displayed Libraries", Journal of Molecular Biology, Aug. 19, 2007, 373, pp. 924-940.
René Michael Hoet, et al., "Generation of high-affinity human antibodies by combining donor-derived and synthetic complementarity-determining-region diversity", Nature Biotechnology, Feb. 20, 2005, vol. 23, No. 3.
E.A. Kabat, et al., "Sequences of Proteins of Immunological Interest", Tabulation and Analysis of Amino Acid and Nucleic Acid Sequences of Precursors, V-regions, C-regions, J-Chain, T-Cell Receptors for Antigen, T-Cell Surface Antigens, β2-Microglobulins, Major Histocompatibility Antigens, Thy-1, Complement, C-Reactive Protein, Thymopoietin, Integrins, Post-gamma Globulin, $\alpha_2$-Macroglobulins, and Other Related Proteins, vol. 1, 5th edition, 1991.
Michael Zemlin, et al., "Expressed Murine and Human CDR-H3 Intervals of Equal Length Exhibit Distinct Repertoires that Differ in their Amino Acid Composition and Predicted Range of Structures", Journal of Molecular Biology, Oct. 7, 2003, 334, pp. 733-749.
Susumu Tonegawa, "Somatic generation of antibody diversity", Nature, Apr. 14, 1983, vol. 302, pp. 575-581.
Michela Silacci, et al., "Design, construction, and characterization of a large synthetic human antibody phage display library", Proteomics, Feb. 8, 2005, 5, pp. 2340-2350.
Josef Prassler, et al., "HuCAL Platinum, a Synthetic Fab Library Optimized for Sequence Diversity and Superior Performance in Mammalian Expression Systems", Journal of Molecular Biology, Aug. 12, 2011, 413, pp. 261-278.
Alessandro Pini, et al., "Design and Use of a Phage Display Library: Human Antibodies with Subnanomolar Affinity Against a Marker of Angiogenesis Eluted From a Two-Dimensional Gel", The Journal of Biological Chemistry, May 25, 1998, vol. 273, No. 34, pp. 21769-21776.
Pascal Philibert, et al., "A focused antibody library for selecting scFvs expressed at high levels in the cytoplasm", BMC Biotechnology, Nov. 22, 2007, 7:81.
Philippe Mondon, et al., "Human antibody libraries: A race to engineer and explore a larger diversity", Frontiers in Bioscience 13, pp. 1117-1129, Jan. 1, 2008.
John McCafferty, et al., "Selection and Rapid Purification of Murine Antibody Fragments That Bind a Transition-State Analog by Phage Display", Applied Biochemistry and Biotechnology, vol. 47, pp. 157-173, May 1994.
Ciara M. Mahon, et al., "Comprehensive Interrogation of a Minimalist Synthetic CDR-H3 Library and Its Ability to Generate Antibodies with Therapeutic Potential", Journal of Molecular Biology, Feb. 19, 2013, 425, pp. 1712-1730.
Cyrus Chothia, et al., "Canonical Structures for the Hypervariable Regions of Immunoglobulins", Journal of Molecular Biology, Apr. 23, 1987, 196, pp. 901-917.
Achim Knappik, et al., "Fully Synthetic Human Combinatorial Antibody Libraries (HuCAL) Based Modular Consensus Frameworks and CDRs Randomized with Trinucleotides", Journal of Molecular Biology, Dec. 6, 1999, 296, pp. 57-86.
Gregory C. Ippolito, et al., "Antibody Repertoires in Humanized NOD-scid-IL2Rynull Mice and Human B Cells Reveals Human-Like Diversification and Tolerance Checkpoints in the Mouse", PLoS One, vol. 7, issue 4, Apr. 27, 2012.
Shu-Cai Huang, et al., "Non-Stochastic Utilization of Ig V Region Genes in Unselected Human Peripheral B Cells", Molecular Immunology, vol. 33, No. 6, pp. 553-560, Dec. 5, 1995.
Larry L. Green, "Transgenic Mouse Strains as Platforms for the Successful Discovery and Development of Human Therapeutic Monoclonal Antibodies", Current Drug Discovery Technologies, Aug. 16, 2013, vol. 11, No. 1, pp. 74-84.
Jacob Glanville, et al., "Precise determination of the diversity of a combinatorial antibody library gives insight into the human immunoglobulin repertoire", PNAS, Dec. 1, 2009, vol. 106, No. 48, pp. 20216-20221.
Stefan Ewert, et al., "Biophysical Properties of Human Antibody Variable Domains", Journal of Molecular Biology, Oct. 28, 2002, 325, pp. 531-553.
Ruud M.T. De Wildt, et al., "Analysis of Heavy and Light Chain Pairings Indicates that Receptor Editing Shapes the Human Antibody Repertoire", Journal of Molecular Biology, Oct. 16, 1998, 285, pp. 895-901.
M. Braunagel, et al., "Construction of a semisynthetic antibody library using trinucleotide oligos", Nucleic Acids Research, Sep. 6, 1997, vol. 25. No. 22, pp. 4690-4691.
International Search Report dated Nov. 3, 2017, issued in PCT/EP2017/072315.

* cited by examiner

Figure 5

| Trimer-block | Amino acid | |
|---|---|---|
| GCT | Ala | A |
| GAC | Asp | D |
| GAA | Glu | E |
| TTC | Phe | F |
| GGT | Gly | G |
| CAT | His | H |
| ATA | Ile | I |
| AAA | Lys | K |
| CTG | Leu | L |
| ATG | Met | M |
| AAC | Asn | N |
| CCG | Pro | P |
| CAG | Gln | Q |
| CGT | Arg | R |
| TCT | Ser | S |
| ACT | Thr | T |
| GTT | Val | V |
| TGG | Trp | W |
| TAC | Tyr | Y |

Figure 8

| Antibody | | CDR3H | | CDR3H length |
|---|---|---|---|---|
| Crenezumab MABT-5102A CHEMBL1743004 | CAS | G..............D | WGQG | 3 |
| Nivolumab BMS-936558 CHEMBL2108738 | CAT | ND.............D | WGQG | 4 |
| Atinumab CHEMBL1742987 | CAT | EL.............FD | WGQG | 5 |
| Dacetuzumab CHEMBL1743005 | CAR | EG.............IY | WGRG | 5 |
| Ensituximab CHEMBL1743013 | CVK | PG.............GD | WGQG | 5 |
| Satumomab pendetide CHEMBL1743091 | CKR | SY.............YG | WGRG | 5 |
| Briakinumab CHEMBL1742995 | CKT | RGS............HL | RGQG | 6 |
| Lampalizumab Anti-Factor-D CHEMBL2109408 | CER | EGG............VN | WGQG | 6 |
| Ozoralizumab CHEMBL1743054 | CAR | SPS............GF | WGQG | 6 |
| Brodalumab CHEMBL1742996 | CAR | RQL............YFD | WGQG | 7 |
| Citatuzumab bogatox CHEMBL1743000 | CAQ | NLE............IPR | FGQG | 7 |
| Daclizumab Ro-247375 CHEMBL1201605 | CAR | GGG............VFD | WGQG | 7 |
| Oportuzumab monatox CHEMBL1743052 | CAQ | NLE............IPR | FGQG | 7 |
| Ponezumab PF-04360365 CHEMBL1743058 | CAS | LYS............LPV | WGQG | 7 |
| Radretumab CHEMBL1743060 | CAR | PFP............YFD | WGQG | 7 |
| Ramucirumab CHEMBL1743062 | CAR | VTD............AFD | WGQG | 7 |
| Sarilumab SAR-153191 CHEMBL2108730 | CAK | GRD............SFD | WGQG | 7 |
| Sifalimumab CHEMBL1743069 | CAR | DPI............AAG | WGQG | 7 |
| Simtuzumab CHEMBL2109667 | CAR | NWM............NFD | WGQG | 7 |
| Alacizumab Pegol CHEMBL1742983 | CVR | IGED...........ALD | WGQG | 8 |
| Basiliximab Simulect CHEMBL1201439 | CSR | DYGY...........YFD | WGQG | 8 |
| Brentuximab Vedotin CHEMBL1742994 | CAR | YGNY...........NFA | WGQG | 8 |
| Dalotuzumab CHEMBL1743006 | CAR | WGRV...........FFD | WGQG | 8 |
| Enavatuzumab CHEMBL1743011 | CTS | YYAD...........AMD | WGQG | 8 |
| Etaracizumab Etaratuzumab CHEMBL1743014 | CAR | HLRG...........SFA | WGQG | 8 |
| Panobacumab CHEMBL1743055 | CAR | DRYY...........GPE | WGQG | 8 |
| Quilizumab Anti-M1 Prime CHEMBL2109456 | CAR | DRWD...........AMD | WGQG | 8 |
| Rontalizumab RhuMAb IFNalpha CHEMBL1743066 | CAS | WISD...........FFD | WGQE | 8 |
| Samalizumab CHEMBL1743067 | CGR | SKRD...........YFD | WGQG | 8 |

Figure 8 continued

| Antibody | | CDR3H | | CDR3H length |
|---|---|---|---|---|
| Alirocumab CHEMBL2109540 | CAK | DSNW.........GNFD | WGRG | 9 |
| Blosozumab LY-2541546 CHEMBL1742993 | CAT | GDTT.........YKFD | WGQG | 9 |
| Canakinumab ACZ-885 L04AC08 CHEMBL1201834 | CAR | DLRT.........GPFD | WGQG | 9 |
| Etrolizumab rhuMAb beta7 Anti-Beta7 Pro145223 CHEMBL1743015 | CAR | TGSS.........GYFD | WGQG | 9 |
| Ficlatuzumab CHEMBL1743018 | CAR | NYVG.........SIFD | WGQG | 9 |
| Foralumab CHEMBL1743020 | CAR | QMGY.........WHFD | WGRG | 9 |
| Glembatumumab vedotin CHEMBL1743028 | CAR | GYNW.........NYFD | WGQG | 9 |
| Lorvotuzumab Mertansine CHEMBL1743037 | CAR | MRKG.........YAMD | WGQG | 9 |
| Olokizumab CHEMBL1743050 | CAR | ESYY.........SFTS | WGQG | 9 |
| Pateclizumab CHEMBL1743056 | CSR | PIWL.........PWFA | WGQG | 9 |
| Patritumab CHEMBL2109406 | CAR | DKWT.........WYFD | WGRG | 9 |
| Suvizumab CHEMBL1743074 | CSR | GIPG.........YAMD | WGQG | 9 |
| Teprotumumab Ro-4858696-000 CHEMBL1743079 | CAR | ELGR.........RYFD | WGRG | 9 |
| Ublituxumab CHEMBL1743084 | CAR | YDYN.........YAMD | WGQG | 9 |
| Vorsetuzumab Mafodotin CHEMBL2108672 | CAR | DYGD.........YGMD | WGQG | 9 |
| Muromonab-Cd3 L04AA02 CHEMBL1201608 | CAR | YYDD.........HYCLD | WGQG | 10 |
| Abagovomab CHEMBL1742981 | CAR | GEGN.........YAWFA | WGQG | 10 |
| Abciximab B01AC13 ReoPro CHEMBL1201584 | CVR | PLYD.........YYAMD | WGQG | 10 |
| Afutuzumab Ro-5072759 HUMAB CHEMBL1743048 | CAR | NVFD.........GYWLV | WGQG | 10 |
| Alemtuzumab Campath-1H L01XC04 CHEMBL1201587 | CAR | EGHT.........AAPFD | WGQG | 10 |
| Amatuximab CHEMBL1742984 | CAR | GGYD.........GRGFD | WGSG | 10 |
| Anrukinzumab CHEMBL1742985 | CAR | LDGY.........YFGFA | WGQG | 10 |
| Arcitumomab CHEMBL1743090 | CTR | DRGL.........RFYFD | WGQG | 10 |
| Bezlotoxumab CHEMBL2108670 | CAR | RRNW.........GNAFD | WGQG | 10 |
| Cantuzumab mertansine CHEMBL1742997 | CAR | RGPY.........NWYFD | WGQG | 10 |
| Carlumab CHEMBL1742999 | CAR | YDGI.........YGLD | WGQG | 10 |
| Clivatuzumab tetraxetan CHEMBL1743002 | CAR | GFGG.........SYGFA | WGQG | 10 |
| Demcizumab CHEMBL2109384 | CAR | DYDY.........DVGMD | WGQG | 10 |
| Elotuzumab CHEMBL1743010 | CAR | PDGN.........YWYFD | WGQG | 10 |
| Farletuzumab CHEMBL1743016 | CAR | HGDD.........PAWFA | WGQG | 10 |

Figure 8 continued

| Antibody | | CDR3H | | CDR3H length |
|---|---|---|---|---|
| Fasinumab SAR-154877 CHEMBL2109528 | CST | IFGV........VTNFD | WGQG | 10 |
| Flanvotumab CHEMBL2108734 | CAP | RYSS........SWYLD | WGQG | 10 |
| Foravirumab CHEMBL1743021 | CAK | VAVA........GTHFD | WGQG | 10 |
| Gevokizumab CHEMBL1743026 | CAR | NKYD........PPWFV | WGQG | 10 |
| Girentuximab CA9-SCAN CG250 CHEMBL1743027 | CAR | HRSG........YFSMD | WGQG | 10 |
| Intetumumab CHEMBL1743032 | CAR | EARG........SYAFD | WGQG | 10 |
| Italizumab CHEMBL1743033 | CAR | RDYD........LDYFD | WGQG | 10 |
| Ixekizumab LY-2439821 CHEMBL1743034 | CAR | YDYF........TGTGV | WGQG | 10 |
| Lebrikizumab PRO-301444 RG-3637 CHEMBL1743035 | CAG | DGYY........PYAMD | WGQG | 10 |
| Mogamulizumab CHEMBL1743041 | CGR | HSDG........NFAFG | WGQG | 10 |
| Motavizumab CHEMBL1743042 | CAR | DMIF........NFYFD | WGQG | 10 |
| Namilumab CHEMBL1743044 | CTR | TTLI........SVYFD | WGQG | 10 |
| Onartuzumab CHEMBL1743051 | CAT | YRSY........VTPLD | WGQG | 10 |
| Otelixizumab CHEMBL1743053 | CAR | FRQY........SGSFD | WGQG | 10 |
| Robatumumab CHEMBL1743064 | CAR | LGNF........YYGMD | WGQG | 10 |
| Siltuximab CHEMBL1743070 | CAR | GLWG........YYALD | WGQG | 10 |
| Sirukumab CHEMBL1743071 | CAR | QLWG........YYALD | WGQG | 10 |
| Solitomab CHEMBL2109264 | CAR | LRWW........DPMD | WGQG | 10 |
| Tadocizumab CHEMBL1743076 | CAR | RDGN........YGWFA | WGQG | 10 |
| Tigatuzumab CHEMBL1743080 | CAR | RGDS........MITTD | WGQG | 10 |
| Zatuximab HC Zatuximab CHEMBL2109395 | CVR | YYGY........DEAMD | WGQG | 10 |
| Bavituximab CHEMBL1742989 | CVK | GGYYG........HWYFD | WGAG | 11 |
| Cetuximab IMC-C225 L01XC06 CHEMBL1201577 | CAR | ALTYY........DYEFA | WGQG | 11 |
| Efungumab MYC-123A MYC-123B MYC-124 HSP90MAB CHEMBL1743009 | CAR | GGRDF........GDSFD | WGQG | 11 |
| Fresolimumab CHEMBL1743022 | CAS | TLGLV........LDAMD | WGQG | 11 |
| IMGATUZUMAB HC GA201 RG-7160 Ro-5083945 HuMAB CHEMBL210939 | CAR | LSPGG........YYVMD | WGQG | 11 |
| Lucatumumab CHEMBL1743038 | CAR | DGIA........APGFD | WGQG | 11 |
| Mavrilimumab CHEMBL1743039 | CAI | VGSFS........PLTLG | WGQG | 11 |
| Milatuzumab CHEMBL1743040 | CSR | SRGKN........EAWFA | WGQG | 11 |
| Naptumomab Estafenatox CHEMBL1743045 | CAR | SIRIT........NYVMD | WGQG | 11 |
| Necitumumab CHEMBL1743047 | CAR | VSIFG........VGTFD | WGQG | 11 |
| Tenatumomab CHEMBL1743077 | CAR | GGGSI........YYAMD | WGQG | 11 |
| Trastuzumab L01XC03 CHEMBL1201585; | CSR | WGGDG........FYAMD | WGQG | 11 |
| Vatelizumab CHEMBL1743086 | CAR | ANDGV........YYAMD | WGQG | 11 |

Figure 8 continued

| Antibody | | CDR3H | | CDR3H length |
|---|---|---|---|---|
| Benralizumab CHEMBL1742991 | CGR | EGIRY.......YGLLGD | WGQG | 12 |
| Clazakizumab CHEMBL2108589 | CAR | DDSSD.......WDAKFN | WGQG | 12 |
| Conatumumab CHEMBL1743003 | CAR | DRGGD.......YYYGMD | WGQG | 12 |
| Drozitumab Anti-Dr5 Rhumab-Dr5 CHEMBL1743008 | CAR | ILGAG.......RGWYFD | WGKG | 12 |
| Duligotumab CHEMBL2109405 | CAR | ESRVS.......FEAAMD | WGQG | 12 |
| Fezakinumab CHEMBL1743017 | CAR | EFEKF.......DSDDSD | WGRG | 12 |
| Veltuzumab CHEMBL1743088 | CAR | STYYG.......GDRQFD | WGKG | 12 |
| Omalizumab RG-3648 CHEMBL1201589 | CAR | GSHYF.......GHWEFA | WGQG | 12 |
| Orticumab CHEMBL2109533 | CAR | IRVGP.......SGGAFI | WGQG | 12 |
| Racotumomab CHEMBL1743059 | CAR | EDYYD.......NSYYFD | WGQG | 12 |
| Rilotumumab CHEMBL1743063 | CAR | GGYDF.......WSGYFD | WGQG | 12 |
| Rituximab Rituxan RG-105 L01XC02 R-105 IDEC-102 CHEMBL1201576 | CAR | STYYG.......GDWYFD | WGAG | 12 |
| Vedolizumab CHEMBL1743087 | CAR | GGYDS.......WDYAID | WGQG | 12 |
| Veltuzumab CHEMBL1743088 | CAR | STYYG.......GDRYFD | WGQG | 12 |
| Daratumumab CHEMBL1743007 | CAR | DKILN......FGEPVFD | WGQG | 13 |
| Enokizumab CHEMBL1743012 | CAR | ADYYG......SDYVKFD | WGQG | 13 |
| Ibalizumab CHEMBL1743029 | CAR | EKDNY......ATGAWFA | WGQG | 13 |
| Indatuximab Ravtansine CHEMBL1743031 | CAR | RDYYG......NFYYAMD | WGQG | 13 |
| Narnatumab RON8 CHEMBL1743046 | CTR | DGYSS......GRHYGMD | WGQG | 13 |
| Perakizumab CHEMBL2109470 | CAR | DSDYG......SSYGAMD | WGQG | 13 |
| Ibritumomab tiuxetan CHEMBL1201606 | CAR | VVYYS......NSYWYFD | WGTG | 13 |
| Tralokinumab CHEMBL1743081 | CAR | DSSSS......WARWFFD | WGRG | 13 |
| Tregalizumab CHEMBL1743083 | CSA | SYYRY......DVGARFA | WGQG | 13 |
| Urelumab BMS-663513 CHEMBL1743085 | CAR | DYGPG......NYDWYFD | WGRG | 13 |
| Bevacizumab L01XC07 Rhumab- 12-IGG1 CHEMBL1201583 | CAR | YPHYG.....SSHRYFD | WGQG | 14 |
| Enoticumab CHEMBL2109385 | CAR | DHDFRS.....GYEGWFD | WGQG | 14 |
| Fulranumab JNJ-42160443 CHEMBL1743023 | CAR | VYSSGW.....HVSDYFD | WGQG | 14 |
| Futuximab CHEMBL2109388 | CTR | NGDYYV.....SSGDAMD | WGQG | 14 |
| Ligelizumab CHEMBL2109457 | CAR | FSHFSG.....SNYDYFD | WGQG | 14 |
| Lirilumab BMS-986015 BMS-986015-01 Anti-KIR Antibody CHEMBL2109 | CAR | IPSGSY.....YYDYDMD | WGQG | 14 |
| Moxetumomab Pasudotox CHEMBL1743043 | CAR | RSGYGT.....HWGVLFA | WGQG | 14 |
| Parsatuzumab CHEMBL2109387 | CAR | EGVYRD.....YDDYAMD | WGQG | 14 |
| Romosozumab CHEMBL2107874 | CAR | LGYDDI.....YDDRYFD | WGQG | 14 |
| Vesencumab CHEMBL1743089 | CAR | GELPYY.....RMSKVMD | WGQG | 14 |

Figure 8 continued

| Antibody | | CDR3H | | CDR3H length |
|---|---|---|---|---|
| Blinatumomab CHEMBL1742992 | CAR | RETTTV....GRYYYAMD | WGQG | 15 |
| Tabalumab LY-2127399 CHEMBL1743075 | CAR | GYYDIL....TGYYYYFD | WGQG | 15 |
| Figitumumab CHEMBL1743019 | CAK | DLGWSDS...YYYYYGMD | WGQG | 16 |
| Inclacumab LC1004-002 Ro-4905417 CHEMBL2109488 | CAR | GRYSGSS...SYYNDWFD | WGQG | 16 |
| Gantenerumab CHEMBL1743025 | CAR | GKGNTHK.P.YGYVRYFD | WGQG | 17 |
| Icrucumab CHEMBL1743030 | CAR | DRYGSGY.HHYFYYGLDV | WGQG | 17 |
| Olaratumab CHEMBL1743049 | CAR | QSTYYYG.S.GNYYGWFD | WGQG | 17 |
| Roledumab CHEMBL1743065 | CAR | PVRSRWL.Q.LGLEDAFD | WGQG | 17 |
| Rafivirumab CR-57 CHEMBL1743061 | CAR | ENLDNSG.YTYYFSGWFD | WGQG | 18 |
| Secukinumab AIN457 AIN-457 L04AC10 CHEMBL1743068 | CVR | DYYDILT.YDYIHYWYFD | WGRG | 18 |
| Caplacizumab CHEMBL2109624 | CAA | AGVRAEDGVRRTLPSEYT | WGQG | 19 |

Figure 11

| Pos | Type | Amino acid composition | 5' end | | | | | | | |
|---|---|---|---|---|---|---|---|---|---|---|
| | fixed | | G | | | | | | | |
| | fixed | | C | | | | | | | |
| | fixed | | A | | | | | | | |
| | fixed | | C | | | | | | | |
| | fixed | | T | | | | | | | |
| | fixed | | T | | | | | | | |
| 88 | fixed | Ala 100% | G | PstI | | | | | | |
| | fixed | | C | | | | | | | |
| | fixed | | A | | | | | | | |
| 89 | fixed | Val 100% | G | | | | | | | |
| | fixed | | T | | | | | | | |
| | fixed | | G | | | | | | | |
| 90 | fixed | Tyr 100% | T | | | | | | | |
| | fixed | | A | | | | | | | |
| | fixed | | T | | | | | | | |
| 91 | fixed | Tyr 100% | T | | | | | | | |
| | fixed | | A | | | | | | | |
| | fixed | | C | | | | | | | |
| 92 | fixed | Cys 100% | T | | | | | | | |
| | fixed | | G | | | | | | | |
| | fixed | | C | | | | | | | |
| 93 | fixed | Ala 100% | G | | | | | | | |
| | fixed | | C | | | | | | | |
| | fixed | | T | | | | | | | |
| 94 | fixed | Arg 100% | C | | | | | | | |
| | fixed | | G | | | | | | | |
| | fixed | | T | | | | | | | |
| 95 | degenerate | Asp 54.1%, Gly 45.9% | GAC 54.1% | GGT 45.9% | | | | | | |
| 96 | degenerate | Gly 20.8%, Arg 19.6%, Pro 14.2%, Leu 12.1%, Ser 10.9%, Val 7.6%, Tyr 7.5%, Ala 7.3% | GGT 20.8% | CGT 19.6% | CCG 14.2% | CTG 12.1% | TCT 10.9% | GTT 7.6% | TAC 7.5% | GCT 7.3% |
| 97 | degenerate | Gly 23.7%, Tyr 17.2%, Arg 13.7%, Ser 12.6%, Val 9.0%, Leu 8.1%, Pro 7.9%, Asp 7.8% | GGT 23.7% | TAC 17.2% | CGT 13.7% | TCT 12.6% | GTT 9.0% | CTG 8.1% | CCG 7.9% | GAC 7.8% |
| 98 | degenerate | Tyr 19.4%, Gly 17.9%, Ser 17.2%, Asp 10.6%, Val 9.9%, Arg 9.0%, Ala 8.5%, Thr 7.5% | TAC 19.4% | GGT 17.9% | TCT 17.2% | GAC 10.6% | GTT 9.9% | CGT 9.0% | GCT 8.5% | ACT 7.5% |

Figure 11 continued

| | | | | | | | | | | |
|---|---|---|---|---|---|---|---|---|---|---|
| 99 | degenerate | Gly 21.0%, Ser 19.9%, Tyr 17.7%, Val 9.6%, Ala 9.5%, Asp 8.5%, Arg 7.0%, Leu 6.8% | GGT 21.0% | TCT 19.9% | TAC 17.7% | GTT 9.6% | GCT 9.5% | GAC 8.5% | CGT 7.0% | CTG 6.8% |
| 100 | degenerate | Gly 22.2%, Ser 21.4%, Tyr 15.1%, Val 10.0%, Ala 9.2%, Asp 8.3%, Thr 6.9%, Leu 6.8% | GGT 22.2% | TCT 21.4% | TAC 15.1% | GTT 10.0% | GCT 9.2% | GAC 8.3% | ACT 6.9% | CTG 6.8% |
| 100A | degenerate | Ser 23.4%, Gly 21.6%, Tyr 14.9%, Val 8.8%, Thr 8.6%, Ala 8.4%, Asp 7.6%, Leu 6.7% | TCT 23.4% | GGT 21.6% | TAC 14.9% | GTT 8.8% | ACT 8.6% | GCT 8.4% | GAC 7.6% | CTG 6.7% |
| 100B | degenerate | Gly 23.3%, Tyr 21.3%, Ser 19.2%, Thr 7.7%, Ala 7.7%, Val 7.2%, Asp 6.9%, Leu 6.5% | GGT 23.3% | TAC 21.3% | TCT 19.2% | ACT 7.7% | GCT 7.7% | GTT 7.2% | GAC 6.9% | CTG 6.5% |
| 100C | degenerate | Tyr 28.4%, Gly 19.3%, Ser 15.7%, Arg 8.0%, Ala 7.5%, Pro 7.3%, Thr 6.9%, Leu 6.8% | TAC 28.4% | GGT 19.3% | TCT 15.7% | CGT 8.0 | GCT 7.5% | CCG 7.3% | ACT 6.9% | CTG 6.8% |
| 100D | degenerate | Tyr 34.3%, Gly 15.5%, Ser 14.0%, Leu 8.4%, Pro 8.3%, Thr 8.8%, Arg 6.7%, Ala 6.8% | TAC 34.3% | GGT 15.5% | TCT 14.0% | CTG 8.4% | CCG 8.3% | ACT 6.8% | CGT 6.7% | GCT 6.8% |
| 100E | degenerate | Tyr 35.1%, Gly 16.9%, Asp 11.9%, Asn 11.9%, Ser 8.3%, Trp 6.0%, Arg 5.2%, Pro 4.6% | TAC 35.1% | GGT 16.9% | GAC 11.9% | AAC 11.9% | TCT 8.3% | TGG 6.0% | CGT 5.2% | CCG 4.6% |
| 100F | degenerate | Gly 27.3%, Tyr 23.5%, Trp 16.5%, Ala 16.4%, Pro 8.4%, Ser 4.0%, Leu 3.5%, Thr 2.4% | GGT 27.3% | TAC 23.5% | TGG 16.5% | GCT 16.4% | CCG 8.4% | TCT 4.0% | CTG 3.5% | ACT 2.4% |
| 100G | fixed | Phe 100% | T | | | | | | | |
| | fixed | | T | | | | | | | |
| | fixed | | C | | | | | | | |
| 101 | fixed | Asp 100% | G | | | | | | | |
| | fixed | | A | | | | | | | |
| | fixed | | C | | | | | | | |
| 102 | fixed | Tyr 100% | T | | | | | | | |
| | fixed | | A | | | | | | | |
| | fixed | | C | | | | | | | |
| 103 | fixed | Trp 100% | T | | | | | | | |
| | fixed | | G | | | | | | | |
| | fixed | | G | | | | | | | |
| 104 | fixed | Gly 100% | G | | | | | | | |
| | fixed | | G | | | | | | | |
| | fixed | | C | | | | | | | |
| 105 | fixed | Gln 100% | C | | | | | | | |
| | fixed | | A | StyI | | | | | | |
| | fixed | | A | | | | | | | |
| 106 | fixed | Gly 100% | G | | | | | | | |
| | fixed | | G | | | | | | | |
| | fixed | | T | | | | | | | |
| | fixed | | C | | | | | | | |
| | fixed | | G | | | | | | | |
| | fixed | | G | | | | | | | |

3' end

Figure 14 continued
Fig. 14C
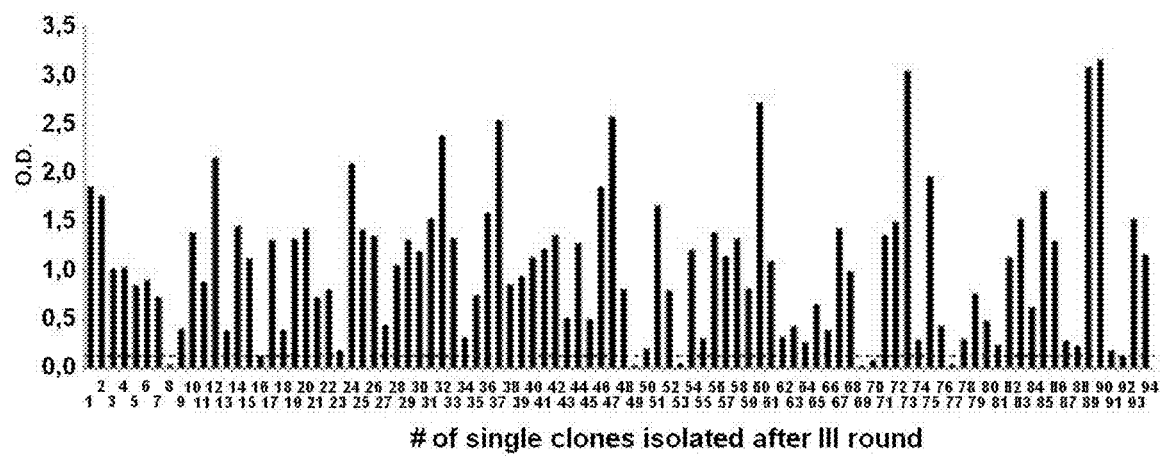
Fig. 14D
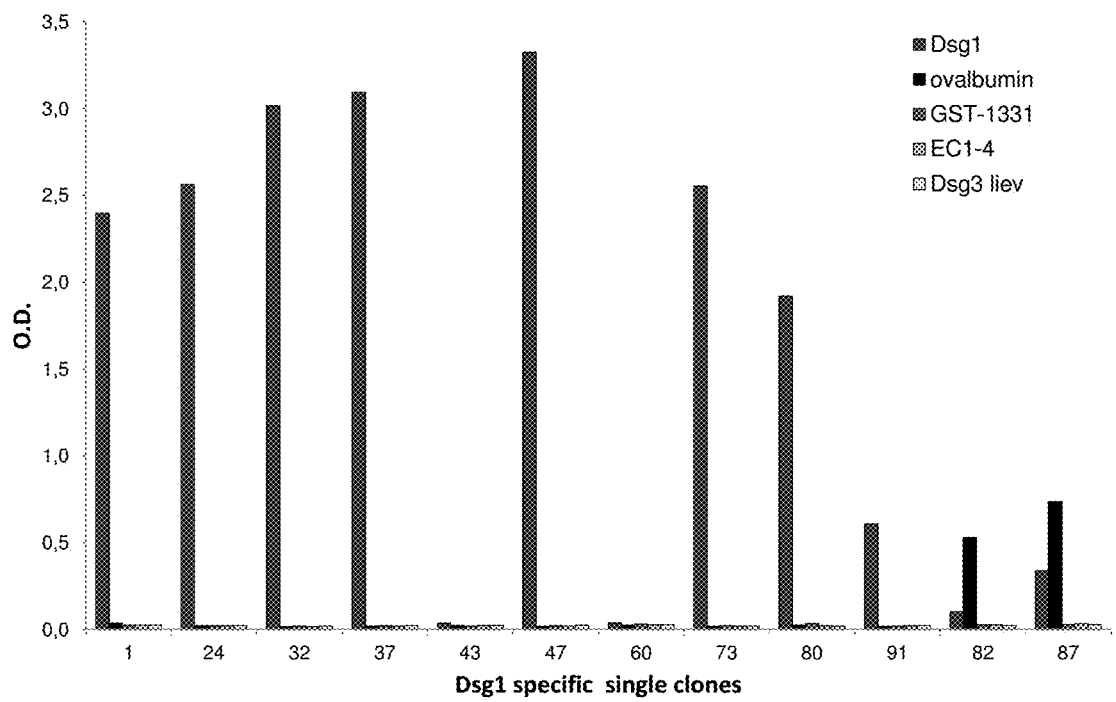

HC-CDR3-ONLY LIBRARIES WITH REDUCED COMBINATORIAL REDUNDANCY AND OPTIMIZED LOOP LENGTH DISTRIBUTION

This application is a continuation of PCT/EP2017/072315, filed Sep. 6, 2017; which claims the priority of EP 16187884.8, filed Sep. 8, 2016. The contents of the above-identified applications are incorporated herein by reference in their entireties.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Feb. 6, 2019, and a size of 45.0 kilobytes. The Sequence Listing filed via EFS-Web is part of the specification and is hereby incorporated in its entirety by reference herein.

FIELD OF THE INVENTION

The present invention provides for a library of vectors comprising human HC-CDR3 regions of varying length, wherein the diversity of said library is focused on the HC-CDR3 region only and diversity has been optimized such that redundancy is reduced for short HC-CDR3 loops and coverage of HC-CDR3 region variants for longer loop lengths has been increased. The library of the present invention is displayed on phage for selection against target antigens.

BACKGROUND OF THE INVENTION

Despite the recent development of in vivo discovery platforms providing fully human antibodies (Green, 2014), recombinant antibody libraries continue to represent an important complementary approach, in particular for difficult targets where in vivo attempts have failed or are impossible to conduct due to the nature of the antigen. Recombinant antibody libraries have been described in a variety of layouts and formats (Mondon et al., 2008). Libraries are usually constructed in a combinatorial fashion randomly combining successively more complex variation within up to six loop regions, the complement determining regions (CDRs). The largest variation is generally introduced in the CDR3 region of the heavy chain (HC) variable domain (HC-CDR3), the most variable and important CDR segment present in natural antibodies (Tonegawa, 1983; Chothia et al., 1989).

For the HC-CDR3 regions the loop length distribution (percentage of each loop length present in the library) implemented in recombinant antibody libraries normally mirrors that observed in natural antibodies, that is a distribution showing an approximately bell-shaped distribution with a maximum around HC-CDR3 loops of length 12 (Zemlin et al., 2003). With few exceptions (for example Fellouse et al, 2007; Mahon et al., 2013), recombinant antibody libraries have been designed to follow (approximately) this bell-shaped distribution. This has important consequences when a library of high complexity ($10^9$ to $10^{10}$ total complexity or higher) is generated in a combinatorial fashion. Variants from shorter HC-CDR3 loops will be over-represented (practically all variants are present or even present several times) relative to variants from long HC-CDR3 loops because for the latter only a tiny fraction of all possible variants is present. Using a constant length distribution for the HC-CDR3 loop length (all HC-CDR3 lengths are present with an equal proportion in the library) further increases the redundancy for the shorter HC-CDR3 loops (their percent fraction is higher as compared to the bell-shaped distribution observed for natural antibodies), marginally increases the total coverage of possible variants for long HC-CDR3 loops and reduces the coverage for mid-range length HC-CDR3 loops.

The total number of antibodies already approved as therapeutic agents or in clinical development is steadily increasing. A survey of the ChEMBL database (www.ebi.ac.uk/chembl/) shows that their HC-CDR3 length distribution has a pronounced maximum at HC-CDR3 length 10, different from the smooth bell-shaped length distribution observed for natural human antibodies but also that from mouse antibodies. HC-CDR3 loops of length 10 should therefore be represented particularly well in a library aimed at isolation of candidates for therapeutic antibodies. It is likely that antibodies with shorter HC-CDR3 loops express well and show lower tendency for aggregation, important characteristics for a successful product development.

Although HC-CDR3-only libraries have been generated in various contexts (Barbas et al., 1992; Braunagel et al., 1997; Pini et al., 1998; Hoet et al., 2005; Silacci et al., 2005; Mahon et al., 2013; US 2006/0257937A1) many recombinant antibody libraries introduce diversity not only in the HC-CDR3 region but also in one or more of the five other CDR regions (for example Knappik et al., 2000; Prassler et al., 2013) The diversity present in the various CDR regions is then combined, in a completely random fashion, during library cloning usually starting with the CDR region with the lowest overall diversity. With the exception of short HC-CDR3 loops, where some redundancy can exist and duplicates might be present, each HC-CDR3 region variant has to be considered unique being present only once in the library. As a consequence, each HC-CDR3 loop variant becomes "associated" with a completely random combination of variants from the other CDR regions, without any structural or functional selection for compatibility. Compared to a situation where the other CDR regions are represented by germline sequences or by single consensus sequences (for example for the light chain CDR3 region), there is no advantage having a particular HC-CDR3 variant combined with a random selection of variants from the other (one to five) CDR regions. A HC-CDR3-only library should therefore perform as good or even better compared to a library with additional diversity. The only exception is short HC-CDR3 loops where, due to the redundancy (presence of variants in more than one copy in the library), a very limited number of combinations of variation in the other CDRs can be explored, i.e. the same HC-CDR3 variant would be present multiple times, each time with a different combination of variants in the other CDR regions. However, in order for the HC-CDR3 variant to be combined with only 10 of these combinations, the duplication level of the HC-CDR3 region must also be around 10. Even for short HC-CDR3 loops this would imply to increase the fraction of that loop length in the library by a factor of 10, being impractical for most HC-CDR3 loop lengths. For example, a HC-CDR3 loop with a particular length that represents a few percent of the total library would need to be present at a relatively high double-digit percent fraction in order to effectively explore additional diversity present in the library, for example in LC-CDR3. While this is already difficult to achieve for a single HC-CDR3 loop length, it is impossible to generate a library where variants from all HC-CDR3 loop lengths effectively combine with even a limited number of variants in another CDR region. In one case (Mahon et al., 2013) the performance a HC-CDR3-only library was compared to a corresponding HC-CDR3-and-LC-CDR3 library. The HC-CDR3-only library showed superior properties; however the authors did not fully appreciate the "combinatorial effect" that favors a HC-CDR3-only library but attributed the better performance of the HC-CDR3 library to possible structural incompatibilities between the LC-CDR3 and HC-CDR3 diversity in the HC-CDR3-and-LC-CDR3 library.

Recombinant antibody libraries where the design of the HC-CDR3 diversity is based on the position-wise amino acid frequencies observed in natural antibodies have been generated using either standard degenerated oligonucleotides (e.g. Philibert et al., 2007), allowing only an approximate representation of the desired amino acid distribution and generating undesired Cys and stop codons, or by oligonucleotides where diversity has been introduced through mixtures of trimer-blocks encoding amino acids (Braunagel et al., 1997; Knappik et al., 2000; Prassler et al, 2013, Mahon et al, 2013; patent applications US 2006/0257937A1, EP1979378B1).

However, none of these examples appreciates the combinatorial effect that relates to the number of different variants that are actually present in the library for a particular HC-CDR3 length representing a certain fraction of the total library compared to the theoretically possible number of variants as defined by the library design. In the presence of a bell-shaped "natural-like" HC-CDR3 loop length distribution, the combinatorial effect leads to an over-representation of variants for short HC-CDR3 loops and a very small coverage for longer HC-CDR3 loops. US 2006/0257937A1 only describes library designs that cover a restricted range of HC-CDR3 loop lengths (8, 10, 13, 14, 15, 17, 18, 19) and the amino acid composition at the HC-CDR3 loop positions either corresponds to a fixed equimolar mixture of 19 different amino acids or is restricted to a fixed mixture of few amino acids for a particular position, indiscriminately for all HC-CDR3 loop lengths. EP1979378B1 describes a library design where the HC-CDR3 loop lengths are divided into three varying length ranges, each range having a defined amino acid composition (called diversity factor). The diversity factor representing the amino acid composition of all HC-CDR3 loops within a certain length range for the various HC-CDR3 loop positions comprises Kabat positions 95 to 102. For each position or range of positions within HC-CDR3 the diversity factor assigns particular frequencies for a subset of amino acids, while all of the remaining amino acids (except Cys) are included at a fixed frequency, with the exception of positions 101 and 102 where only a subset of amino acids is present. The design therefore generates an enormous number of theoretically possible variants since all amino acids (except Cys) are present, with varying frequencies, at nearly all HC-CDR3 loop positions and for all HC-CDR3 loop lengths. Even for mid-range length HC-CDR3 loops (for example lengths 9, 10, 11) the actual number of variants present in a library of total complexity $10^{10}$ represents only a fraction of all possible variants according to the design.

Recombinant human antibody libraries incorporating synthetic CDR3 diversity up to a total overall complexity of about $10^{12}$ have been generated (Knappik et al. 2000, Prassler et al., 2011) and have proven successful (selection of antibodies against a particular target) in practical applications, possibly also because of their sheer size. However the generation of libraries of such a size requires a very significant effort and has also a high economic cost.

There is, therefore, the need to design human antibody libraries with optimized properties, i.e. a high probability for selecting good candidate clones for further development into a therapeutic antibody, that can be generated with an acceptable experimental effort and at an acceptable economic cost.

BRIEF DESCRIPTION OF THE FIGURES

FIG. 5: Table of codon-encoding trimer blocks used to generate diversity at positions with more than one amino acid in the HC-CDR3 diversity containing oligonucleotides.

FIG. 8: HC-CDR3 sequences (SEQ ID NOs: 31-168) and HC-CDR3 loop length of approved or clinically developed therapeutic antibodies.

FIG. 11: Oligonucleotide encoding the HC-CDR3 diversity for loop length 15. For positions with more than one amino acid present the mixture of trimer-blocks including the relative frequencies of the individual trimer-blocks is shown. Parts of the oligonucleotide containing the PstI or StyI restrictions sites are indicated in grey.

Figure 1:
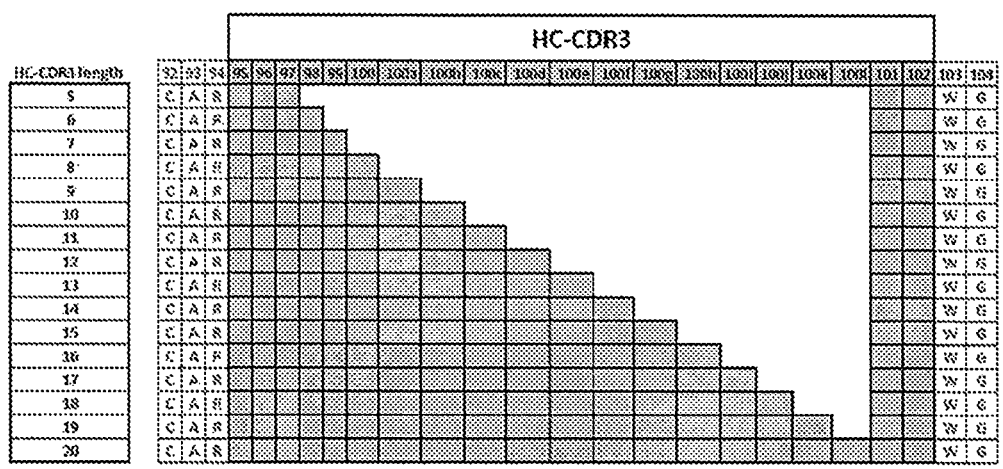
FIG. 1: Kabat numbering scheme for the heavy chain CDR3 region for loop lengths 5 to 20. The HC-CDR3 region is indicated and residues that are part of the HC-CDR3 region are shaded grey. At Kabat positions 92, 93, 94 and 103, 104 preceding and following the HC-CDR3 region, respectively, the most frequently observed amino acids (CAR and WG) are reported.

A) Three rounds of panning were performed and the relative enrichment is represented as INPUT/OUTPUT ratio (total t.u. ×$10^5$); B) The specificity of polyclonal phages mixtures (sublibraries consisting of the eluted phages from I-III round of selection) were tested by phage ELISA on BSA and several unrelated antigens: C) ELISA assay on BSA of single clones isolated from the III round; the dashed line indicates the calculated cutoff used for determining specificity (OD=0.133); D) The specificity of 12 positive clones was tested by phage ELISA on BSA and several unrelated antigens.

FIGS. 13A-13D. Isolation of ovalbumin (OVA) specific M13-scFv clones from the library.

A) Three rounds of panning were performed and the relative enrichment is represented as INPUT/OUTPUT ratio (total t.u. ×10$^5$); B) The specificity of polyclonal phages mixtures (sublibraries consisting of the eluted phages from I-III round of selection) were tested by phage ELISA on OVA and several unrelated antigens; C) ELISA assay on OVA of single clones isolated from the III round; the dashed line indicates the calculated cutoff used for determining specificity (OD=0.166); D) The specificity of 10 positive clones was tested by phage ELISA on OVA and several unrelated antigens.

FIGS. 14A-14D. Isolation of Dsg1 specific M13-scFv clones from the library.

A) Three rounds of panning were performed and the relative enrichment is represented as INPUT/OUTPUT ratio (total t.u. ×10$^5$); B) The specificity of polyclonal phages mixtures (sublibraries consisting of the eluted phages from I-III round of selection) were tested by phage ELISA on commercially available Dsg1 precoated wells and several unrelated antigens; C) ELISA assay on Dsg1 pre-coated wells of single clones isolated from the III round; the dashed line indicates the calculated cutoff used for determining specificity (OD=0.102); D) The specificity of 10 positive clones was tested by phage ELISA on Dsg1 and several unrelated antigens.

FIGS. 15A-15D. Isolation of FGFR4 specific M13-scFv clones from the library.

A) Three rounds of panning were performed and the relative enrichment is represented as INPUT/OUTPUT ratio (total t.u ×10$^5$); B) The specificity of polyclonal phages mixtures (sublibraries consisting of the eluted phages from I-III round of selection) were tested by phage ELISA on FGFR-4 and several unrelated antigens; C) ELISA assay on FGFR-4 of single clones isolated from the III round; the dashed line indicates the calculated cutoff used for determining specificity (OD=0.134); D) The specificity of 20 positive clones was tested by phage ELISA on FGFR-4 and several unrelated antigens.

DEFINITIONS

Unless otherwise defined, all terms of art, notations and other scientific terminology used herein are intended to have the meanings commonly understood by those persons skilled in the art to which this disclosure pertains. In some cases, terms with commonly understood meanings are defined herein for clarity and/or for ready reference; thus, the inclusion of such definitions herein should not be construed to represent a substantial difference over what is generally understood in the art.

The term "library complexity" herein refers to the total number of variants that is present in the library, independently from the HC-CDR3 loop length.

The term "diversity" herein refers to the presence of more than one amino acid at one or more positions.

The term "redundancy" herein refers to the average number of times the variants for a HC-CDR3 loop with a defined length are represented within the library.

With the term "HC-CDR3-only library" we intend a library that has variation only within the HC-CDR3 region and the Kabat position 94 preceding the HC-CDR3 region and that has no variation in the other five CDR regions, HC-CDR1, HC-CDR2, LC-CDR1, LC-CDR2 and LC-CDR3.

The term "antibody fragment" or "functional fragment" as used herein includes any antigen binding fragment, such as Fab, F(ab')2, Fab', Fv, scFv, single chains which include an Fc portion, nanobodies and other antibody like structures having scaffolds other than variable framework regions. The term "functional fragment" includes, but is not limited to any portion of an antibody, that retains the ability to bind to an antigen of interest.

The term "germline" herein refers to a nucleic acid sequence encoding antibodies or functional fragments thereof that are passed down from parent to offspring.

The term "variable heavy chain and variable light chain combination" or "VH/VL combination" herein refers to the combination of one variable heavy chain and one variable light chain. An antibody or a functional antibody fragment comprises at least one variable heavy chain bound to a variable light chain, which form the antigen binding region.

The term "variable domain", light chain variable domain (VL) or heavy chain variable domain (VH), herein refers to the region of an immunoglobulin that is in contact with the antigen and contains the three hypervariable regions referred to as "complementarity determining regions" or "CDRs" (Kabat, 1983; Chothia & Lesk, 1987).

HC-CDR3 and LC-CDR3 herein refer to the third complementarity determining regions of the heavy chain variable and the light chain variable domain, respectively.

The term "Kabat nomenclature" herein refers to the residue numbering scheme of the VL or VH domains as defined by Kabat, 1983 and is schematically shown for the VH domain CDR3 region in FIG. 1. Residue numbering for the VH domain and the HC-CDR3 loop refers to the Kabat nomenclature throughout the present disclosure.

The term "variant" herein refers to an antibody or antibody fragment with an amino acid sequence that is different from the amino acid sequence of all other antibodies or antibody fragments in the library.

The term "codon optimized" or "codon optimization" herein refers to a nucleotide sequence that has been altered in such a way that the encoded amino acid sequence remains the same while codons encoding the individual amino acids have been changed in such a way to optimize the expression of the encoded protein in a particular host, for example bacterial cells.

The term "library" as used herein includes, but is not limited to, phage display, ribosomal display, bacterial display, yeast display and mammalian display libraries. A preferred embodiment of the present invention utilizes a phage display library.

The term "display vector" as used includes a DNA sequence having the ability to direct replication and maintenance of the recombinant DNA molecule extra chromosomally in a host cell, such as a bacterial host cell, transformed therewith. Such DNA sequences are well known in the art.

According to the present invention display vectors can for example be phage vectors or phagemid vectors originating from the class of fd, M13, or fl filamentous bacteriophage. Such vectors are capable of facilitating the display of a protein on the surface of a filamentous bacteriophage.

The term "antibody related peptides" herein refers to peptides that contain structural domains derived from an antibody and may comprise one or more antibody domains that may be covalently linked, disulfide linked or associated as a complex.

The term "genetic packages" as used herein refers to a replicable genetic display package in which the particle is displaying a polypeptide at its surface. The package may be a bacteriophage which displays an antigen binding domain at its surface. When the antigen binding domain corresponds to an antibody related peptide this type of package is called a phage antibody.

DESCRIPTION OF THE INVENTION

The invention provides for a collection of different human antibody HC-CDR3 regions with optimized properties, where diversity is designed through a method that allows, at the desired overall library complexity, for variation of the HC-CDR3 loop length distribution in the library and for variation of the amino acid diversity at each position in each HC-CDR3 loop.

In particular, the present invention generates a human antibody library with optimized properties: reduced combinatorial redundancy (presence of duplicated variants) through optimization of the HC-CDR3 loop length distribution, obtained with an acceptable experimental effort and at a low economic cost.

Said advantages are surprisingly obtained by restricting diversity to only the HC-CDR3 loop and in the position preceding the HC-CDR3 region, such that redundancy is reduced to an acceptable level (less than 2) for all HC-CDR3 loop lengths, and variants for HC-CDR3 loop lengths 9 to 11 are particularly well represented in the library.

The library of the present invention has therefore the advantage to represent particularly well HC-CDR3 loop lengths frequently observed in approved therapeutic antibodies or antibodies in clinical development.

Applying the method of library design optimization disclosed in Example 4, the desired threshold value of redundancy (presence of duplicated variants) can be adjusted for each HC-CDR3 loop length.

At the same time the coverage for each HC-CDR3 loop length (fraction of all possible variants for a particular HC-CDR3 loop length actually present in the library) can be optimized for one or more HC-CDR3 loop lengths of particular interest, within the limits dictated by the overall total complexity of the library.

It is therefore an object of the present invention to generate a library of vectors or genetic packages of overall complexity C that display and express, or comprise a member of a diverse family of antibody related peptides, polypeptides or proteins and collectively display and express, or comprise at least a portion of the diversity of the antibody family, wherein the vectors or genetic packages comprise DNA sequences that encode a HC-CDR3 region and the position preceding the HC-CDR3 region having the following sequence:

$ZX_1Y_nX_3X_4X_5$ wherein:
$C=1.3\times10^{10}$
Z corresponds to Kabat position 94;
$X_1$ corresponds to Kabat position 95;
n is an integer from 3 to 11;
Y corresponds to HC Kabat positions 96 to 98 (n=3), or HC Kabat positions 96 to 99 (n=4), or HC Kabat positions 96 to 100 (n=5), or HC Kabat positions 96 to 100a (n=6), or HC Kabat positions 96 to 100b (n=7), or HC Kabat positions 96 to 100c (n=8), or HC Kabat positions 96 to 100d (n=9), or HC Kabat positions 96 to 100e (n=10) or HC Kabat positions 96 to 100f (n=11);

$X_3$ corresponds to HC Kabat position 99 (n=3), or to HC Kabat position 100 (n=4), or HC Kabat position 100a (n=5), or HC Kabat position 100b (n=6), or HC Kabat position 100c (n=7), or HC Kabat position 100d (n=8), or HC Kabat position 100e (n=9), or HC Kabat position 100f (n=10), or HC Kabat position 100g (n=11);
$X_4$ corresponds to HC Kabat position 101;
$X_5$ corresponds to HC Kabat position 102;
characterized in that the percentage fraction p(L) (L=n+4) of each $ZX_1Y_nX_3X_4X_5$ region is present in the library according to the values given in Table 2C;
and in that positions Z, $X_1$, $X_2$, $X_3$, $X_4$, $X_5$ and $Y_n$ (n=3 to 11) for each HC-CDR3 region of length L=n+4 are occupied by defined amino acids according to the relative frequency disclosed in Tables 3A-3I.

In a preferred embodiment, said antibody related peptides, polypeptides or proteins are from humans.

In a further embodiment said antibody related peptides, polypeptides or proteins are from cat or dog.

In a further preferred embodiment in the library of vectors or genetic packages of the present invention the lengths of the HC-CDR3 loops range from 9 to 11. In an embodiment of the present invention the antibody related peptides, polypeptides or proteins are antibodies or fragments thereof, selected from an antibody comprising one or more constant domains, a single-chain antibody, a FAB fragment, a heavy-chain only antibody or a variable heavy chain only domain.

Preferably, said antibody or fragments thereof is a single-chain antibody.

In a further embodiment the antibody related peptides, polypeptides or proteins according to the present invention comprise human antibody germline variable segments.

In a further embodiment of the present invention said HC-CDR3 only region is introduced into a constant single-chain scaffold characterized by a human heavy and light chain germline variable domains, wherein the light chain CDR3 region is of length 9.

Said sequences represent those amino acids most frequently observed at each of the nine positions of the light chain CDR3 in natural human antibodies.

The use of germline variable domain sequences in the single-chain scaffold is advantageous because these sequences do not contain somatic mutations and are therefore expected to be less immunogenic reducing the likelihood to subsequently observe human anti-human antibody response during clinical testing in human subjects. In a preferred embodiment of the present invention the antibody related peptides, polypeptides or proteins comprises a human antibody VK1 light chain variable domain containing human germline sequences and a human antibody VH3 heavy chain variable domain containing human germline sequences.

Preferably, said VK1 kappa light chain variable domain contains the human germline sequences SEQ ID NO. 3 and SEQ ID NO. 4, the light chain CDR3 region contains the sequence SEQ ID NO. 5 and the VH3 heavy chain variable domain contains the human germline sequences SEQ ID NO. 1 and SEQ ID NO. 2.

In a further preferred embodiment in the library of vectors or genetic package according to the present invention, the VH3 heavy chain variable domain comprising the human germline sequence is connected to a human antibody VK1 kappa light chain variable domain comprising the human germline sequence with a linker of SEQ ID NO. 6.

According to a further embodiment the base vector used to produce the library of the present invention has the SEQ ID NO. 8.

In a further embodiment the library of vectors or genetic package according to the present invention is used for the selection of antibodies against target antigens.

Preferably, sad library is displayed on phage for selection against target antigens.

According to the present invention the library of vectors or genetic packages has diversity restricted to the HC-CDR3 region and to the position preceding HC-CDR3.

The library incorporating the HC-CDR3 diversity and the methods of the present invention will now be more fully described by the following examples. However it should be noted that such examples are given by way of illustration and not of limitation.

EXAMPLES

Figure 2:
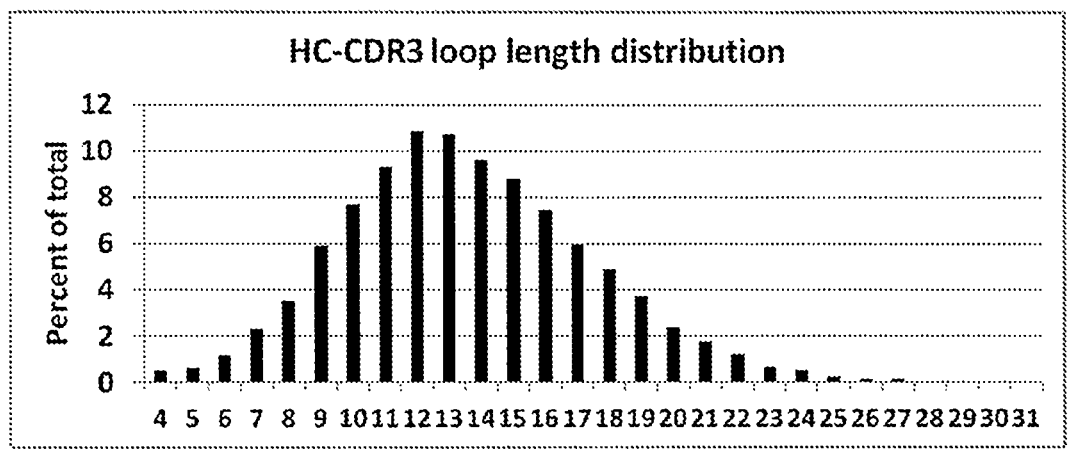
FIG. 2: Distribution of HC-CDR3 loop lengths observed in natural antibodies.

Example 1. Analysis of Sequence and Length Variation in Variable Domains from Natural Antibodies High-throughput next-generation sequencing data for HC-CDR3 loop regions was downloaded from the NCBI SRA archive SRR400158 (Ippolito et al, 2012) and examined for length and amino acid composition of the encoded HC-CDR3 loops (FIG. 2) following the Kabat nomenclature (FIG. 1). The HC-CDR3 loop length distribution has a maximum at loop length 12 (FIG. 2). Amino acid composition at each loop position for HC-CDR3 loop lengths 7 to 15 from natural antibodies are shown in Tables 1a-1i.

TABLE 1a

Amino acid composition for HC-CDR3 loops of length 7 in natural antibodies. Below each loop position (top row, Kabat nomenclature, HC-CDR3 corresponds to positions 95 to 102) the observed percent frequencies for each amino acid at that position are shown. Amino acids with observed frequencies less than 0.05% are not shown.

| 92 | 93 | 94 | 95 | 96 | 97 | 98 | 99 | 101 | 102 | 103 |
|---|---|---|---|---|---|---|---|---|---|---|
| C(100.0%) | A(84.5%) | R(63.4%) | G(25.4%) | G(15.7%) | G(22.1%) | G(18.7%) | F(25.6%) | D(56.5%) | Y(47.3%) | W(100.0%) |
| | T(5.2%) | S(8.9%) | D(15.5%) | R(10.8%) | S(11.8%) | S(13.7%) | L(14.3%) | S(8.0%) | V(8.8%) | |
| | V(3.3%) | T(7.3%) | E(7.0%) | D(10.5%) | D(9.7%) | A(11.6%) | G(7.9%) | G(6.5%) | P(8.3%) | |
| | S(2.8%) | K(5.8%) | W(7.0%) | S(10.2%) | Y(7.4%) | Y(11.4%) | S(7.3%) | T(3.5%) | I(5.2%) | |
| | G(2.2%) | A(4.6%) | R(6.1%) | L(6.8%) | R(6.9%) | W(5.2%) | V(5.6%) | N(3.4%) | G(4.8%) | |
| | N(0.6%) | G(2.4%) | V(6.0%) | A(6.0%) | A(6.2%) | T(4.9%) | Y(5.6%) | Y(3.0%) | S(4.2%) | |
| | I(0.4%) | V(1.3%) | A(5.5%) | V(5.3%) | T(5.3%) | V(4.7%) | M(5.2%) | A(2.7%) | L(3.8%) | |
| | E(0.3%) | H(1.1%) | L(5.1%) | P(5.0%) | V(5.0%) | R(4.4%) | I(4.7%) | V(2.5%) | A(3.1%) | |
| | K(0.3%) | L(1.0%) | S(4.4%) | T(4.2%) | N(3.9%) | P(4.3%) | P(4.2%) | E(2.5%) | N(2.6%) | |
| | R(0.2%) | I(0.8%) | Y(2.7%) | Y(4.1%) | P(3.8%) | L(3.8%) | A(3.9%) | L(1.8%) | D(2.5%) | |
| | M(0.1%) | E(0.7%) | Q(2.6%) | N(3.3%) | L(3.7%) | D(3.7%) | D(2.9%) | P(1.7%) | H(2.1%) | |
| | D(0.1%) | N(0.7%) | T(2.4%) | E(3.1%) | E(3.4%) | N(2.9%) | T(2.6%) | R(1.5%) | F(1.9%) | |
| | | P(0.5%) | H(2.3%) | W(2.8%) | W(3.3%) | E(2.7%) | N(2.4%) | W(1.3%) | T(1.7%) | |
| | | W(0.3%) | I(2.0%) | K(2.4%) | I(1.6%) | F(1.8%) | R(1.9%) | H(1.1%) | R(1.5%) | |
| | | M(0.3%) | P(1.6%) | H(2.4%) | F(1.5%) | I(1.7%) | E(1.7%) | I(1.1%) | C(0.7%) | |
| | | C(0.3%) | N(1.3%) | Q(2.2%) | Q(1.5%) | Q(1.5%) | W(1.7%) | F(1.0%) | K(0.5%) | |
| | | D(0.2%) | F(1.1%) | F(2.1%) | H(1.1%) | H(1.1%) | H(0.9%) | Q(0.8%) | E(0.3%) | |
| | | Q(0.2%) | K(1.1%) | I(1.8%) | M(0.8%) | K(1.1%) | Q(0.7%) | K(0.3%) | Q(0.3%) | |
| | | Y(0.1%) | M(0.8%) | M(1.2%) | K(0.7%) | M(0.7%) | K(0.7%) | M(0.3%) | W(0.3%) | |
| | | F(0.1%) | C(0.2%) | C(0.1%) | C(0.2%) | C(0.1%) | C(0.5%) | C(0.1%) | M(0.1%) | |

TABLE 1b

Amino acid composition for HC-CDR3 loops of length 8 in natural antibodies. Below each loop position (top row, Kabat nomenclature, HC-CDR3 corresponds to positions 95 to 102) the observed percent frequencies for each amino acid at that position are shown. Amino acids with observed frequencies less than 0.05% are not shown.

| 92 | 93 | 94 | 95 | 96 | 97 | 98 | 99 | 100 | 101 | 102 | 103 |
|---|---|---|---|---|---|---|---|---|---|---|---|
| C(100.0%) | A(88.0%) | R(70.0%) | G(21.0%) | G(14.3%) | G(20.6%) | G(25.8%) | G(16.6%) | F(33.4%) | D(66.1%) | Y(54.8%) | W(100.0%) |
| | T(5.3%) | T(6.8%) | D(19.8%) | S(11.1%) | S(14.6%) | S(12.3%) | A(13.6%) | L(10.2%) | G(6.6%) | P(8.2%) | |
| | V(4.0%) | S(6.5%) | E(8.6%) | R(10.8%) | A(7.4%) | Y(9.9%) | Y(12.5%) | G(6.8%) | S(3.4%) | I(7.1%) | |
| | G(1.1%) | K(5.7%) | V(7.7%) | L(8.4%) | R(7.0%) | D(7.2%) | S(10.0%) | Y(6.4%) | Y(2.9%) | V(6.6%) | |
| | S(0.8%) | G(2.5%) | A(6.1%) | V(6.0%) | Y(6.3%) | A(6.6%) | W(6.5%) | S(5.2%) | L(2.2%) | S(3.6%) | |
| | N(0.2%) | A(2.2%) | S(5.7%) | A(5.8%) | D(6.2%) | R(5.9%) | L(5.3%) | I(5.2%) | N(2.2%) | D(3.1%) | |
| | I(0.2%) | H(1.2%) | R(5.5%) | D(5.8%) | V(5.3%) | T(5.2%) | T(5.2%) | V(5.1%) | T(2.0%) | L(3.0%) | |
| | E(0.2%) | I(1.1%) | L(4.9%) | P(5.6%) | T(5.2%) | W(4.3%) | V(4.3%) | M(4.9%) | V(1.9%) | H(2.6%) | |
| | M(0.1%) | V(1.1%) | H(3.2%) | Y(5.3%) | L(4.4%) | N(4.2%) | D(4.2%) | P(4.3%) | A(1.8%) | N(2.0%) | |

TABLE 1b-continued

Amino acid composition for HC-CDR3 loops of length 8 in natural antibodies. Below each loop position (top row, Kabat nomenclature, HC-CDR3 corresponds to positions 95 to 102) the observed percent frequencies for each amino acid at that position are shown. Amino acids with observed frequencies less than 0.05% are not shown.

| 92 | 93 | 94 | 95 | 96 | 97 | 98 | 99 | 100 | 101 | 102 | 103 |
|----|----|----|----|----|----|----|----|-----|-----|-----|-----|
|    | R(0.1%) | L(0.6%) | T(2.9%) | T(5.1%) | E(3.6%) | L(3.6%) | R(3.8%) | A(3.8%) | R(1.8%) | F(1.9%) |   |
|    | K(0.1%) | Y(0.4%) | Q(2.8%) | E(3.3%) | N(3.3%) | V(3.5%) | P(3.1%) | T(3.3%) | P(1.5%) | G(1.7%) |   |
|    |         | P(0.3%) | W(2.5%) | I(3.1%) | P(3.0%) | E(2.6%) | N(2.5%) | D(2.0%) | E(1.5%) | T(1.2%) |   |
|    |         | Q(0.3%) | Y(2.2%) | Q(2.9%) | W(2.8%) | P(1.6%) | E(2.3%) | N(2.0%) | F(1.4%) | A(1.1%) |   |
|    |         | M(0.3%) | I(1.8%) | W(2.3%) | I(2.5%) | H(1.5%) | F(2.0%) | W(1.9%) | I(1.1%) | R(1.0%) |   |
|    |         | C(0.2%) | N(1.4%) | H(2.3%) | Q(2.1%) | F(1.5%) | I(1.9%) | E(1.7%) | H(1.0%) | E(0.6%) |   |
|    |         | N(0.2%) | P(1.3%) | N(2.2%) | H(1.7%) | I(1.4%) | H(1.7%) | H(1.2%) | Q(0.8%) | C(0.6%) |   |
|    |         | W(0.2%) | F(1.1%) | F(2.1%) | F(1.5%) | Q(1.4%) | Q(1.5%) | C(0.8%) | W(0.7%) | W(0.4%) |   |
|    |         | E(0.2%) | K(0.6%) | K(2.0%) | K(1.4%) | M(0.9%) | K(1.1%) | R(0.8%) | K(0.5%) | Q(0.3%) |   |
|    |         | F(0.1%) | M(0.5%) | M(1.0%) | M(0.9%) | K(0.5%) | M(1.0%) | Q(0.6%) | M(0.2%) | M(0.2%) |   |
|    |         |         | C(0.4%) | C(0.3%) | C(0.1%) | C(0.1%) | C(0.8%) | K(0.4%) | C(0.1%) | K(0.1%) |   |

TABLE 1c

Amino acid composition for HC-CDR3 loops of length 9 in natural antibodies. Below each loop position (top row, Kabat nomenclature, HC-CDR3 corresponds to positions 95 to 102) the observed percent frequencies for each amino acid at that position are shown. Amino acids with observed frequencies less than 0.05% are not shown.

| 92 | 93 | 94 | 95 | 96 | 97 | 98 |
|----|----|----|----|----|----|----|
| C(100.0%) | A(90.9%) | R(72.7%) | G(20.6%) | G(18.3%) | G(18.5%) | G(17.5%) |
|           | T(4.2%)  | S(6.4%)  | D(16.9%) | R(10.3%) | S(12.9%) | S(14.6%) |
|           | V(2.7%)  | K(5.7%)  | E(8.2%)  | S(10.1%) | A(7.5%)  | A(8.8%)  |
|           | G(1.0%)  | T(5.1%)  | V(7.5%)  | P(6.7%)  | R(7.3%)  | Y(8.2%)  |
|           | S(0.6%)  | G(2.1%)  | A(7.3%)  | L(6.5%)  | Y(6.9%)  | L(6.4%)  |
|           | D(0.2%)  | A(1.4%)  | R(6.9%)  | D(6.2%)  | V(6.5%)  | V(5.6%)  |
|           | E(0.1%)  | H(1.4%)  | S(6.0%)  | V(5.8%)  | T(6.1%)  | D(5.5%)  |
|           | I(0.1%)  | L(0.9%)  | L(5.2%)  | A(5.4%)  | P(5.1%)  | R(5.3%)  |
|           | N(0.1%)  | V(0.8%)  | H(4.2%)  | Y(5.3%)  | D(5.0%)  | T(5.0%)  |
|           | M(0.1%)  | I(0.8%)  | Q(3.2%)  | T(4.5%)  | L(4.1%)  | W(3.9%)  |
|           |          | N(0.7%)  | T(2.9%)  | I(3.4%)  | I(3.1%)  | P(3.5%)  |
|           |          | E(0.3%)  | Y(2.2%)  | E(3.3%)  | E(3.0%)  | E(3.1%)  |
|           |          | Q(0.3%)  | I(1.9%)  | Q(2.6%)  | Q(2.8%)  | N(2.4%)  |
|           |          | Y(0.3%)  | P(1.7%)  | K(2.5%)  | W(2.8%)  | F(2.2%)  |
|           |          | C(0.3%)  | W(1.7%)  | N(2.3%)  | F(2.4%)  | I(2.1%)  |
|           |          | M(0.2%)  | F(1.4%)  | W(2.0%)  | N(2.2%)  | Q(1.9%)  |
|           |          | P(0.2%)  | N(0.8%)  | F(2.0%)  | K(1.5%)  | H(1.5%)  |
|           |          | W(0.2%)  | K(0.7%)  | H(1.8%)  | H(1.3%)  | M(1.4%)  |
|           |          | D(0.1%)  | M(0.5%)  | M(0.9%)  | M(0.9%)  | K(0.9%)  |
|           |          | F(0.1%)  | C(0.3%)  | C(0.2%)  | C(0.1%)  | C(0.2%)  |

| 99 | 100 | 100a | 101 | 102 | 103 |
|----|-----|------|-----|-----|-----|
| G(20.4%) | G(16.5%) | F(41.2%) | D(74.0%) | Y(57.3%) | W(100.0%) |
| Y(11.8%) | A(12.9%) | L(10.6%) | G(5.8%)  | P(9.5%)  |           |
| S(10.9%) | Y(12.1%) | M(5.8%)  | S(2.4%)  | I(7.7%)  |           |
| A(7.9%)  | S(9.4%)  | Y(5.7%)  | V(2.1%)  | V(7.2%)  |           |
| D(7.7%)  | W(7.8%)  | I(5.6%)  | Y(1.9%)  | L(3.2%)  |           |
| T(5.5%)  | P(6.6%)  | V(4.9%)  | L(1.7%)  | S(2.5%)  |           |
| R(5.3%)  | T(4.7%)  | G(4.3%)  | N(1.6%)  | H(2.5%)  |           |
| W(5.0%)  | L(4.7%)  | P(3.9%)  | A(1.5%)  | D(2.3%)  |           |
| N(4.8%)  | D(4.3%)  | S(3.6%)  | T(1.4%)  | N(1.8%)  |           |
| L(4.7%)  | V(4.0%)  | A(2.9%)  | E(1.4%)  | F(1.5%)  |           |
| V(3.3%)  | R(3.0%)  | T(2.6%)  | R(1.0%)  | G(1.1%)  |           |
| E(2.3%)  | E(2.6%)  | N(1.5%)  | P(0.9%)  | T(1.1%)  |           |
| P(2.1%)  | N(2.3%)  | W(1.4%)  | I(0.9%)  | A(0.6%)  |           |
| F(1.6%)  | H(2.0%)  | D(1.3%)  | Q(0.9%)  | R(0.6%)  |           |
| H(1.5%)  | F(1.8%)  | R(1.2%)  | H(0.7%)  | C(0.4%)  |           |
| Q(1.3%)  | I(1.6%)  | H(1.0%)  | F(0.6%)  | Q(0.3%)  |           |
| K(1.2%)  | Q(1.0%)  | E(1.0%)  | W(0.4%)  | E(0.2%)  |           |
| M(1.2%)  | K(0.8%)  | C(0.6%)  | K(0.3%)  | W(0.1%)  |           |
| I(1.2%)  | C(0.8%)  | Q(0.5%)  | M(0.2%)  | K(0.1%)  |           |
| C(0.3%)  | M(0.7%)  | K(0.5%)  | C(0.2%)  |          |           |

TABLE 1d

Amino acid composition for HC-CDR3 loops of length 10 in natural antibodies. Below each loop position (top row, Kabat nomenclature, HC-CDR3 corresponds to positions 95 to 102) the observed percent frequencies for each amino acid at that position are shown. Amino acids with observed frequencies less than 0.05% are not shown.

| 92 | 93 | 94 | 95 | 96 | 97 | 98 |
|---|---|---|---|---|---|---|
| C(100.0%) | A(92.0%) | R(72.3%) | G(18.4%) | G(15.8%) | G(17.8%) | G(18.1%) |
|  | T(4.2%) | K(7.4%) | D(17.0%) | R(11.7%) | S(12.8%) | S(14.7%) |
|  | V(2.2%) | S(6.6%) | E(8.7%) | S(10.5%) | Y(8.1%) | A(9.2%) |
|  | G(0.6%) | T(4.8%) | R(7.2%) | P(7.4%) | A(7.6%) | Y(8.7%) |
|  | S(0.4%) | G(2.1%) | V(7.1%) | L(7.2%) | R(7.3%) | V(7.2%) |
|  | I(0.3%) | H(1.7%) | A(6.9%) | V(5.9%) | V(6.5%) | D(5.4%) |
|  | D(0.1%) | A(1.3%) | S(6.6%) | D(5.3%) | D(6.0%) | T(5.2%) |
|  | R(0.1%) | I(0.8%) | L(5.5%) | A(5.3%) | T(5.9%) | R(5.2%) |
|  | E(0.1%) | L(0.5%) | H(5.2%) | Y(4.9%) | P(4.6%) | L(4.1%) |
|  |  | N(0.5%) | Q(2.9%) | T(4.2%) | L(4.5%) | W(3.5%) |
|  |  | V(0.4%) | T(2.6%) | E(3.5%) | I(3.2%) | P(3.4%) |
|  |  | P(0.3%) | Y(2.3%) | I(3.5%) | E(2.9%) | E(3.1%) |
|  |  | Y(0.2%) | P(2.2%) | Q(3.1%) | W(2.6%) | I(2.9%) |
|  |  | M(0.2%) | I(1.8%) | H(2.2%) | Q(2.4%) | N(2.1%) |
|  |  | C(0.2%) | F(1.5%) | N(2.1%) | F(2.0%) | Q(2.1%) |
|  |  | Q(0.1%) | W(1.1%) | F(2.1%) | K(1.7%) | F(1.7%) |
|  |  | E(0.1%) | K(1.0%) | W(2.0%) | N(1.6%) | M(1.2%) |
|  |  | F(0.1%) | N(0.9%) | K(1.8%) | M(1.4%) | H(1.0%) |
|  |  | W(0.1%) | M(0.6%) | M(1.1%) | H(1.1%) | K(0.8%) |
|  |  | D(0.1%) | C(0.5%) | C(0.3%) | C(0.2%) | C(0.1%) |

| 99 | 100 | 100a | 100b | 101 | 102 | 103 |
|---|---|---|---|---|---|---|
| G(17.5%) | G(16.8%) | Y(16.5%) | F(48.4%) | D(79.0%) | Y(59.4%) | W(100.0%) |
| S(12.9%) | Y(14.0%) | G(14.3%) | L(10.1%) | G(5.1%) | I(8.8%) |  |
| Y(9.6%) | S(11.4%) | A(13.3%) | M(5.8%) | S(1.6%) | P(8.7%) |  |
| A(9.4%) | D(8.8%) | W(7.4%) | I(5.0%) | A(1.4%) | V(6.8%) |  |
| T(7.0%) | A(7.1%) | P(7.2%) | Y(4.5%) | V(1.4%) | L(3.2%) |  |
| L(5.8%) | T(5.4%) | S(7.0%) | V(4.4%) | L(1.3%) | S(2.6%) |  |
| V(5.6%) | N(5.2%) | L(4.6%) | G(3.8%) | Y(1.3%) | H(2.3%) |  |
| D(5.5%) | W(4.9%) | T(4.3%) | P(3.5%) | T(1.2%) | D(1.6%) |  |
| W(4.6%) | R(4.7%) | V(4.0%) | S(3.2%) | E(1.2%) | F(1.4%) |  |
| R(4.3%) | L(4.3%) | D(3.3%) | A(1.9%) | N(1.1%) | N(1.4%) |  |
| P(3.5%) | V(3.7%) | R(3.1%) | T(1.7%) | Q(1.0%) | T(0.8%) |  |
| E(2.7%) | P(2.7%) | N(2.5%) | W(1.2%) | P(0.8%) | G(0.7%) |  |
| N(2.6%) | E(2.0%) | H(2.5%) | E(1.1%) | R(0.8%) | R(0.7%) |  |
| I(2.0%) | H(1.8%) | E(2.4%) | R(1.0%) | I(0.6%) | A(0.5%) |  |
| F(1.8%) | F(1.6%) | F(1.8%) | D(1.0%) | F(0.6%) | C(0.4%) |  |
| Q(1.5%) | K(1.3%) | I(1.7%) | N(1.0%) | H(0.5%) | Q(0.2%) |  |
| H(1.5%) | Q(1.3%) | Q(1.3%) | H(0.8%) | W(0.4%) | E(0.2%) |  |
| K(1.0%) | M(1.1%) | C(1.0%) | C(0.8%) | C(0.2%) | M(0.1%) |  |
| M(1.0%) | I(1.1%) | K(0.9%) | Q(0.5%) | M(0.2%) | K(0.1%) |  |
| C(0.2%) | C(0.5%) | M(0.7%) | K(0.2%) | K(0.1%) | W(0.1%) |  |

45

TABLE 1e

Amino acid composition for HC-CDR3 loops of length 11 in natural antibodies. Below each loop position (top row, Kabat nomenclature, HC-CDR3 corresponds to position 95 to 102) the observed percent frequencies for each amino acid at that position are shown. Amino acids with observed frequencies less than 0.05% are not shown.

| 92 | 93 | 94 | 95 | 96 | 97 | 98 | 99 |
|---|---|---|---|---|---|---|---|
| C(100.0%) | A(91.9%) | R(71.5%) | G(19.4%) | G(17.0%) | G(17.2%) | G(18.1%) | G(19.4%) |
|  | T(4.5%) | K(10.0%) | D(18.4%) | R(11.1%) | S(12.8%) | S(15.4%) | S(15.4%) |
|  | V(2.4%) | S(6.2%) | E(7.7%) | S(9.7%) | Y(8.7%) | Y(11.3%) | A(9.9%) |
|  | G(0.5%) | T(4.9%) | V(7.5%) | P(7.4%) | R(7.6%) | A(9.4%) | Y(9.8%) |
|  | I(0.2%) | G(1.9%) | A(7.4%) | L(7.2%) | A(6.8%) | V(6.5%) | V(6.5%) |
|  | S(0.2%) | H(1.3%) | R(7.0%) | Y(5.7%) | V(6.7%) | D(5.7%) | T(5.6%) |
|  | D(0.1%) | A(1.1%) | S(5.9%) | D(5.3%) | D(5.7%) | T(5.1%) | D(5.5%) |
|  | R(0.1%) | I(0.9%) | L(5.5%) | A(5.1%) | T(5.0%) | R(4.2%) | L(4.4%) |
|  | E(0.1%) | V(0.4%) | H(4.2%) | V(5.0%) | P(4.5%) | L(4.1%) | R(4.1%) |
|  |  | N(0.4%) | T(3.3%) | T(4.0%) | L(4.2%) | W(3.3%) | W(3.8%) |
|  |  | L(0.3%) | P(3.0%) | I(3.6%) | I(3.9%) | I(3.3%) | P(3.0%) |
|  |  | E(0.2%) | Q(2.8%) | E(3.2%) | E(3.1%) | P(2.5%) | I(2.2%) |
|  |  | P(0.2%) | Y(1.6%) | Q(2.8%) | W(2.9%) | E(2.2%) | E(2.1%) |
|  |  | C(0.2%) | I(1.5%) | H(2.6%) | N(2.0%) | F(2.1%) | N(1.9%) |

TABLE 1e-continued

Amino acid composition for HC-CDR3 loops of length 11 in natural antibodies. Below each loop position (top row, Kabat nomenclature, HC-CDR3 corresponds to position 95 to 102) the observed percent frequencies for each amino acid at that position are shown. Amino acids with observed frequencies less than 0.05% are not shown.

|  |  | M(0.1%) | F(1.2%) | F(2.5%) | H(1.8%) | N(1.8%) | Q(1.7%) |
|---|---|---|---|---|---|---|---|
|  |  | Y(0.1%) | N(1.1%) | N(2.2%) | Q(1.7%) | Q(1.7%) | F(1.7%) |
|  |  | Q(0.1%) | W(0.8%) | K(2.1%) | M(1.7%) | M(1.5%) | M(1.1%) |
|  |  | W(0.1%) | K(0.7%) | W(1.6%) | F(1.5%) | H(0.8%) | H(0.9%) |
|  |  | F(0.1%) | M(0.7%) | M(1.2%) | K(1.3%) | K(0.8%) | K(0.8%) |
|  |  |  | C(0.5%) | C(0.5%) | C(0.6%) | C(0.1%) | C(0.3%) |

| 100 | 100a | 100b | 100c | 101 | 102 | 103 |
|---|---|---|---|---|---|---|
| G(15.3%) | Y(17.3%) | Y(17.3%) | F(50.6%) | D(81.3%) | Y(58.4%) | W(100.0%) |
| S(13.4%) | G(15.8%) | G(15.6%) | L(9.9%) | G(4.4%) | P(10.2%) |  |
| Y(11.8%) | S(10.1%) | A(11.9%) | M(7.1%) | E(1.5%) | I(8.2%) |  |
| A(8.3%) | D(7.4%) | W(9.0%) | I(4.9%) | Y(1.3%) | V(7.9%) |  |
| T(6.6%) | N(5.9%) | P(7.5%) | Y(4.6%) | S(1.3%) | L(2.8%) |  |
| L(5.4%) | R(5.6%) | S(5.8%) | V(4.1%) | N(1.2%) | H(2.5%) |  |
| D(5.4%) | A(5.5%) | L(4.7%) | P(3.3%) | Q(1.2%) | S(2.4%) |  |
| W(5.1%) | T(5.1%) | T(4.3%) | G(3.1%) | V(1.1%) | F(1.5%) |  |
| R(4.9%) | W(4.9%) | V(3.4%) | S(2.7%) | T(1.1%) | D(1.3%) |  |
| V(4.7%) | L(4.5%) | R(2.9%) | T(1.5%) | A(1.0%) | N(1.1%) |  |
| P(3.6%) | V(3.5%) | D(2.8%) | A(1.5%) | L(0.9%) | T(1.0%) |  |
| E(2.9%) | P(3.0%) | N(2.7%) | W(1.3%) | H(0.7%) | C(0.8%) |  |
| N(2.7%) | E(2.5%) | F(2.5%) | N(0.9%) | P(0.6%) | G(0.5%) |  |
| F(2.2%) | F(2.0%) | H(2.3%) | R(0.9%) | R(0.6%) | A(0.4%) |  |
| I(1.8%) | H(1.7%) | E(2.1%) | E(0.8%) | F(0.5%) | R(0.3%) |  |
| Q(1.7%) | I(1.5%) | I(1.5%) | C(0.8%) | I(0.4%) | W(0.2%) |  |
| K(1.4%) | K(1.1%) | C(1.4%) | D(0.8%) | W(0.3%) | K(0.2%) |  |
| H(1.4%) | Q(1.1%) | Q(1.1%) | H(0.7%) | M(0.2%) | E(0.1%) |  |
| M(1.1%) | C(0.7%) | K(0.8%) | Q(0.4%) | K(0.2%) | Q(0.1%) |  |
| C(0.3%) | M(0.7%) | M(0.5%) | K(0.2%) | C(0.1%) | M(0.1%) |  |

TABLE 1f

Amino acid composition for HC-CDR3 loops of length 12 in natural antibodies. Below each loop position (top row, Kabat nomenclature, HC-CDR3 corresponds to positions 95 to 102) the observed percent frequencies for each amino acid at that position are shown. Amino acids with observed frequencies less than 0.05% are not shown.

| 92 | 93 | 94 | 95 | 96 | 97 | 98 | 99 |
|---|---|---|---|---|---|---|---|
| C(100.0%) | A(92.7%) | R(72.2%) | D(20.7%) | G(16.2%) | G(17.4%) | G(16.3%) | G(17.6%) |
|  | T(3.7%) | K(11.8%) | G(17.9%) | R(12.6%) | S(11.2%) | S(15.8%) | S(17.2%) |
|  | V(2.3%) | S(5.1%) | E(8.4%) | P(8.6%) | Y(10.8%) | Y(10.9%) | Y(10.8%) |
|  | G(0.6%) | T(4.3%) | A(7.7%) | S(8.4%) | R(7.6%) | V(7.8%) | A(10.5%) |
|  | S(0.3%) | G(1.4%) | V(7.6%) | L(8.1%) | A(6.8%) | A(7.5%) | V(6.0%) |
|  | I(0.1%) | H(1.1%) | R(6.3%) | V(5.5%) | V(6.5%) | D(6.0%) | D(6.0%) |
|  | D(0.1%) | A(1.0%) | S(5.4%) | Y(5.1%) | D(5.6%) | T(5.3%) | T(5.3%) |
|  | E(0.1%) | I(0.7%) | L(5.0%) | A(4.8%) | T(4.8%) | R(4.7%) | L(4.1%) |
|  |  | N(0.4%) | H(4.8%) | D(4.7%) | L(4.6%) | L(4.2%) | R(3.9%) |
|  |  | L(0.3%) | T(3.0%) | T(4.0%) | I(4.0%) | I(3.5%) | W(3.4%) |
|  |  | V(0.3%) | Q(2.8%) | E(3.5%) | P(3.9%) | W(3.0%) | I(2.5%) |
|  |  | E(0.3%) | P(2.7%) | I(3.4%) | E(3.0%) | P(2.9%) | N(2.1%) |
|  |  | M(0.2%) | I(1.7%) | Q(2.7%) | W(2.4%) | E(2.4%) | P(2.0%) |
|  |  | C(0.2%) | Y(1.3%) | K(2.4%) | Q(2.4%) | Q(2.1%) | F(1.9%) |
|  |  | Q(0.2%) | F(1.1%) | H(2.1%) | N(2.0%) | N(2.0%) | Q(1.9%) |
|  |  | P(0.1%) | N(1.0%) | N(1.9%) | F(1.6%) | F(1.8%) | E(1.8%) |
|  |  | Y(0.1%) | K(0.8%) | W(1.9%) | H(1.6%) | M(1.4%) | M(1.2%) |
|  |  |  | W(0.8%) | F(1.8%) | K(1.4%) | H(1.1%) | H(0.7%) |
|  |  |  | M(0.6%) | M(1.5%) | C(1.2%) | K(0.8%) | K(0.6%) |
|  |  |  | C(0.4%) | C(0.7%) | M(1.2%) | C(0.4%) | C(0.4%) |

| 100 | 100a | 100b | 100c | 100d | 101 | 102 | 103 |
|---|---|---|---|---|---|---|---|
| G(18.3%) | G(13.6%) | Y(18.1%) | Y(20.7%) | F(57.6%) | D(83.9%) | Y(53.9%) | W(100.0%) |
| S(15.2%) | S(13.3%) | G(16.1%) | G(15.6%) | L(9.0%) | G(3.6%) | P(12.7%) |  |
| Y(11.4%) | Y(12.9%) | S(9.1%) | A(13.1%) | M(7.7%) | Q(1.7%) | I(9.9%) |  |
| A(8.9%) | A(6.8%) | D(8.7%) | W(11.1%) | Y(3.9%) | N(1.1%) | V(9.1%) |  |
| T(6.3%) | T(6.6%) | N(7.5%) | P(6.8%) | I(3.7%) | E(1.0%) | L(3.6%) |  |
| V(6.0%) | L(6.2%) | W(4.9%) | S(4.9%) | V(3.0%) | A(1.0%) | H(3.1%) |  |
| D(4.9%) | W(5.2%) | R(4.8%) | L(3.8%) | P(2.8%) | V(1.0%) | S(2.3%) |  |

TABLE 1f-continued

Amino acid composition for HC-CDR3 loops of length 12 in natural antibodies. Below each loop position (top row, Kabat nomenclature, HC-CDR3 corresponds to positions 95 to 102) the observed percent frequencies for each amino acid at that position are shown. Amino acids with observed frequencies less than 0.05% are not shown.

| | | | | | | |
|---|---|---|---|---|---|---|
| W(4.7%) | R(5.0%) | T(4.8%) | T(3.7%) | S(2.5%) | S(1.0%) | F(1.4%) |
| L(4.5%) | P(4.8%) | A(4.3%) | V(2.9%) | G(2.5%) | Y(0.9%) | D(0.8%) |
| R(3.9%) | V(4.8%) | P(3.4%) | D(2.6%) | A(1.2%) | T(0.8%) | N(0.7%) |
| P(3.4%) | D(4.5%) | L(3.1%) | R(2.3%) | T(1.1%) | L(0.7%) | T(0.6%) |
| I(2.2%) | N(3.0%) | V(2.8%) | F(2.1%) | N(0.9%) | H(0.7%) | G(0.4%) |
| E(2.2%) | E(2.8%) | E(2.3%) | H(2.1%) | W(0.9%) | R(0.6%) | A(0.3%) |
| N(1.9%) | F(2.3%) | H(2.1%) | N(2.0%) | R(0.7%) | P(0.5%) | C(0.3%) |
| F(1.6%) | H(2.0%) | F(2.0%) | E(1.7%) | E(0.6%) | F(0.5%) | R(0.3%) |
| Q(1.4%) | I(1.8%) | C(1.6%) | C(1.4%) | D(0.5%) | W(0.3%) | Q(0.2%) |
| M(1.2%) | K(1.4%) | I(1.3%) | I(1.3%) | C(0.5%) | I(0.3%) | E(0.1%) |
| H(0.9%) | Q(1.4%) | Q(1.1%) | Q(1.1%) | H(0.5%) | K(0.1%) | W(0.1%) |
| K(0.7%) | M(1.0%) | K(1.0%) | K(0.7%) | Q(0.4%) | M(0.1%) | M(0.1%) |
| C(0.3%) | C(0.5%) | M(0.6%) | M(0.3%) | K(0.1%) | C(0.1%) | K(0.1%) |

TABLE 1g

Amino acid composition for HC-CDR3 loops of length 13 in natural antibodies. Below each loop position (top row, Kabat nomenclature, HC-CDR3 corresponds to position 95 to 102) the observed percent frequencies for each amino acid at that position are shown. Amino acids with observed frequencies less than 0.05% are not shown.

| 92 | 93 | 94 | 95 | 96 | 97 | 98 | 99 | 100 | 100a | 100b |
|---|---|---|---|---|---|---|---|---|---|---|
| C(100.0%) | A(93.2%) | R(74.2%) | D(23.7%) | G(14.2%) | G(17.0%) | G(14.3%) | G(17.4%) | G(16.8%) | G(16.7%) | Y(15.4%) |
| | T(3.6%) | K(12.3%) | G(18.9%) | R(12.9%) | S(10.0%) | S(13.4%) | S(16.1%) | S(15.2%) | S(13.5%) | G(13.4%) |
| | V(2.3%) | S(4.5%) | V(8.1%) | P(9.8%) | R(9.3%) | Y(12.1%) | Y(11.6%) | Y(12.0%) | Y(13.0%) | S(11.4%) |
| | S(0.3%) | T(3.5%) | A(7.8%) | S(8.8%) | Y(8.7%) | V(7.6%) | A(8.5%) | A(8.5%) | A(7.2%) | L(6.1%) |
| | G(0.3%) | H(1.1%) | E(7.3%) | Y(7.6%) | A(6.4%) | A(7.0%) | V(6.8%) | V(6.2%) | V(6.1%) | T(5.9%) |
| | D(0.1%) | G(1.1%) | R(5.2%) | V(6.3%) | D(6.5%) | D(5.5%) | D(6.2%) | T(6.1%) | P(5.4%) | |
| | I(0.1%) | A(0.7%) | S(5.0%) | V(5.0%) | D(5.6%) | R(5.9%) | T(4.9%) | T(5.8%) | R(5.2%) | R(5.2%) |
| | | I(0.5%) | H(5.0%) | Y(4.7%) | L(5.2%) | T(4.9%) | L(4.5%) | L(5.2%) | L(4.8%) | A(5.2%) |
| | | L(0.5%) | L(4.1%) | D(3.8%) | P(4.6%) | I(4.4%) | R(4.5%) | W(4.1%) | W(4.8%) | V(4.7%) |
| | | V(0.3%) | T(2.6%) | T(3.8%) | T(4.5%) | L(4.0%) | W(3.8%) | R(3.6%) | D(4.8%) | D(4.2%) |
| | | N(0.3%) | P(2.6%) | I(3.5%) | I(3.9%) | P(3.7%) | I(3.3%) | P(2.8%) | P(3.3%) | W(4.2%) |
| | | P(0.3%) | Q(2.4%) | E(3.3%) | E(3.4%) | W(3.0%) | F(2.3%) | I(2.5%) | I(2.5%) | N(3.3%) |
| | | E(0.3%) | I(1.5%) | Q(3.1%) | W(2.3%) | E(2.5%) | P(2.1%) | E(2.2%) | E(2.2%) | E(3.0%) |
| | | Q(0.1%) | Y(1.3%) | K(2.5%) | Q(2.2%) | F(2.3%) | Q(2.0%) | N(2.0%) | E(2.2%) | I(2.6%) |
| | | C(0.1%) | N(1.1%) | H(2.3%) | N(2.1%) | Q(2.0%) | N(1.8%) | F(1.9%) | F(2.0%) | F(2.6%) |
| | | F(0.1%) | F(0.9%) | F(2.2%) | F(2.1%) | N(1.9%) | E(1.7%) | Q(1.5%) | Q(1.4%) | H(1.9%) |
| | | Y(0.1%) | W(0.7%) | N(2.1%) | K(1.9%) | M(1.5%) | M(1.4%) | M(1.4%) | K(1.2%) | K(1.7%) |
| | | M(0.1%) | K(0.7%) | M(1.8%) | M(1.7%) | K(1.1%) | H(0.8%) | H(0.9%) | H(1.1%) | Q(1.4%) |
| | | | M(0.7%) | W(1.5%) | H(1.7%) | H(1.1%) | K(0.5%) | K(0.7%) | M(1.0%) | C(1.2%) |
| | | | C(0.4%) | C(0.7%) | C(1.1%) | C(0.8%) | C(0.5%) | C(0.3%) | C(0.6%) | M(0.9%) |

| 100c | 100d | 100e | 101 | 102 | 103 |
|---|---|---|---|---|---|
| Y(21.4%) | Y(20.4%) | F(59.3%) | D(86.4%) | Y(47.4%) | W(100.0%) |
| G(15.7%) | G(18.1%) | M(11.4%) | G(3.5%) | P(15.3%) | |
| D(9.1%) | A(13.7%) | L(8.0%) | Q(1.4%) | V(12.9%) | |
| N(8.1%) | W(12.9%) | Y(3.2%) | T(1.0%) | I(11.1%) | |
| S(7.9%) | P(6.0%) | V(3.0%) | E(0.8%) | L(3.9%) | |
| W(5.2%) | S(4.6%) | I(3.0%) | N(0.8%) | H(2.4%) | |
| R(4.3%) | L(3.6%) | P(2.3%) | Y(0.8%) | S(1.9%) | |
| T(4.1%) | V(2.8%) | G(2.0%) | V(0.8%) | F(1.2%) | |
| A(3.6%) | T(2.6%) | S(1.9%) | A(0.7%) | T(0.9%) | |
| P(3.3%) | R(2.4%) | A(0.9%) | S(0.7%) | N(0.8%) | |
| L(3.2%) | D(1.9%) | W(0.7%) | L(0.7%) | D(0.7%) | |
| V(2.6%) | F(1.9%) | T(0.7%) | P(0.6%) | C(0.4%) | |
| E(2.1%) | E(1.7%) | R(0.6%) | R(0.5%) | A(0.3%) | |
| H(2.1%) | H(1.6%) | E(0.6%) | H(0.4%) | R(0.3%) | |
| F(2.0%) | N(1.5%) | N(0.5%) | I(0.4%) | G(0.2%) | |
| I(1.4%) | I(1.2%) | D(0.5%) | F(0.2%) | Q(0.1%) | |
| C(1.2%) | C(1.1%) | H(0.5%) | K(0.1%) | E(0.1%) | |
| K(1.0%) | Q(0.9%) | C(0.4%) | W(0.1%) | M(0.1%) | |
| Q(0.9%) | K(0.6%) | Q(0.3%) | C(0.1%) | W(0.1%) | |
| M(0.7%) | M(0.3%) | K(0.1%) | | K(0.1%) | |

TABLE 1h

Amino acid composition for HC-CDR3 loops of length 14 in natural antibodies. Below each loop position (top row, Kabat nomenclature, HC-CDR3 corresponds to position 95 to 102) the observed percent frequencies for each amino acid at that position are shown. Amino acids with observed frequencies less than 0.05% are not shown.

| 92 | 93 | 94 | 95 | 96 | 97 | 98 | 99 | 100 | 100a | 100b |
|---|---|---|---|---|---|---|---|---|---|---|
| C(100.01) | A(94.0%) | R(74.6%) | D(22.4%) | G(16.3%) | G(15.3%) | G(14.8%) | G(15.9%) | G(17.2%) | G(16.0%) | Y(16.6%) |
| | T(3.1%) | K(11.2%) | G(18.8%) | R(12.2%) | S(9.9%) | Y(11.7%) | S(15.4%) | S(16.0%) | S(14.6%) | G(15.6%) |
| | V(2.2%) | S(4.6%) | E(8.1%) | P(9.2%) | Y(9.6%) | S(11.6%) | Y(12.2%) | Y(10.9%) | Y(13.5%) | S(12.6%) |
| | G(0.3%) | T(4.2%) | V(7.9%) | L(8.6%) | R(9.4%) | D(7.3%) | A(7.4%) | A(8.3%) | A(7.4%) | T(6.0%) |
| | S(0.3%) | H(1.3%) | A(7.2%) | S(8.0%) | V(6.7%) | V(6.9%) | V(6.9%) | V(7.0%) | T(6.6%) | A(6.0%) |
| | D(0.1%) | G(1.2%) | R(6.0%) | A(5.6%) | L(6.3%) | R(6.2%) | D(5.5%) | D(6.1%) | V(6.4%) | V(5.7%) |
| | I(0.1%) | A(0.7%) | H(5.0%) | Y(5.5%) | A(6.1%) | A(6.2%) | T(5.4%) | L(5.0%) | D(5.2%) | P(5.2%) |
| | | I(0.5%) | S(5.0%) | V(4.9%) | P(5.8%) | T(4.8%) | R(4.9%) | T(5.0%) | L(4.7%) | L(5.1%) |
| | | N(0.4%) | L(4.4%) | T(4.0%) | D(5.3%) | L(4.6%) | L(4.2%) | W(4.2%) | W(4.7%) | R(4.9%) |
| | | L(0.3%) | T(3.0%) | D(3.7%) | T(4.4%) | P(4.5%) | I(4.0%) | R(3.7%) | R(4.0%) | D(4.0%) |
| | | E(0.2%) | Q(2.7%) | I(3.0%) | I(4.3%) | I(3.9%) | W(3.8%) | I(2.9%) | P(2.9%) | W(3.5%) |
| | | V(0.2%) | P(2.3%) | E(3.0%) | E(2.9%) | W(3.0%) | F(2.5%) | F(2.3%) | N(2.4%) | I(2.4%) |
| | | M(0.2%) | I(1.4%) | Q(2.9%) | Q(2.5%) | E(2.4%) | P(2.2%) | P(2.2%) | I(2.2%) | E(2.4%) |
| | | Y(0.1%) | N(1.2%) | F(2.5%) | F(2.1%) | Q(2.4%) | E(2.0%) | N(2.2%) | E(2.0%) | N(2.2%) |
| | | P(0.1%) | Y(1.0%) | H(2.3%) | W(2.1%) | N(2.1%) | Q(1.8%) | E(2.0%) | F(1.9%) | F(1.9%) |
| | | Q(0.1%) | F(1.0%) | K(2.3%) | H(1.6%) | F(2.0%) | M(1.5%) | M(1.6%) | M(1.3%) | Q(1.4%) |
| | | C(0.1%) | K(0.7%) | N(2.2%) | N(1.6%) | M(1.5%) | N(1.4%) | Q(1.4%) | H(1.3%) | C(1.4%) |
| | | W(0.1%) | W(0.7%) | W(1.7%) | K(1.5%) | H(1.5%) | H(1.1%) | H(0.8%) | Q(1.2%) | K(1.2%) |
| | | | M(0.6%) | M(1.3%) | C(1.4%) | C(1.3%) | C(1.1%) | C(0.6%) | K(0.9%) | H(1.1%) |
| | | | | C(0.6%) | C(0.8%) | M(1.2%) | K(1.2%) | K(0.6%) | K(0.5%) | C(0.7%) | M(0.7%) |

| | 100c | 100d | 100e | 100f | 101 | 102 | 103 |
|---|---|---|---|---|---|---|---|
| | Y(19.4%) | Y(24.1%) | Y(21.5%) | F(60.0%) | D(88.5%) | Y(45.1%) | W(100.0%) |
| | G(12.2%) | G(14.6%) | G(19.7%) | M(14.5%) | G(2.6%) | V(15.7%) | |
| | S(10.6%) | D(9.7%) | A(14.0%) | L(7.8%) | Q(1.4%) | P(14.9%) | |
| | P(6.7%) | N(7.9%) | W(12.6%) | I(2.7%) | E(1.1%) | I(11.4%) | |
| | L(6.1%) | S(7.3%) | P(5.7%) | V(2.6%) | T(0.9%) | L(4.3%) | |
| | R(5.4%) | W(4.8%) | S(3.8%) | Y(2.2%) | A(0.8%) | H(2.4%) | |
| | T(5.3%) | R(4.4%) | L(3.6%) | P(2.1%) | H(0.7%) | S(2.0%) | |
| | A(5.0%) | P(3.6%) | V(2.5%) | S(1.8%) | N(0.7%) | F(1.3%) | |
| | V(4.1%) | A(3.3%) | T(2.3%) | G(1.5%) | R(0.6%) | T(0.6%) | |
| | D(3.9%) | T(3.0%) | R(2.1%) | A(0.8%) | Y(0.5%) | N(0.6%) | |
| | W(2.9%) | L(2.9%) | H(1.9%) | T(0.7%) | V(0.4%) | D(0.5%) | |
| | N(2.9%) | V(2.4%) | D(1.9%) | N(0.7%) | S(0.4%) | C(0.3%) | |
| | E(2.7%) | H(2.2%) | F(1.9%) | W(0.6%) | L(0.3%) | A(0.2%) | |
| | F(2.5%) | E(2.0%) | E(1.6%) | D(0.5%) | I(0.3%) | G(0.2%) | |
| | I(2.4%) | F(1.8%) | N(1.5%) | R(0.4%) | P(0.3%) | R(0.2%) | |
| | H(2.3%) | C(1.8%) | I(1.2%) | H(0.4%) | F(0.2%) | M(0.1%) | |
| | K(1.6%) | I(1.3%) | C(0.8%) | C(0.3%) | K(0.1%) | Q(0.1%) | |
| | C(1.5%) | Q(1.1%) | Q(0.7%) | E(0.3%) | W(0.1%) | W(0.1%) | |
| | Q(1.3%) | K(1.0%) | K(0.6%) | Q(0.2%) | | E(0.1%) | |
| | M(0.9%) | M(0.6%) | M(0.2%) | K(0.1%) | | | |

TABLE 1i

Amino acid composition for HC-CDR3 loops of length 15 in natural antibodies. Below each loop position (top row, Kabat nomenclature, HC-CDR3 corresponds to position 95 to 102) the observed percent frequencies for each amino acid at that position are shown. Amino acids with observed frequencies less than 0.05% are not shown.

| 92 | 93 | 94 | 95 | 96 | 97 | 98 | 99 | 100 | 100a | 100b |
|---|---|---|---|---|---|---|---|---|---|---|
| C(100.0%) | A(94.3%) | R(76.0%) | D(23.1%) | G(14.4%) | G(16.3%) | Y(13.4%) | G(15.1%) | G(16.6%) | S(17.6%) | G(17.2%) |
| | T(3.6%) | K(10.2%) | G(19.6%) | R(13.6%) | Y(11.8%) | G(12.4%) | S(14.3%) | S(16.0%) | G(16.2%) | Y(15.6%) |
| | V(1.6%) | S(4.1%) | V(7.8%) | P(9.8%) | R(9.4%) | S(11.9%) | Y(12.7%) | Y(11.3%) | Y(11.2%) | S(14.0%) |
| | S(0.2%) | T(4.0%) | E(7.8%) | L(8.4%) | S(8.6%) | D(7.3%) | V(6.9%) | V(7.5%) | V(6.6%) | T(5.6%) |
| | G(0.1%) | H(1.6%) | A(7.2%) | S(7.5%) | V(6.2%) | V(6.9%) | A(6.8%) | A(6.9%) | T(6.4%) | A(5.6%) |
| | E(0.1%) | G(1.3%) | R(5.6%) | V(5.3%) | L(5.5%) | R(6.2%) | D(6.1%) | D(6.2%) | A(6.3%) | V(5.2%) |
| | D(0.1%) | A(1.0%) | H(5.0%) | Y(5.2%) | P(5.4%) | A(5.9%) | R(5.0%) | T(5.2%) | D(5.7%) | D(5.0%) |
| | | N(0.5%) | S(5.0%) | A(5.1%) | D(5.3%) | T(5.2%) | L(4.8%) | L(5.1%) | L(5.1%) | L(4.7%) |
| | | I(0.3%) | L(4.7%) | T(3.9%) | A(5.1%) | L(5.0%) | T(4.8%) | W(4.4%) | R(4.0%) | R(4.4%) |
| | | V(0.2%) | T(2.9%) | D(3.8%) | T(4.7%) | P(5.0%) | I(4.6%) | R(4.4%) | W(4.0%) | W(3.9%) |
| | | L(0.2%) | P(2.4%) | E(3.4%) | I(4.1%) | I(4.6%) | W(3.3%) | I(3.0%) | P(3.2%) | P(3.6%) |
| | | Y(0.1%) | Q(2.4%) | Q(3.0%) | E(2.9%) | E(2.8%) | P(2.5%) | F(2.5%) | F(2.4%) | I(2.6%) |
| | | C(0.1%) | I(1.4%) | I(2.9%) | F(2.2%) | F(2.2%) | F(2.5%) | P(2.3%) | I(2.2%) | E(2.5%) |
| | | F(0.1%) | Y(1.1%) | H(2.6%) | W(1.9%) | F(2.1%) | M(2.0%) | N(1.7%) | N(2.1%) | N(2.3%) |
| | | M(0.1%) | N(0.9%) | F(2.4%) | N(1.9%) | Q(2.0%) | E(1.8%) | E(1.6%) | E(2.0%) | F(1.8%) |
| | | P(0.1%) | F(0.8%) | K(2.4%) | Q(1.8%) | C(2.0%) | N(1.7%) | Q(1.5%) | M(1.2%) | C(1.8%) |
| | | E(0.1%) | W(0.7%) | N(2.3%) | H(1.8%) | N(1.5%) | C(1.6%) | M(1.2%) | Q(1.2%) | H(1.1%) |
| | | | K(0.6%) | W(1.9%) | K(1.6%) | M(1.4%) | Q(1.6%) | C(1.1%) | C(0.8%) | Q(1.1%) |

TABLE 1i-continued

Amino acid composition for HC-CDR3 loops of length 15 in natural antibodies. Below each loop position (top row, Kabat nomenclature, HC-CDR3 corresponds to position 95 to 102) the observed percent frequencies for each amino acid at that position are shown. Amino acids with observed frequencies less than 0.05% are not shown.

| | | | | | | | |
|---|---|---|---|---|---|---|---|
| M(0.6%) | M(1.4%) | M(1.6%) | H(1.1%) | H(1.1%) | H(0.7%) | H(0.8%) | K(0.9%) |
| C(0.4%) | C(0.9%) | C(1.6%) | K(1.1%) | K(0.6%) | K(0.6%) | K(0.7%) | M(0.9%) |

| 100c | 100d | 100e | 100f | 100g | 101 | 102 | 103 |
|---|---|---|---|---|---|---|---|
| Y(20.6%) | Y(24.1%) | Y(27.8%) | G(23.4%) | F(59.8%) | D(89.9%) | Y(39.8%) | W(100.0%) |
| G(14.0%) | G(10.9%) | G(13.4%) | Y(20.2%) | M(18.3%) | G(2.3%) | V(19.9%) | |
| S(11.4%) | S(9.8%) | D(9.4%) | W(14.1%) | L(6.4%) | Q(1.5%) | P(16.2%) | |
| R(5.8%) | L(5.9%) | N(9.4%) | A(14.1%) | V(2.1%) | E(0.8%) | I(11.9%) | |
| A(5.5%) | P(5.9%) | S(6.6%) | P(5.5%) | I(2.0%) | T(0.8%) | L(4.3%) | |
| P(5.3%) | T(4.8%) | W(4.7%) | S(3.4%) | P(1.9%) | N(0.6%) | H(2.1%) | |
| T(5.0%) | R(4.7%) | R(4.1%) | L(3.0%) | Y(1.9%) | A(0.6%) | S(1.9%) | |
| L(4.9%) | A(4.2%) | P(3.7%) | T(2.1%) | G(1.6%) | H(0.6%) | F(0.9%) | |
| V(4.5%) | V(4.0%) | A(2.8%) | V(2.0%) | S(1.6%) | S(0.4%) | T(0.6%) | |
| D(3.8%) | D(3.8%) | L(2.7%) | H(1.9%) | T(0.6%) | Y(0.4%) | D(0.5%) | |
| W(2.9%) | N(3.3%) | T(2.6%) | R(1.9%) | A(0.6%) | R(0.4%) | N(0.4%) | |
| I(2.3%) | E(2.9%) | H(2.3%) | F(1.8%) | W(0.5%) | V(0.4%) | C(0.3%) | |
| E(2.2%) | W(2.7%) | V(2.0%) | D(1.4%) | N(0.5%) | F(0.3%) | R(0.3%) | |
| C(2.1%) | H(2.3%) | E(1.9%) | N(1.3%) | H(0.5%) | P(0.3%) | A(0.2%) | |
| N(2.0%) | I(2.2%) | F(1.6%) | E(1.2%) | C(0.4%) | L(0.2%) | M(0.2%) | |
| F(1.9%) | F(2.1%) | C(1.3%) | I(1.0%) | D(0.4%) | I(0.2%) | G(0.1%) | |
| H(1.7%) | K(1.9%) | K(1.0%) | C(0.6%) | R(0.4%) | K(0.1%) | Q(0.1%) | |
| K(1.6%) | C(1.8%) | Q(0.9%) | Q(0.5%) | E(0.3%) | W(0.1%) | W(0.1%) | |
| Q(1.6%) | Q(1.6%) | I(0.9%) | K(0.4%) | Q(0.2%) | M(0.1%) | K(0.1%) | |
| M(0.7%) | M(1.0%) | M(0.7%) | M(0.1%) | K(0.1%) | | | |

Example 2. Design of a Germline VH-Linker-VL Single-Chain Scaffold

Figure 3:
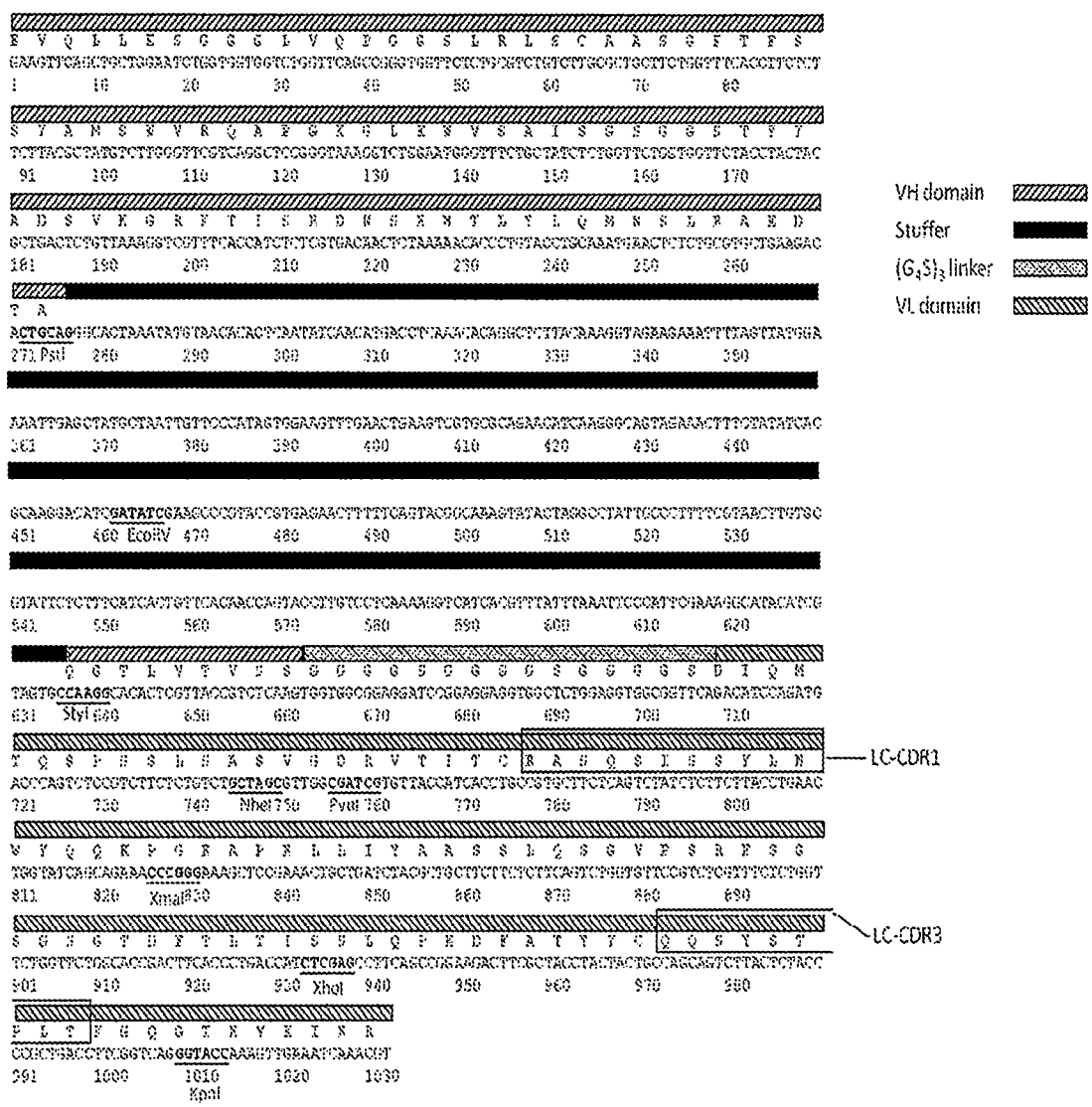
FIG. 3: Sequence of the single-chain scaffold (SEQ ID NO: 7) including the stuffer element replacing the HC-CDR3 region. Digestion with PstI/StyI removes the stuffer and allows insertion of the HC-CDR3 diversity containing oligonucleotides. Unique restriction sites are indicated underlined in the sequence. Also shown are the location of region CDR1 and CDR3 of the variable light chain.
Figure 4:
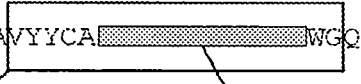
FIG. 4: Schematic view showing the heavy chain (SEQ ID NO: 1) of the single-chain scaffold after insertion of the HC-CDR3 diversity containing oligonucleotides.

Phage-displayed antibody libraries based on single-chain antibodies have been successfully generated for a large spectrum of library layouts (Mondon et al., 2008) and this format was therefore chosen as the antibody format into which to insert the HC-CDR3 diversity. The VH3/VK1 variable domain pairing is one of the most commonly observed VH/VL combinations in natural antibodies (Huang et al., 1996; de Wildt et al., 1999; DeKosky et. al., 2013). It is also observed with high frequency in a recombinant single-chain antibody library of natural variable domains (Glanville et al., 2010), has good thermal stability and is also efficiently expressed (Ewert et al., JMB 2003). For the assembly of a VH3/VK1 single-chain scaffold, human germline antibody sequences were selected because germline sequences have favorable properties such as absence of somatic mutations that might cause immunogenicity when present in a therapeutic antibody and an intrinsic tolerance towards the presence of diverse HC-CDR3 regions. The heavy chain variable domain scaffold amino acid sequence was assembled from the translated Genbank germline sequence M99660 (SEQ ID 1) and the translated Genbank germline sequence J00256 (J4 fragment) (SEQ ID 2). In the scaffold the HC-CDR3 region including few flanking amino acids is represented by a stuffer fragment containing a unique EcoRV site that allows removing of uncleaved vector during library cloning (FIG. 3). The stuffer fragment contains a PstI site at its 5' end and a StyI site at its 3' end allowing excision of the fragment during library generation and cloning of the HC-CDR3 diversity encoding oligonucleotides (FIG. 4). PstI (CTGCAG) and StyI (CCWWGG) were chosen because only few combinations of codon-encoding trimer blocks (FIG. 5), used to synthesize the HC-CDR3 diversity encoding oligonucleotides, generate PstI and StyI recognition sites. His and Gln trimer blocks (CAT and CAG) were therefore subsequently excluded from the design of the HC-CDR3 diversity encoding oligonucleotides. The light chain variable domain amino acid scaffold sequence was assembled from the translated Genbank germline sequence X93627 (SEQ ID 3) and Genbank germline sequence J00242 (VK-1 J1 fragment) (SEQ ID 4). The length of the LC-CDR3 loop was chosen to be 9 amino acids, the most frequently observed length in VH3/VK1 heavy chain/light chain combinations in natural antibodies (DeKosky et. al. 2013). The amino acid sequence of the LC-CDR3 loop is represented by the most frequently observed amino acids in LC-CDR3 loops of length 9 in VH3/VK1 combinations (SEQ ID 5). In the amino acid sequence of the LC-CDR3 loop the initial codon from the VK-1 J1 fragment (TGG) encoding a Trp was substituted by CTG (Leu), the most frequently observed amino acid at this position in LC-CDR3 loops of length 9 in natural antibodies with VH3/VK1 combinations (DeKosky et. al. 2013). Additional unique restriction sites were introduced up- and down-stream of the light chain LC-CDR1 and LC-CDR3 region (FIG. 3). A single-chain scaffold was then assembled into a VH/VL single-chain topology by a connecting GGGGSGGGGSGGGGS linker (SEQ ID 6) (FIG. 3), undesired restriction sites were removed by choosing alternative codons and the resulting nucleotide sequence was codon-optimized for expression in E. coli (SEQ ID 7).

Figure 6:
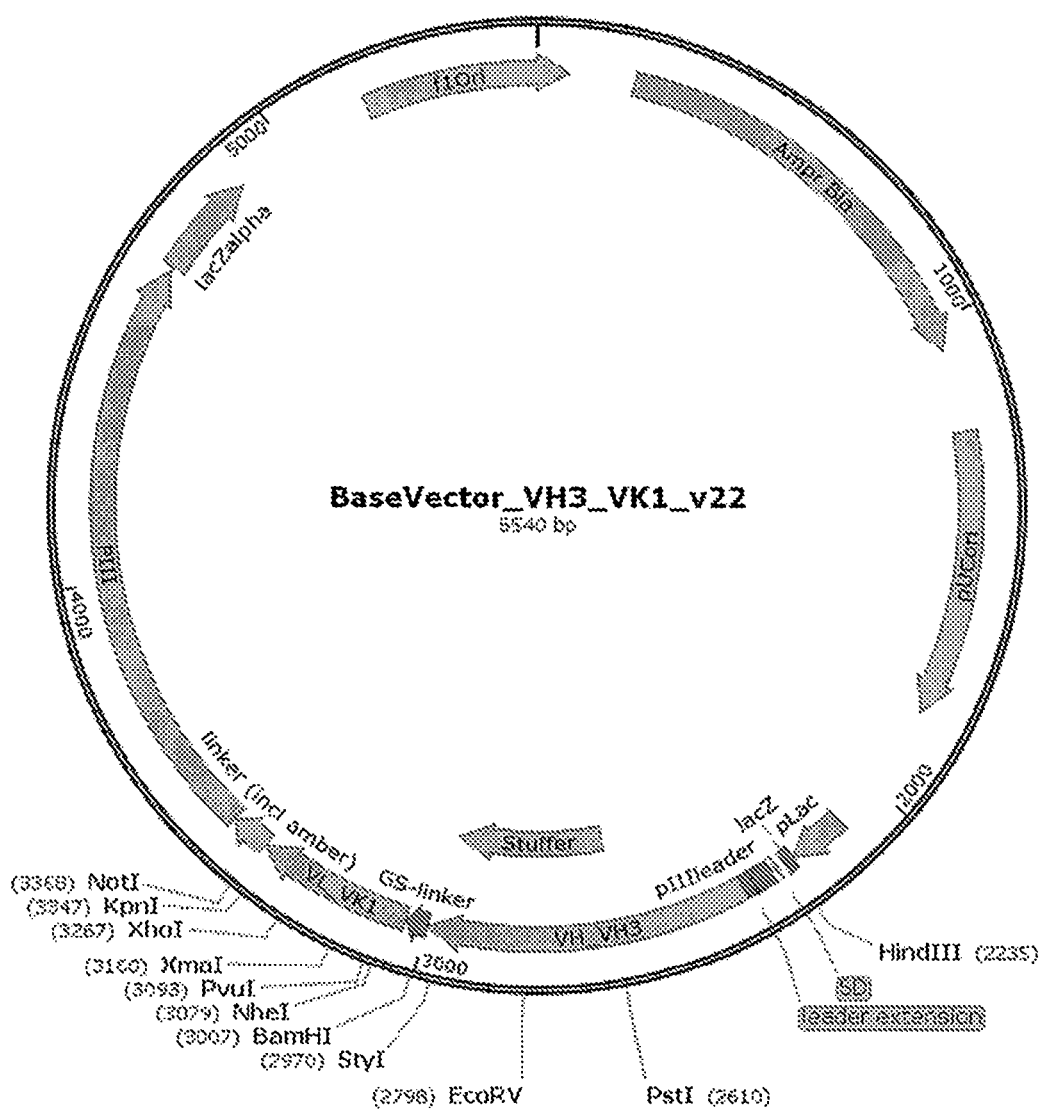
FIG. 6: Schematic view of the phagemid vector BaseVector_VH3_VK1_v22

Example 3. Design and Generation of the Display Vector BaseVector_VH3_VK1_v22 Allowing Generation of a Single-Chain HC-CDR3-Only Library The phage display vector for library construction is based on the pCANTAB6 vector, a derivative of the pCANTAB5 vector (McCafferty et al. 1994). The sequence of pCANTAB6 was re-constructed starting from Genbank entry U14321 introducing the modifications outlined in McCafferty et al. 1994. The scFv cloning site of pCANTAB6 was replaced by the VH3-linker-VK1 single-chain scaffold including the stuffer segment (FIG. 6). Introduction of a few single base substitutions to remove undesired restriction sites and restoration of the replication origin sequence listed below thus yielded the sequence of the BaseVector_VH3_VK1_v22 (SEQ ID 8).

Composition of display vector BaseVector_VH3_VK1_v22:

Position 1 to 2334: from U14321 with the following modifications:
- 320 C->T removes XhoI site
- 617 G->C removes PvuI site
- 1379 T->C makes sequence of replication original identical to other phagemid vectors
- 2328 C->G removes StyI site Position 2335 to 3366: VH3-linker-VK1 single-chain scaffold (SEQ ID 7).

Position 3367 to 3447: Segment connecting the C-terminus of the light chain variable domain with the pIII protein as shown in McCafferty et al. 1994

Figure 7:
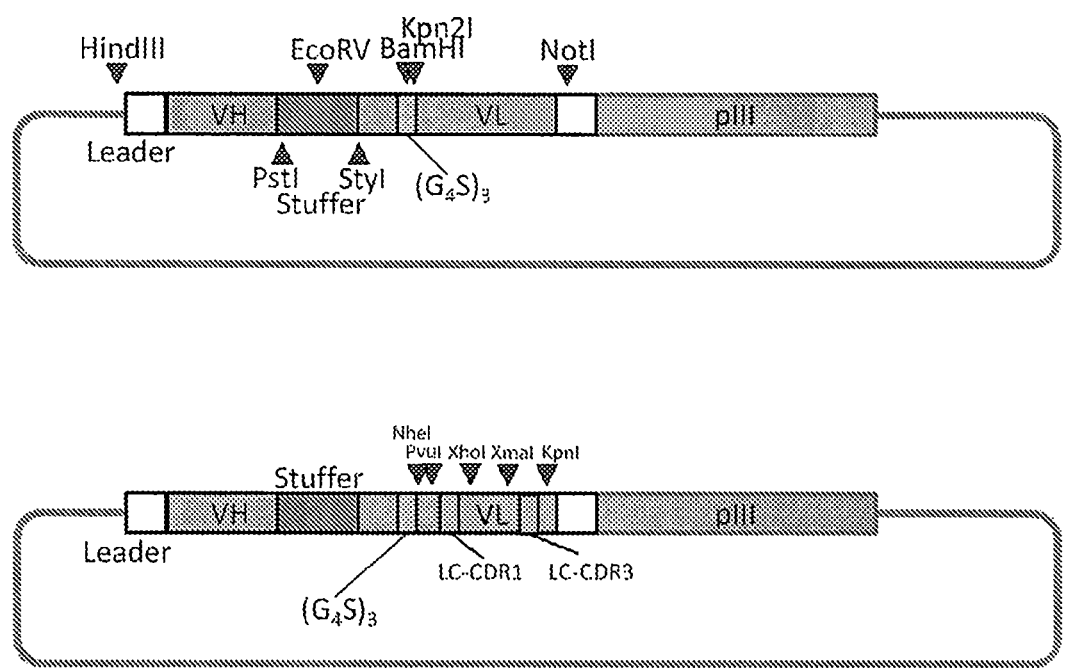
FIG. 7: Schematic view of the phagemid vector BaseVector_VH3_VK1_v22 with unique restriction sites indicated.

Position 3448 to 5540: from U14321 with the following modifications:
- 4029 G->A removes BamHI site
- 4788 A->C removes PvuI site A schematic layout of BaseVector_VH3_VK1_v22 with the inserted single-chain scaffold is shown in FIG. 6. Excision of the stuffer region with PstI and StyI allows cloning of oligonucleotides encoding the HC-CDR3 diversity. Additional unique restriction sites allow excision of the complete single-chain antibody, the individual variable light or heavy chains or introduction of additional diversity in the variable light chain domain (FIG. 7). BaseVector_VH3_VK1_v22 was then synthesized and assembled by standard methods (Genscript Corporation).

Example 4. Optimization of the HC-CDR3 Loop Length Distribution and Optimization of the Position-Wise Amino Acid Diversity Within Each HC-CDR3 Loop His and Gln were excluded from the HC-CDR3 diversity design in order to exclude generation of PstI and StyI sites within the HC-CDR3 loop by the His and Gln trimer-blocks. This exclusion was acceptable because the composition of natural antibody HC-CDR3 sequences revealed that His and Gln are generally observed with only small frequencies (Tables 1a-1i). Cys was excluded at any HC-CDR3 loop position in order to avoid formation of intermolecular disulfide bridges through unpaired Cys residues. Met, prone to oxidation, was also excluded at any of the positions. Met is generally present at only very low frequencies in natural HC-CDR3 sequences (Tables 1a-1i), except for the position preceding position 101. Position 101 was always kept fixed as Asp.

The design of the HC-CDR3 loop diversity for loop lengths 7 to 15 (loop length distribution and position-wise amino acid variability) was optimized using a spreadsheet application. In the application the percent fraction for each HC-CDR3 loop length within the library and the variability (number of different amino acids) at each of the HC-CDR3 positions (including also Pos 94 preceding the HC-CDR3 loop) for each HC-CDR3 loop length can be adjusted. The application then calculates, for each HC-CDR3 loop length, the theoretically possible number of variants, the number of clones actually present (=percent fraction of a particular HC-CDR3 loop length times the total complexity of library), the Poisson estimate for the fraction of all theoretically possible variants actually present, the actual number of different variants present according to the Poisson estimate and the redundancy (number of times each variant is present on average).

Poisson estimate: $1-e^{(-1*N/M)}$

Figure 9:
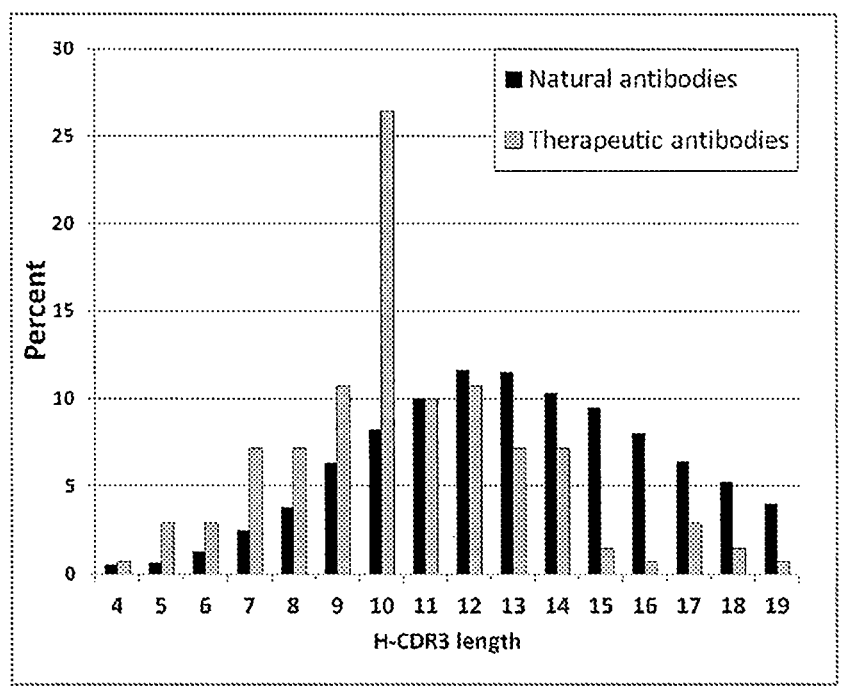
FIG. 9: Comparison of HC-CDR3 loop length distribution in approved or clinically developed therapeutic antibodies and natural antibodies. The percent values for natural antibodies have been re-normalized (to 100% total) in the length range 4 to 19.

Where
N=number of clones with a HC-CDR3 loop of length L in a library of complexity C
M=number of theoretically possible variants for a HC-CDR3 loop of length L with a particular composition of amino acids at each loop position Initially the number of different amino acids at each HC-CDR3 loop position was set to 16 (all amino acids except Cys, Gln, His and Met) except for positions 101 and 102 (5 and 8 different amino acids, respectively) and the initial percent fractions for each HC-CDR3 loop length was the HC-CDR3 loop length distribution observed in natural antibodies for loop lengths 7 to 15, re-normalized to 100%. In this configuration shorter HC-CDR3 loops are overrepresented and for HC-CDR3 loop lengths 10 to 15 less than 1% of the theoretically possibly variants are present in the library (Table 2A). For HC-CDR3 loops of length 10, enriched in therapeutic antibodies or antibodies in clinical development (FIG. 8-9) only a very small fraction of all possible variants are actually present in the library.

TABLE 2A

Design scheme for a HC-CDR3-only library of total complexity 1.3 × 10$^{10}$ with a HC-CDR3 loop length distribution like in natural amino acids, with 16 different amino acids at the hypervariable positions, 5 different amino acids at position 101 and 8 different amino acids at position 102. Positions considered hypervariable have the number of different amino acids underlined. Kabat position 94 is not varied.

| CDR3H length L | percent fraction p(L) | numer of different amino acids at hypervariable positions | Pos 93 | Pos 94 | Pos 95 | Pos 96 | Pos 97 | Pos 98 | Pos 99 | Pos 100 | Pos 100a | Pos 100b | Pos 100c |
|---|---|---|---|---|---|---|---|---|---|---|---|---|---|
| 7  | 3.3  | 16 | 1 | 1 | <u>16</u> | <u>16</u> | <u>16</u> | <u>16</u> | <u>16</u> |    |    |    |    |
| 8  | 5.1  | 16 | 1 | 1 | <u>16</u> | <u>16</u> | <u>16</u> | <u>16</u> | <u>16</u> | <u>16</u> |    |    |    |
| 9  | 8.6  | 15 | 1 | 1 | <u>16</u> | <u>16</u> | <u>16</u> | <u>16</u> | <u>16</u> | <u>16</u> | <u>16</u> |    |    |
| 10 | 11.2 | 15 | 1 | 1 | <u>16</u> | <u>16</u> | <u>16</u> | <u>16</u> | <u>16</u> | <u>16</u> | <u>16</u> | <u>16</u> |    |
| 11 | 13.6 | 14 | 1 | 1 | <u>16</u> | <u>16</u> | <u>16</u> | <u>16</u> | <u>16</u> | <u>16</u> | <u>16</u> | <u>16</u> | <u>16</u> |
| 12 | 15.8 | 13 | 1 | 1 | <u>16</u> | <u>16</u> | <u>16</u> | <u>16</u> | <u>16</u> | <u>16</u> | <u>16</u> | <u>16</u> | <u>16</u> |
| 13 | 15.6 | 11 | 1 | 1 | <u>16</u> | <u>16</u> | <u>16</u> | <u>16</u> | <u>16</u> | <u>16</u> | <u>16</u> | <u>16</u> | <u>16</u> |

TABLE 2A-continued

Design scheme for a HC-CDR3-only library of total complexity 1.3 × 10¹⁰ with a HC-CDR3 loop length distribution like in natural amino acids, with 16 different amino acids at the hypervariable positions, 5 different amino acids at position 101 and 8 different amino acids at position 102. Positions considered hypervariable have the number of different amino acids underlined. Kabat position 94 is not varied.

| | | | | | | | | | | | |
|---|---|---|---|---|---|---|---|---|---|---|---|
| 14 | 14.0 | 9 | 1 | 1 | <u>16</u> | <u>16</u> | <u>16</u> | <u>16</u> | <u>16</u> | <u>16</u> | <u>16</u> | <u>16</u> |
| 15 | 12.8 | 8 | 1 | 1 | <u>16</u> | <u>16</u> | <u>16</u> | <u>16</u> | <u>16</u> | <u>16</u> | <u>16</u> | <u>16</u> |

| CDR3H length L | Pos 100d | Pos 100e | Pos 100f | Pos 100g | Pos 101 | Pos 102 | Number of theoretically possible variants | Actual number of clones present | Fraction of theoretically possible variants actually present (Poisson estimate) | Actual number of variants present (Poisson estimate) | Redundancy (number of times each variant is present) |
|---|---|---|---|---|---|---|---|---|---|---|---|
| 7 | | | | | 5 | 8 | 4.19E+07 | 4.32E+08 | 100.0% | 4.19E+07 | 10.3 |
| 8 | | | | | 5 | 8 | 6.71E+08 | 6.60E+08 | 62.6% | 4.20E+08 | 1.6 |
| 9 | | | | | 5 | 8 | 1.07E+10 | 1.12E+09 | 9.9% | 1.06E+09 | 1.1 |
| 10 | | | | | 5 | 8 | 1.72E+11 | 1.45E+09 | 0.8% | 1.45E+09 | 1.0 |
| 11 | | | | | 5 | 8 | 2.75E+12 | 1.76E+09 | 0.1% | 1.76E+09 | 1.0 |
| 12 | <u>16</u> | | | | 5 | 8 | 4.40E+13 | 2.06E+09 | 0.005% | 2.06E+09 | 1.0 |
| 13 | <u>16</u> | <u>16</u> | | | 5 | 8 | 7.04E+14 | 2.03E+09 | 0.00029% | 2.03E+09 | 1.0 |
| 14 | <u>16</u> | <u>16</u> | <u>16</u> | | 5 | 8 | 1.13E+16 | 1.82E+09 | 0.00002% | 1.82E+09 | 1.0 |
| 15 | <u>16</u> | <u>16</u> | <u>16</u> | <u>16</u> | 5 | 8 | 1.80E+17 | 1.67E+09 | 0.000001% | 1.67E+09 | 1.0 |

Reducing the number of different amino acids from 16 to 8 at the hypervariable positions generates a library where HC-CDR3 loop lengths up to 11 are well represented, however at the same time the redundancy (the average number of times a variant is present) is strongly enhanced (Table 2B).

TABLE 2B

Design scheme for a HC-CDR3-only library of total complexity 1.3 × 10¹⁰ with a HC-CDR3 loop length distribution like in natural amino acids, with 8 different amino acids at the hypervariable positions, a constant amino acid at position 101 and 8 different amino acids at position 102. Positions considered hypervariable have the number of different amino acids underlined. Kabat position 94 is not varied.

| CDR3H length L | percent fraction p(L) | numer of different amino acids at hyper-variable positions | Pos 93 | Pos 94 | Pos 95 | Pos 96 | Pos 97 | Pos 98 | Pos 99 | Pos 100 | Pos 100a | Pos 100b | Pos 100c |
|---|---|---|---|---|---|---|---|---|---|---|---|---|---|
| 7 | 3.3 | 16 | 1 | 1 | <u>8</u> | <u>8</u> | <u>8</u> | <u>8</u> | <u>8</u> | | | | |
| 8 | 5.1 | 16 | 1 | 1 | <u>8</u> | <u>8</u> | <u>8</u> | <u>8</u> | <u>8</u> | <u>8</u> | | | |
| 9 | 8.6 | 15 | 1 | 1 | <u>8</u> | <u>8</u> | <u>8</u> | <u>8</u> | <u>8</u> | <u>8</u> | <u>8</u> | | |
| 10 | 11.2 | 15 | 1 | 1 | <u>8</u> | <u>8</u> | <u>8</u> | <u>8</u> | <u>8</u> | <u>8</u> | <u>8</u> | <u>8</u> | |
| 11 | 13.6 | 14 | 1 | 1 | <u>8</u> | <u>8</u> | <u>8</u> | <u>8</u> | <u>8</u> | <u>8</u> | <u>8</u> | <u>8</u> | <u>8</u> |
| 12 | 15.8 | 13 | 1 | 1 | <u>8</u> | <u>8</u> | <u>8</u> | <u>8</u> | <u>8</u> | <u>8</u> | <u>8</u> | <u>8</u> | <u>8</u> |
| 13 | 15.6 | 11 | 1 | 1 | <u>8</u> | <u>8</u> | <u>8</u> | <u>8</u> | <u>8</u> | <u>8</u> | <u>8</u> | <u>8</u> | <u>8</u> |
| 14 | 14.0 | 9 | 1 | 1 | <u>8</u> | <u>8</u> | <u>8</u> | <u>8</u> | <u>8</u> | <u>8</u> | <u>8</u> | <u>8</u> | <u>8</u> |
| 15 | 12.8 | 8 | 1 | 1 | <u>8</u> | <u>8</u> | <u>8</u> | <u>8</u> | <u>8</u> | <u>8</u> | <u>8</u> | <u>8</u> | <u>8</u> |

| CDR3H length L | Pos 100d | Pos 100e | Pos 100f | Pos 100g | Pos 101 | Pos 102 | Number of theoretically possible variants | Actual number of clones present | Fraction of theoretically possible variants actually present (Poisson estimate) | Actual number of variants present (Poisson estimate) | Redundancy (number of times each variant is present) |
|---|---|---|---|---|---|---|---|---|---|---|---|
| 7 | | | | | 1 | 8 | 2.62E+05 | 4.32E+08 | 100.0% | 2.62E+05 | 1648.1 |
| 8 | | | | | 1 | 8 | 2.10E+06 | 5.60E+08 | 100.0% | 2.10E+06 | 314.8 |
| 9 | | | | | 1 | 8 | 1.68E+07 | 1.12E+09 | 100.0% | 1.68E+07 | 66.5 |
| 10 | | | | | 1 | 8 | 1.34E+08 | 1.45E+09 | 100.0% | 1.34E+08 | 10.8 |
| 11 | | | | | 1 | 8 | 1.07E+09 | 1.76E+09 | 80.7% | 8.66E+08 | 2.0 |
| 12 | <u>8</u> | | | | 1 | 8 | 8.59E+09 | 2.06E+09 | 21.30% | 1.83E+09 | 1.1 |
| 13 | <u>8</u> | <u>8</u> | | | 1 | 8 | 6.87E+10 | 2.03E+09 | 2.91250% | 2.00E+09 | 1.0 |

TABLE 2B-continued

Design scheme for a HC-CDR3-only library of total complexity $1.3 \times 10^{10}$ with a HC-CDR3 loop length distribution like in natural amino acids, with 8 different amino acids at the hypervariable positions, a constant amino acid at position 101 and 8 different amino acids at position 102. Positions considered hypervariable have the number of different amino acids underlined. Kabat position 94 is not varied.

| 14 | <u>8</u> | <u>8</u> | <u>8</u> |   | 1 | 8 | 5.50E+11 | 1.82E+09 | 0.33006% | 1.81E+09 | 1.0 |
| 15 | <u>8</u> | <u>8</u> | <u>8</u> | <u>8</u> | 1 | 8 | 4.40E+12 | 1.67E+09 | 0.037941% | 1.67E+09 | 1.0 |

Figure 10:
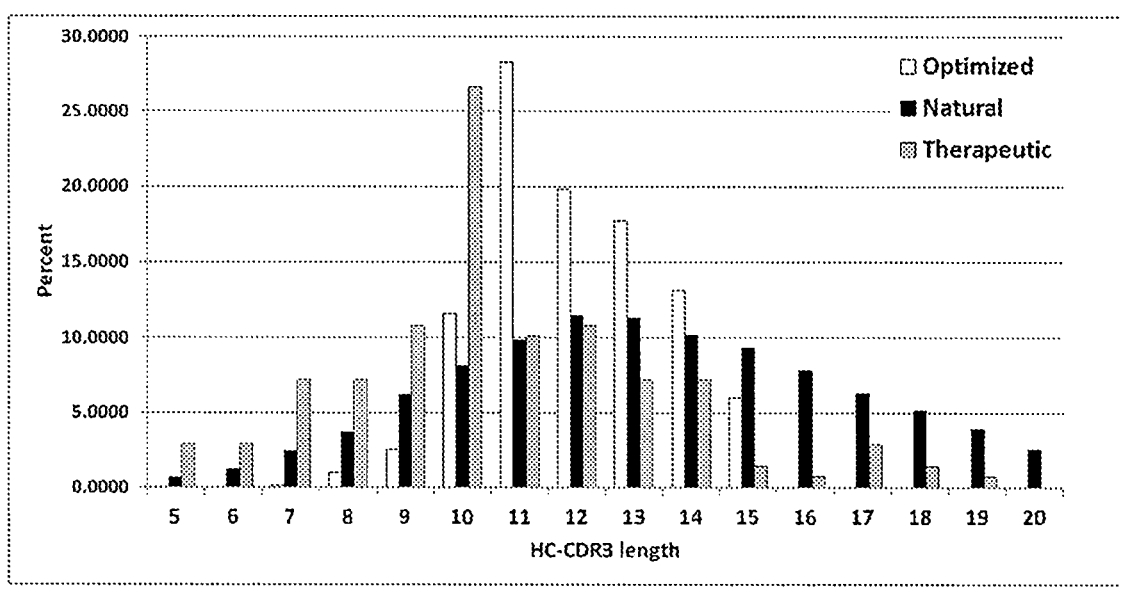
FIG. 10: Comparison of HC-CDR3 loop length distribution in approved or clinically developed therapeutic antibodies, natural antibodies and the loop length distribution in the optimized library design. The percent values for natural antibodies have been re-normalized (to 100% total) in the length range 5 to 19.

Adjusting the percent values for the HC-CDR3 loop length distribution, introducing additional variability at position 94 for HC-CDR3 loop lengths 7 to 11, gradually reducing the number of different amino acids present at the hypervariable positions for longer HC-CDR3 loops and reducing the number of different amino acids at position 102 and the position preceding position 101 provides a library design with favorable properties (Table 2C). Redundancy is considerably reduced for short HC-CDR3 loops, coverage of variants for loop lengths 9 to 11 is high and longer HC-CDR3 loops are also represented relatively well (Table 2C). The optimized HC-CDR3 loop length distribution is shown in FIG. 10 together with the HC-CDR3 loop length distribution observed in natural antibodies and that for therapeutic antibodies already approved or in clinical development.

TABLE 2C

Design scheme for a HC-CDR3-only library of total complexity $1.3 \times 10^{10}$ with an optimized HC-CDR3 loop length distribution and with optimized variability at Kabat position 94 and at each position of each HC-CDR3 loop. Positions considered hypervariable have the number of different amino acids underlined.

| CDR3H length L | percent fraction p(L) | numer of different amino acids at hypervariable positions | Pos 93 | Pos 94 | Pos 95 | Pos 96 | Pos 97 | Pos 98 | Pos 99 | Pos 100 | Pos 100a | Pos 100b | Pos 100c | Pos 100d | Pos 100e |
|---|---|---|---|---|---|---|---|---|---|---|---|---|---|---|---|
| 7 | 0.1 | 16 | 1 | 3 | 10 | <u>16</u> | <u>16</u> | <u>16</u> | <u>16</u> | | | | | |
| 8 | 1.0 | 16 | 1 | 3 | 9 | <u>16</u> | <u>16</u> | <u>16</u> | <u>16</u> | <u>16</u> | | | | |
| 9 | 2.5 | 15 | 1 | 3 | 8 | <u>15</u> | <u>15</u> | <u>15</u> | <u>15</u> | <u>15</u> | 4 | | | |
| 10 | 11.5 | 15 | 1 | 2 | 7 | <u>15</u> | <u>15</u> | <u>15</u> | <u>15</u> | <u>15</u> | <u>15</u> | 3 | | |
| 11 | 28.3 | 14 | 1 | 2 | 6 | <u>14</u> | <u>14</u> | <u>14</u> | <u>14</u> | <u>14</u> | <u>14</u> | <u>14</u> | 3 | |
| 12 | 19.8 | 13 | 1 | 1 | 5 | <u>13</u> | <u>13</u> | <u>13</u> | <u>13</u> | <u>13</u> | <u>13</u> | <u>13</u> | <u>13</u> | 2 |
| 13 | 17.7 | 11 | 1 | 1 | 4 | <u>11</u> | <u>11</u> | <u>11</u> | <u>11</u> | <u>11</u> | <u>11</u> | <u>11</u> | <u>11</u> | 1 |
| 14 | 13.1 | 9 | 1 | 1 | 3 | <u>9</u> | <u>9</u> | <u>9</u> | <u>9</u> | <u>9</u> | <u>9</u> | <u>9</u> | <u>9</u> | <u>9</u> |
| 15 | 6.0 | 8 | 1 | 1 | 2 | <u>8</u> | <u>8</u> | <u>8</u> | <u>8</u> | <u>8</u> | <u>8</u> | <u>8</u> | <u>8</u> | <u>8</u> |

| CDR3H length L | Pos 100f | Pos 100g | Pos 101 | Pos 102 | Number of theoretically possible variants | Actual number of clones present | Fraction of theoretically possible variants actually present (Poisson estimate) | Actual number of variants present (Poisson estimate) | Redundancy (number of times each variant is present) |
|---|---|---|---|---|---|---|---|---|---|
| 7 | | | 1 | 4 | 7.86E+06 | 1.30E+07 | 80.9% | 6.36E+06 | 2.0 |
| 8 | | | 1 | 4 | 1.13E+08 | 1.30E+08 | 68.3% | 7.73E+07 | 1.7 |
| 9 | | | 1 | 4 | 2.92E+08 | 3.25E+08 | 67.2% | 1.96E+08 | 1.7 |
| 10 | | | 1 | 3 | 1.44E+09 | 1.50E+09 | 64.8% | 9.31E+08 | 1.6 |
| 11 | | | 1 | 2 | 7.59E+09 | 3.68E+09 | 38.4% | 2.92E+09 | 1.3 |
| 12 | | | 1 | 1 | 8.16E+09 | 2.57E+09 | 27.1% | 2.21E+09 | 1.2 |
| 13 | | | 1 | 1 | 9.43E+09 | 2.30E+09 | 21.6% | 2.04E+09 | 1.1 |
| 14 | 1 | | 1 | 1 | 1.05E+10 | 1.70E+09 | 15.0% | 1.57E+09 | 1.1 |
| 15 | <u>8</u> | 1 | 1 | 1 | 1.72E+10 | 7.80E+08 | 4.4% | 7.63E+08 | 1.0 |

Example 5. Design of Oligonucleotides According to the Optimized Library Design

The amino acid composition for each HC-CDR3 loop length was compiled based on the optimized library design shown in table 2C. At each position and for each HC-CDR3 loop length the number of amino acids present in Table 2C were selected from the most frequently observed amino acids in natural antibodies for that HC-CDR3 loop length and position according to Tables 1a-1i and the percent values were re-normalized to 100. Amino acid composition and percent frequencies for HC-CDR3 lengths 7 to 15 according to the optimized library design are shown in tables 3A-3I. For example, for HC-CDR3 loop length 7 Table 2C indicates that 3 different amino acids should be present at position 94. The 3 most frequently observed amino acids in natural HC-CDR3 loops of length 7 are Arg 63.4%, Ser 8.9% and Thr 7.3% (Table 1a). Re-normalized to 100% the percent values for these amino acids become Arg 79.6%, Ser 11.2% and Thr 9.2%.

TABLE 3A

Optimized library amino acid composition for the HC-CDR3 loop with length L = 7. For each position the different amino acids present are shown together with their relative frequencies. To increase overall variability also position 94 preceding the HC-CDR3 loop has been varied for HC-CDR3 loop length 7.

| 92 | 93 | 94 | 95 | 96 | 97 | 98 | 99 | 101 | 102 | 103 |
|---|---|---|---|---|---|---|---|---|---|---|
| C(100.0%) | A(100.0%) | R(79.6%) | G(30.0%) | G(16.6%) | G(22.9%) | G(19.4%) | F(27.6%) | D(100.0%) | Y(68.0%) | W(100.0%) |
| | | S(11.2%) | D(18.3%) | R(11.5%) | S(12.2%) | S(14.1%) | L(15.4%) | | V(12.6%) | |
| | | T(9.2%) | E(8.3%) | D(11.2%) | D(10.1%) | A(12.0%) | G(8.5%) | | P(12.0%) | |
| | | | W(8.2%) | S(10.9%) | Y(7.7%) | Y(11.8%) | S(7.8%) | | I(7.4%) | |
| | | | R(7.2%) | L(7.2%) | R(7.2%) | W(5.4%) | V(6.1%) | | | |
| | | | V(7.1%) | A(6.3%) | A(6.4%) | T(5.1%) | Y(6.0%) | | | |
| | | | A(6.5%) | V(5.6%) | T(5.5%) | V(4.9%) | I(5.0%) | | | |
| | | | L(6.0%) | P(5.3%) | V(5.2%) | R(4.5%) | P(4.5%) | | | |
| | | | S(5.2%) | T(4.5%) | N(4.0%) | P(4.5%) | A(4.2%) | | | |
| | | | Y(3.2%) | Y(4.4%) | P(4.0%) | L(4.0%) | D(3.1%) | | | |
| | | | | N(3.5%) | L(3.9%) | D(3.8%) | T(2.8%) | | | |
| | | | | E(3.3%) | E(3.5%) | N(3.0%) | N(2.5%) | | | |
| | | | | W(3.0%) | W(3.4%) | E(2.8%) | R(2.1%) | | | |
| | | | | K(2.6%) | I(1.7%) | F(1.9%) | W(1.8%) | | | |
| | | | | F(2.2%) | F(1.6%) | I(1.7%) | E(1.8%) | | | |
| | | | | I(1.9%) | K(0.7%) | K(1.1%) | K(0.7%) | | | |

TABLE 3B

Optimized library amino acid composition for the HC-CDR3 loop with length L = 8. For each position the different amino acids present are shown together with their relative frequencies. To increase overall variability also position 94 preceding the HC-CDR3 loop has been varied for HC-CDR3 loop length 8.

| 92 | 93 | 94 | 95 | 96 | 97 | 98 | 99 | 100 | 101 | 102 | 103 |
|---|---|---|---|---|---|---|---|---|---|---|---|
| C(100.0%) | A(100.0%) | R(84.1%) | G(25.5%) | G(15.3%) | G(21.7%) | G(26.8%) | G(17.5%) | F(36.1%) | D(100.0%) | Y(71.5%) | W(100.0%) |
| | | T(8.2%) | D(24.1%) | S(11.9%) | S(15.3%) | S(12.7%) | A(14.3%) | L(11.0%) | | P(10.6%) | |
| | | S(7.8%) | E(10.5%) | R(11.6%) | A(7.8%) | Y(10.3%) | Y(13.2%) | G(7.4%) | | I(9.3%) | |
| | | | V(9.3%) | L(9.0%) | R(7.4%) | D(7.5%) | S(10.5%) | Y(6.9%) | | V(8.6%) | |
| | | | A(7.4%) | V(6.5%) | Y(6.7%) | A(6.9%) | W(6.9%) | S(5.6%) | | | |
| | | | S(6.9%) | A(6.3%) | D(6.6%) | R(6.1%) | L(5.6%) | I(5.6%) | | | |
| | | | R(6.8%) | D(6.2%) | V(5.6%) | T(5.4%) | T(5.5%) | V(5.5%) | | | |
| | | | L(6.0%) | P(6.0%) | T(5.4%) | W(4.5%) | V(4.5%) | P(4.6%) | | | |
| | | | T(3.5%) | Y(5.6%) | L(4.6%) | N(4.3%) | D(4.5%) | A(4.1%) | | | |
| | | | | T(5.5%) | E(3.8%) | L(3.7%) | R(4.0%) | T(3.6%) | | | |
| | | | | E(3.5%) | N(3.5%) | V(3.7%) | P(3.3%) | D(2.2%) | | | |
| | | | | I(3.4%) | P(3.2%) | E(2.7%) | N(2.6%) | N(2.2%) | | | |
| | | | | W(2.5%) | W(2.9%) | P(1.7%) | E(2.4%) | W(2.0%) | | | |
| | | | | N(2.4%) | I(2.6%) | F(1.5%) | F(2.1%) | E(1.8%) | | | |
| | | | | F(2.2%) | F(1.6%) | I(1.4%) | I(2.0%) | R(0.8%) | | | |
| | | | | K(2.2%) | K(1.5%) | K(0.6%) | K(1.1%) | K(0.5%) | | | |

TABLE 3C

Optimized library amino acid composition for the HC-CDR3 loop with length L = 9. For each position the different amino acids present are shown together with their relative frequencies. To increase overall variability also position 94 preceding the HC-CDR3 loop has been varied for HC-CDR3 loop length 9.

| 92 | 93 | 94 | 95 | 96 | 97 | 98 | 99 | 100 |
|---|---|---|---|---|---|---|---|---|
| C(100.0%) | A(100.0%) | R(85.7%) | G(26.3%) | G(19.8%) | G(19.9%) | G(18.6%) | G(21.6%) | G(17.4%) |
| | | S(7.5%) | D(21.5%) | R(11.1%) | S(13.8%) | S(15.5%) | Y(12.5%) | A(13.7%) |

TABLE 3C-continued

Optimized library amino acid composition for the HC-CDR3 loop with length L = 9. For each position the different amino acids present are shown together with their relative frequencies. To increase overall variability also position 94 preceding the HC-CDR3 loop has been varied for HC-CDR3 loop length 9.

| | | | | | | | |
|---|---|---|---|---|---|---|---|
| | K(6.8%) | E(10.5%) | S(10.9%) | A(8.0%) | A(9.4%) | S(11.5%) | Y(12.8%) |
| | | V(9.6%) | P(7.3%) | R(7.8%) | Y(8.8%) | A(8.4%) | S(9.9%) |
| | | A(9.3%) | L(7.0%) | Y(7.4%) | L(6.8%) | D(8.2%) | W(8.3%) |
| | | R(8.8%) | D(6.7%) | V(7.0%) | V(5.9%) | T(5.8%) | P(7.0%) |
| | | S(7.6%) | V(6.2%) | T(6.5%) | D(5.8%) | R(5.6%) | T(5.0%) |
| | | L(6.6%) | A(5.9%) | P(5.5%) | R(5.7%) | W(5.3%) | L(4.9%) |
| | | | Y(5.7%) | D(5.4%) | T(5.3%) | N(5.1%) | D(4.6%) |
| | | | T(4.8%) | L(4.4%) | W(4.1%) | L(4.9%) | V(4.3%) |
| | | | I(3.7%) | I(3.3%) | P(3.7%) | V(3.5%) | R(3.2%) |
| | | | E(3.6%) | E(3.2%) | E(3.3%) | E(2.5%) | E(2.8%) |
| | | | K(2.6%) | W(3.0%) | N(2.6%) | P(2.2%) | N(2.4%) |
| | | | N(2.5%) | F(2.5%) | F(2.3%) | F(1.7%) | F(1.9%) |
| | | | W(2.2%) | N(2.3%) | I(2.3%) | K(1.3%) | I(1.7%) |

| | 100A | 101 | 102 | 103 |
|---|---|---|---|---|
| | F(65.4%) | D(100.0%) | Y(70.1%) | W(100.0%) |
| | L(16.9%) | | P(11.6%) | |
| | Y(9.0%) | | I(9.4%) | |
| | I(8.8%) | | V(8.8%) | |

TABLE 3D

Optimized library amino acid composition for the HC-CDR3 loop with length L = 10. For each position the different amino acids present are shown together with their relative frequencies. To increase overall variability also position 94 preceding the HC-CDR3 loop has been varied for HC-CDR3 loop length 10.

| 92 | 93 | 94 | 95 | 96 | 97 | 98 | 99 | 100 | 100A |
|---|---|---|---|---|---|---|---|---|---|
| C(100.0%) | A(100.0%) | R(90.7%) | G(25.6%) | G(17.3%) | G(19.1%) | G(19.1%) | G(18.5%) | G(17.8%) | Y(17.7%) |
| | | K(9.3%) | D(23.7%) | R(12.8%) | S(13.7%) | S(15.5%) | S(13.6%) | Y(14.9%) | G(15.3%) |
| | | | E(12.1%) | S(11.5%) | Y(8.7%) | A(9.8%) | Y(10.1%) | S(12.1%) | A(14.3%) |
| | | | R(10.0%) | P(8.1%) | A(8.2%) | Y(9.2%) | A(9.9%) | D(9.4%) | W(7.9%) |
| | | | V(9.9%) | L(7.9%) | R(7.8%) | V(7.6%) | T(7.4%) | A(7.5%) | P(7.7%) |
| | | | A(9.5%) | V(6.4%) | V(6.9%) | D(5.7%) | L(6.1%) | T(5.7%) | S(7.5%) |
| | | | S(9.2%) | D(5.8%) | D(6.5%) | T(5.5%) | V(5.9%) | N(5.5%) | L(5.0%) |
| | | | | A(5.8%) | T(6.3%) | R(5.5%) | D(5.8%) | W(5.3%) | T(4.6%) |
| | | | | Y(5.4%) | P(4.9%) | L(4.3%) | W(4.9%) | R(5.0%) | V(4.3%) |
| | | | | T(4.5%) | L(4.8%) | W(3.7%) | R(4.5%) | L(4.6%) | D(3.5%) |
| | | | | E(3.9%) | I(3.4%) | P(3.6%) | P(3.7%) | V(4.0%) | R(3.3%) |
| | | | | I(3.9%) | E(3.1%) | E(3.3%) | E(2.9%) | P(2.9%) | N(2.7%) |
| | | | | N(2.3%) | W(2.8%) | I(3.1%) | N(2.7%) | E(2.1%) | E(2.6%) |
| | | | | F(2.3%) | F(2.1%) | N(2.2%) | I(2.1%) | F(1.7%) | F(2.0%) |
| | | | | W(2.2%) | K(1.8%) | F(1.8%) | F(1.9%) | K(1.4%) | I(1.8%) |

| | 100B | 101 | 102 | 103 |
|---|---|---|---|---|
| | F(76.2%) | D(100.0%) | Y(77.3%) | W(100.0%) |
| | L(15.9%) | | I(11.4%) | |
| | I(7.9%) | | P(11.3%) | |

TABLE 3E

Optimized library amino acid composition for the HC-CDR3 loop with length L = 11. For each position the different amino acids present are shown together with their relative frequencies. To increase overall variability also position 94 preceding the HC-CDR3 loop has been varied for HC-CDR3 loop length 11.

| 92 | 93 | 94 | 95 | 96 | 97 | 98 | 99 | 100 | 100A | 100B |
|---|---|---|---|---|---|---|---|---|---|---|
| C(100.0%) | A(100.0%) | R(87.7%) | G(28.8%) | G(19.1%) | G(18.9%) | G(19.4%) | G(20.8%) | G(16.5%) | Y(18.6%) | Y(18.8%) |
| | | K(12.3%) | D(27.3%) | R(12.5%) | S(14.1%) | S(16.6%) | S(16.4%) | S(14.5%) | G(17.0%) | G(16.8%) |
| | | | E(11.5%) | S(10.9%) | Y(9.6%) | Y(12.1%) | A(10.6%) | Y(12.8%) | S(10.8%) | A(12.9%) |
| | | | V(11.1%) | P(8.3%) | R(8.3%) | A(10.1%) | Y(10.5%) | A(9.0%) | D(8.0%) | W(9.7%) |
| | | | A(11.0%) | L(8.0%) | A(7.4%) | V(7.0%) | V(7.0%) | T(7.1%) | N(6.4%) | P(8.1%) |
| | | | R(10.4%) | Y(6.4%) | V(7.4%) | D(6.1%) | T(6.0%) | L(5.9%) | R(6.0%) | S(6.3%) |
| | | | | D(5.9%) | D(6.3%) | T(5.5%) | D(5.8%) | D(5.8%) | A(6.0%) | L(5.1%) |
| | | | | A(5.7%) | T(5.5%) | R(4.5%) | L(4.7%) | W(5.5%) | T(5.4%) | T(4.7%) |

TABLE 3E-continued

Optimized library amino acid composition for the HC-CDR3 loop with length L = 11. For each position the different amino acids present are shown together with their relative frequencies. To increase overall variability also position 94 preceding the HC-CDR3 loop has been varied for HC-CDR3 loop length 11.

| | | | | | | | |
|---|---|---|---|---|---|---|---|
| | V(5.6%) | P(4.9%) | L(4.4%) | R(4.4%) | R(5.3%) | W(5.2%) | V(3.7%) |
| | T(4.5%) | L(4.6%) | W(3.5%) | W(4.0%) | V(5.1%) | L(4.8%) | R(3.1%) |
| | I(4.1%) | I(4.3%) | I(3.5%) | P(3.2%) | P(3.9%) | V(3.8%) | D(3.0%) |
| | E(3.6%) | E(3.4%) | P(2.6%) | I(2.4%) | E(3.1%) | P(3.2%) | N(3.0%) |
| | F(2.8%) | W(3.2%) | E(2.3%) | E(2.3%) | N(3.0%) | E(2.7%) | F(2.7%) |
| | N(2.5%) | N(2.2%) | F(2.3%) | N(2.0%) | F(2.4%) | F(2.2%) | E(2.3%) |

| | 100C | 101 | 102 | 103 |
|---|---|---|---|---|
| | F(77.3%) | D(100.0%) | Y(85.1%) | W(100.0%) |
| | L(15.2%) | | P(14.9%) | |
| | I(7.5%) | | | |

TABLE 3F

Optimized library amino acid composition for the HC-CDR3 loop with length L = 12.
For each position the different amino acids present are shown together with their relative frequencies.

| 92 | 93 | 94 | 95 | 96 | 97 | 98 | 99 | 100 | 100A | 100B | 100C |
|---|---|---|---|---|---|---|---|---|---|---|---|
| C(100.0%) | A(100.0%) | R(100.0%) | D(33.2%) | G(18.5%) | G(19.7%) | G(18.1%) | G(19.2%) | G(19.9%) | G(15.2%) | Y(20.2%) | Y(22.6%) |
| | | | G(28.8%) | R(14.4%) | S(12.6%) | S(17.5%) | S(18.8%) | S(16.6%) | S(14.8%) | G(17.9%) | G(17.0%) |
| | | | E(13.4%) | P(9.9%) | Y(12.2%) | Y(12.1%) | Y(11.8%) | Y(12.4%) | Y(14.4%) | S(10.1%) | A(14.3%) |
| | | | A(12.3%) | S(9.7%) | R(8.6%) | V(8.6%) | A(11.5%) | A(9.6%) | A(7.6%) | D(9.7%) | W(12.1%) |
| | | | V(12.2%) | L(9.3%) | A(7.7%) | A(8.3%) | V(6.6%) | T(6.9%) | T(7.4%) | N(8.3%) | P(7.5%) |
| | | | | V(6.4%) | V(7.4%) | D(6.6%) | D(6.6%) | V(6.5%) | L(7.0%) | W(5.5%) | S(5.3%) |
| | | | | Y(5.8%) | D(6.3%) | T(5.8%) | T(5.8%) | D(5.3%) | W(5.8%) | R(5.3%) | L(4.1%) |
| | | | | A(5.5%) | T(5.4%) | R(5.2%) | L(4.5%) | W(5.1%) | R(5.6%) | T(5.3%) | T(4.0%) |
| | | | | D(5.4%) | L(5.2%) | L(4.6%) | R(4.2%) | L(4.9%) | P(5.4%) | A(4.8%) | V(3.1%) |
| | | | | T(4.6%) | I(4.5%) | I(3.9%) | W(3.7%) | R(4.2%) | V(5.4%) | P(3.8%) | D(2.8%) |
| | | | | E(4.0%) | P(4.4%) | W(3.3%) | I(2.7%) | P(3.7%) | D(5.1%) | L(3.5%) | R(2.5%) |
| | | | | I(3.9%) | E(3.4%) | P(3.2%) | N(2.3%) | I(2.4%) | N(3.4%) | V(3.1%) | F(2.3%) |
| | | | | K(2.8%) | W(2.7%) | E(2.6%) | P(2.1%) | E(2.4%) | E(3.1%) | E(2.5%) | N(2.2%) |

| | 100D | 101 | 102 | 103 |
|---|---|---|---|---|
| | F(86.5%) | D(100.0%) | Y(100.0%) | W(100.0%) |
| | L(13.5%) | | | |

TABLE 3G

Optimized library amino acid composition for the HC-CDR3 loop with length L = 13.
For each position the different amino acids present are shown together with their relative frequencies.

| 92 | 93 | 94 | 95 | 96 | 97 | 98 | 99 | 100 | 100A | 100B | 100C |
|---|---|---|---|---|---|---|---|---|---|---|---|
| C(100.0%) | A(100.0%) | R(100.0%) | D(40.5%) | G(17.6%) | G(20.8%) | G(17.1%) | G(20.0%) | G(19.4%) | G(19.5%) | Y(18.9%) | Y(24.9%) |
| | | | G(32.2%) | R(16.0%) | S(12.2%) | S(16.0%)) | S(18.5%) | S(17.6%) | S(15.8%) | G(16.5%) | G(18.2%) |
| | | | V(13.9%) | P(12.1%) | R(11.4%) | Y(14.5%) | Y(13.4%) | Y(13.9%) | Y(15.2%) | S(14.1%) | D(10.6%) |
| | | | A(13.4%) | S(10.9%) | Y(10.7%) | V(9.0%) | A(9.8%) | A(9.9%) | A(8.4%) | L(7.5%) | N(9.4%) |
| | | | | L(10.4%) | A(7.9%) | A(8.3%) | V(7.8%) | V(7.2%) | V(7.2%) | T(7.3%) | S(9.2%) |
| | | | | A(7.1%) | V(7.8%) | D(7.7%) | D(6.4%) | D(7.2%) | T(7.1%) | P(6.6%) | W(6.0%) |
| | | | | V(6.2%) | D(6.9%) | R(7.1%) | T(5.6%) | T(6.7%) | R(6.1%) | A(6.5%) | R(5.0%) |
| | | | | Y(5.8%) | L(6.4%) | T(5.8%) | L(5.2%) | L(6.0%) | L(5.7%) | R(6.5%) | T(4.7%) |
| | | | | D(4.8%) | P(5.6%) | I(5.2%) | R(5.1%) | W(4.8%) | W(5.6%) | V(5.7%) | A(4.2%) |
| | | | | T(4.7%) | T(5.5%) | L(4.8%) | W(4.3%) | R(4.2%) | D(5.6%) | D(5.2%) | P(3.9%) |
| | | | | I(4.3%) | I(4.8%) | P(4.5%) | I(3.8%) | P(3.2%) | P(3.9%) | W(5.2%) | L(3.8%) |

| | 100D | 100E | 101 | 102 | 103 |
|---|---|---|---|---|---|
| | Y(22.8%) | F(100.0%) | D(100.0%) | Y(100.0%) | W(100.0%) |
| | G(20.3%) | | | | |
| | A(15.4%) | | | | |
| | W(14.5%) | | | | |
| | P(6.8%) | | | | |
| | S(5.2%) | | | | |
| | L(4.1%) | | | | |

TABLE 3G-continued

Optimized library amino acid composition for the HC-CDR3 loop with length L = 13.
For each position the different amino acids present are shown together with their relative frequencies.

V(3.2%)
T(3.0%)
R(2.7%)
D(2.2%)

TABLE 3H

Optimized library amino acid composition for the HC-CDR3 loop with length L = 14.
For each position the different amino acids present are shown together with their relative frequencies.

| 92 | 93 | 94 | 95 | 96 | 97 | 98 | 99 | 100 | 100A | 100B | 100C |
|---|---|---|---|---|---|---|---|---|---|---|---|
| C(100.0%) | A(100.0%) | R(100.0%) | D(45.4%) | G(21.9%) | G(20.5%) | G(20.0%) | G(20.5%) | G(21.6%) | G(20.3%) | Y(21.3%) | Y(26.0%) |
| | | | G(38.2%) | R(16.4%) | S(13.4%) | Y(15.7%) | S(19.8%) | S(20.1%) | S(18.5%) | G(20.1%) | G(16.3%) |
| | | | E(16.4%) | P(12.4%) | Y(12.9%) | S(15.7%) | Y(15.7%) | Y(13.7%) | Y(17.1%) | S(16.2%) | S(14.2%) |
| | | | | L(11.6%) | R(12.6%) | D(9.9%) | A(9.5%) | A(10.4%) | A(9.3%) | T(7.8%) | P(9.0%) |
| | | | | S(10.7%) | V(9.1%) | V(9.3%) | V(8.9%) | V(8.7%) | T(8.3%) | A(7.8%) | L(8.2%) |
| | | | | A(7.6%) | L(8.5%) | R(8.4%) | D(7.0%) | D(7.7%) | Y(8.1%) | Y(7.3%) | R(7.3%) |
| | | | | Y(7.4%) | A(8.2%) | A(8.3%) | T(6.9%) | L(6.3%) | D(6.6%) | P(6.7%) | T(7.1%) |
| | | | | V(6.6%) | P(7.8%) | T(6.5%) | R(6.3%) | T(6.3%) | L(5.9%) | L(6.5%) | A(6.6%) |
| | | | | T(5.4%) | D(7.1%) | L(6.2%) | L(5.4%) | W(5.3%) | W(5.9%) | R(6.3%) | V(5.5%) |

| | | | | | | 100D | 100E | 100F | 101 | 102 | 103 |
|---|---|---|---|---|---|---|---|---|---|---|---|
| | | | | | | Y(30.1%) | Y(25.1%) | F(100.0%) | D(100.0%) | Y(100.0%) | W(100.0%) |
| | | | | | | G(18.3%) | G(23.0%) | | | | |
| | | | | | | D(12.2%) | A(16.4%) | | | | |
| | | | | | | N(9.9%) | W(14.7%) | | | | |
| | | | | | | S(9.2%) | P(6.7%) | | | | |
| | | | | | | W(6.0%) | S(4.4%) | | | | |
| | | | | | | R(5.5%) | L(4.2%) | | | | |
| | | | | | | P(4.6%) | Y(2.9%) | | | | |
| | | | | | | A(4.2%) | T(2.6%) | | | | |

TABLE 3I

Optimized library amino acid composition for the HC-CDR3 loop with length L = 15. For
each position the different amino acids present are shown together with their relative frequencies.

| 92 | 93 | 94 | 95 | 96 | 97 | 98 | 99 | 100 | 100A | 100B | 100C |
|---|---|---|---|---|---|---|---|---|---|---|---|
| C(100.0%) | A(100.0%) | R(100.0%) | D(54.1%) | G(20.8%) | G(23.7%) | Y(19.4%) | G(21.0%) | G(22.2%) | S(23.4%) | G(23.5%) | Y(28.4%) |
| | | | G(45.9%) | R(19.6%) | Y(17.2%) | G(17.9%) | S(19.9%) | S(21.4%) | G(21.6%) | Y(21.3%) | G(19.3%) |
| | | | | P(14.2%) | R(13.7%) | S(17.2%) | Y(17.7%) | Y(15.1%) | Y(14.9%) | S(19.2%) | S(15.7%) |
| | | | | L(12.1%) | S(12.6%) | D(10.6%) | V(9.6%) | V(10.0%) | V(8.8%) | T(7.7%) | R(8.0%) |
| | | | | S(10.9%) | V(9.0%) | V(9.9%) | A(9.5%) | A(9.2%) | T(8.6%) | A(7.7%) | A(7.5%) |
| | | | | V(7.6%) | L(8.1%) | R(9.0%) | D(8.5%) | D(8.3%) | A(8.4%) | V(7.2%) | P(7.3%) |
| | | | | Y(7.5%) | P(7.9%) | A(8.5%) | R(7.0%) | T(6.9%) | D(7.6%) | D(6.9%) | T(6.9%) |
| | | | | A(7.3%) | D(7.8%) | T(7.5%) | L(6.8%) | L(6.8%) | L(6.7%) | L(6.5%) | L(6.8%) |

| | | | | | | 100D | 100E | 100F | 100G | 101 | 102 | 103 |
|---|---|---|---|---|---|---|---|---|---|---|---|---|
| | | | | | | Y(34.3%) | Y(35.1%) | G(27.3%) | F(100.0%) | D(100.0%) | Y(100.0%) | W(100.0%) |
| | | | | | | G(15.5%) | G(16.9%) | Y(23.5%) | | | | |
| | | | | | | S(14.0%) | D(11.9%) | W(16.5%) | | | | |
| | | | | | | L(8.4%) | N(11.9%) | A(16.4%) | | | | |
| | | | | | | P(8.3%) | S(8.3%) | P(6.4%) | | | | |
| | | | | | | T(6.8%) | W(6.0%) | S(4.0%) | | | | |
| | | | | | | R(6.7%) | R(5.2%) | L(3.5%) | | | | |
| | | | | | | A(6.0%) | P(4.6%) | T(2.4%) | | | | |

Oligonucleotides for each HC-CDR3 loop length were then designed based on the values in tables 3A-I. At positions with more than one amino acid the corresponding trimer-blocks from FIG. 5 were selected and included in the design in the desired percent fraction as a mixture. The use of trimer blocks encoding complete codons are advantageous because they allow to generate the amino acid composition and frequencies shown in tables 3A-I, at each position of each HC-CDR3 loop, without generation of undesired stop codons or inclusion of undesired amino acids as would be the case for standard degenerate oligonucleotides. Constant parts of the oligonucleotides (positions with only 1 amino acid present or parts necessary for cloning) are instead designed to be synthesized by standard oligonucleotide synthesis. The oligonucleotide design for the HC-CDR3 loop length 15 is shown in FIG. 11. Oligonucleotides for the other HC-CDR3 loop lengths were designed in an equivalent fashion using the values given in tables 3A-I. Oligonucleotides were synthesized by EllaBiotech using their trimer-block technology.

Example 6. Generation of the Library Diversity by Inserting the Oligonucleotides Containing the HC-CDR3 Diversity into the BaseVector_VH3_VK1_22

In a first step the single-stranded oligonucleotides encoding the HC-CDR3 loop diversity were subjected to primer extension (generation of double-stranded oligonucleotides) using primer Sty_rev_1 (SEQ ID 9) and Herculase II-Fusion DNA polymerase (Agilent cat #600679) and the following conditions: denaturation at 98° C. for 35 sec, annealing at 47° C. for 15 sec, elongation for 15 sec at 47° C. and 65° C. for oligonucleotides encoding loop lengths 7 to 11 and 12 to 15, respectively. The resulting double-stranded oligonucleotides were then amplified using primers PstI_for_1 (SEQ ID 10) and Sty_rev_2 (SEQ ID 11) and using Herculase II-Fusion DNA polymerase (Agilent cat #600679) with the following conditions: denaturation at 95° C. for 15 sec, annealing at 52° C. for 15 sec, elongation at 72° C. for 15 sec repeated for 16 cycles.

After amplification, oligonucleotides were purified through Qiaquick nucleotide Removal Kit (Qiagen Cat #28304), subjected to digestion with PstI/StyI restriction enzymes and ligated into the PstI/StyI-digested phagemid vector at an insert:vector ratio 1:6 (transformation efficiency in the range of $5 \times 10^7/10^8$ clones/µg), separately for each HC-CDR3 loop length. The resulting ligation product was then transformed into XL1blue-MRF' electro-competent cells (50 ng vector in 50 µl cells), plated onto 23×23 cm 2XTYagar Bioassay plates and grown o/n at 37° C. The following day cells were harvested from the plates in 2XTYAG/glycerol 17% and stored at −80° C. In order to achieve the desired HC-CDR3 loop length distribution and overall library complexity of $1.3 \times 10^{10}$ the transformation efficiency was checked regularly reiterating the clone harvesting cycle until the desired HC-CDR3 loop length distribution and complexity had been reached. Pooling the clones from all individual harvesting cycles together then produced the final library.

To prepare the library in the phage format, 6 ml of the pooled bacteria were inoculated in 4 L of 2XTY/Ampicillin/2% Glucose with a starting OD600=0.1 for a total of $8.4 \times 10^{10}$ bacteria representing about 6.5 times the library complexity. Once OD600=0.5 was reached, cells were superinfected with M13K07 helper phage at a MOI=10, the media was changed to 2XTY/Ampicillin/Kanamycin and cells were incubated under shaking o/n at 30° C. The resulting cell culture was centrifuged and the supernatant containing the phage library was subjected to two PEG precipitation steps (addition of 20% PEG8000/NaCl 2.5M for 3/10 of the volume) followed by re-suspension of the phages in 1X TE for a further purification step on a CsCl gradient. The phage population was then collected from the gradient and dialyzed o/n against 2 L of 1X TE to eliminate the CsCl, the phage concentration in the preparation was determined by TU, pfu and PP/ml and stored in TBE1×, glycerol 15%, $NaN_3$ 0.02%.

Example 7. Identification of Selective Binders to Bovine Serum Albumin (BSA)

As in the several steps of selection the standard blocking buffer is made of 2% milk, and therefore contains plenty of bovine albumin, we reasoned that this soluble BSA could compete with the target recombinant BSA protein coated on the plastic for selection. Consequently, for the selection of phages on this target a blocking buffer reagent with 1% casein (Roche) was used instead of the standard blocking buffer. In addition, to avoid selection of specific phages against $NaN_3$ present in the BSA solution used for coating, a blocking buffer reagent containing 0.02% $NaN_3$ was employed, so that phages potentially specific for $NaN_3$ would remain in solution and be washed away.

For this target $2.1 \times 10^{12}$ TU (phages) from the library were incubated with purified BSA, coated onto immunotubes, in a final volume of 3 ml, at a concentration of 50 µg/ml (1st round) and scaled down to 30 and 15 µg/ml, respectively, in the two following rounds of selection.

Figure 12A:
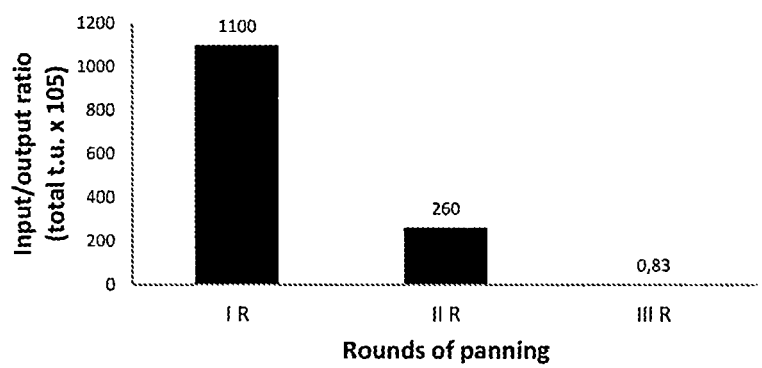
FIGS. 12A-12D: Isolation of BSA specific M13-scFv clones from the library.
Figure 12B:
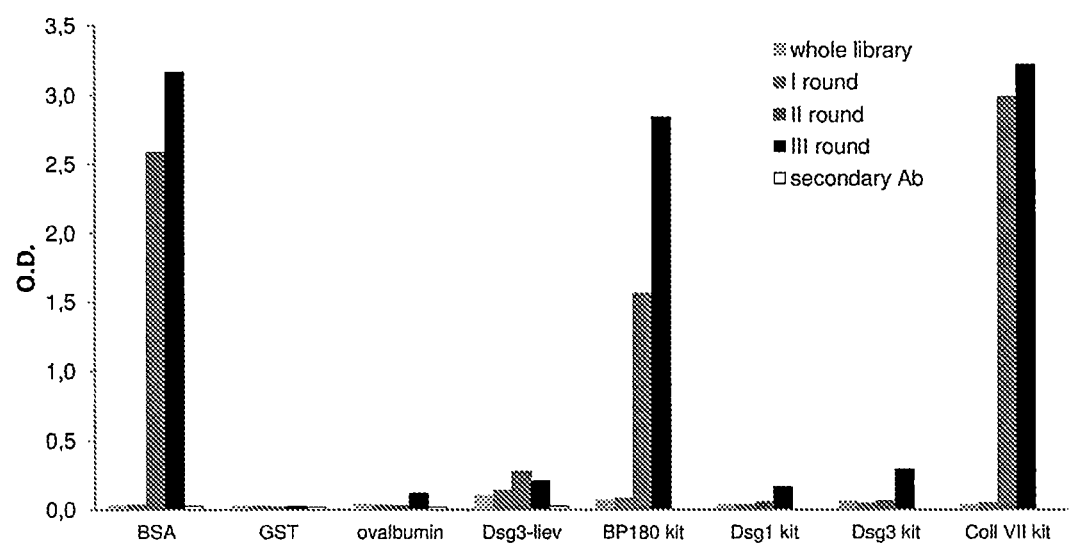
Figures 12C, 12D:
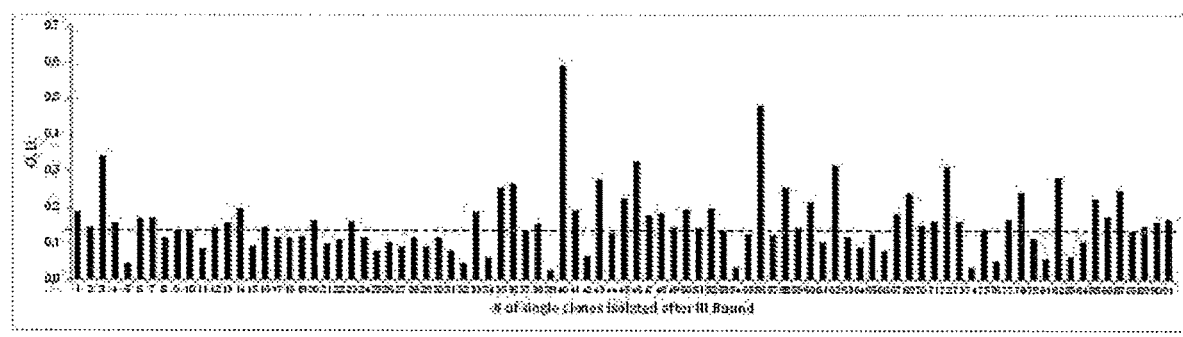

The input/output ratio represents a measure of the enrichment of specific clones, in fact it is usually very high in the first round of selection, and rapidly decreases in the following rounds, when the population of phages eluted from the previous round is progressively enriched for specific phages. For this target the input/output ratio suggested a possible enrichment of specific clones from the 1st round to the $3^{rd}$ round of panning (FIG. 12A). Polyclonal phages were tested by phage ELISA on BSA and several unrelated antigens. Anti-BSA M13-scFv clones were present in the $2^{nd}$ and $3^{rd}$ rounds of the selection (FIG. 12B). Unspecific binding to commercially produced antigens (BP180 and Collagen VII) coated on wells was probably due to blocking reagents containing BSA that were used by the manufacturer (MBL) (FIG. 12B). The percentage of anti-BSA clones in the $3^{rd}$ round of selection was 50 of 89 (56%) (FIG. 12C). All 12 positive clones analyzed were specific for BSA (FIG. 12D).

Example 8. Identification of Selective Binders to Ovalbumin (OVA)

Figure 13A:
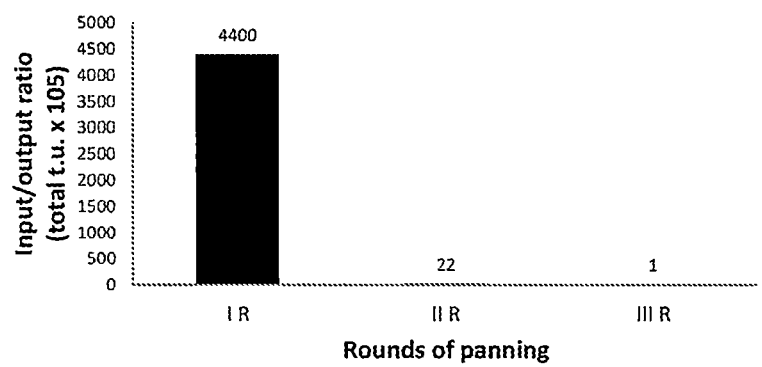
Figure 13B:
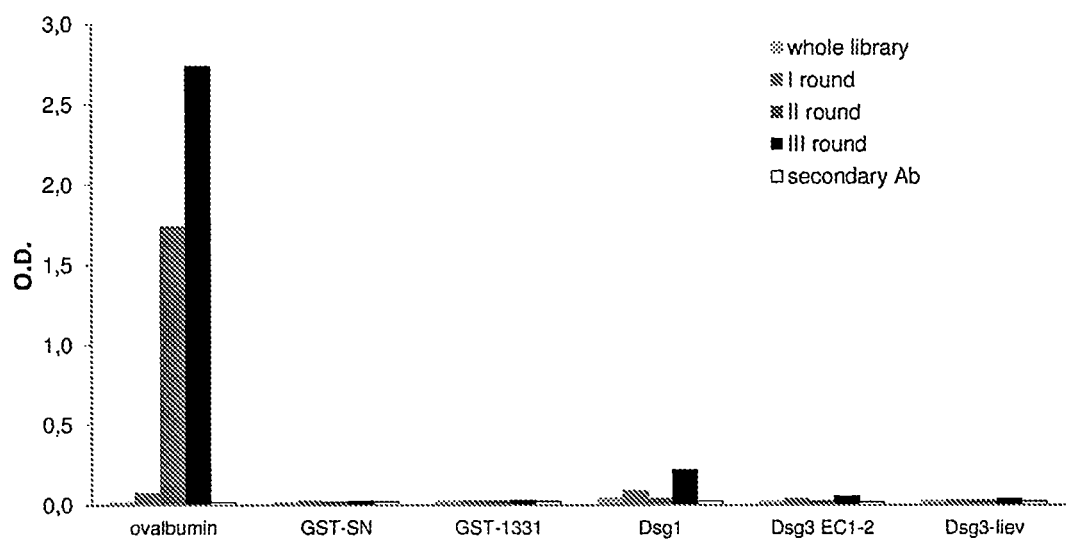
Figure 13C:
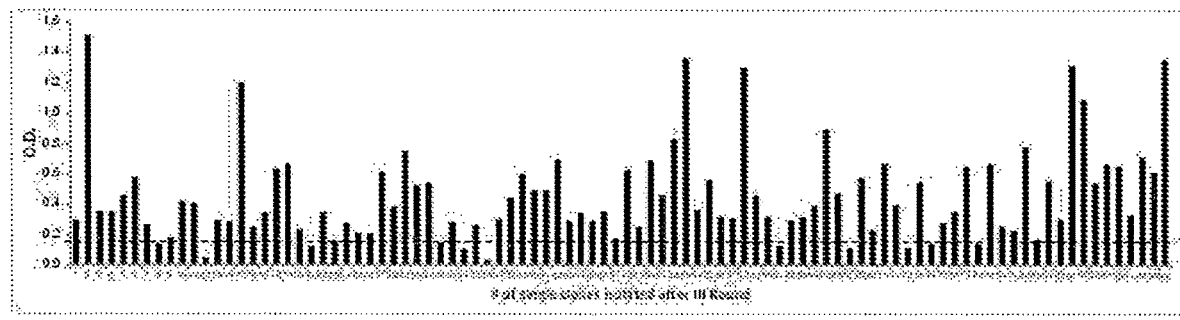
Figure 13D:
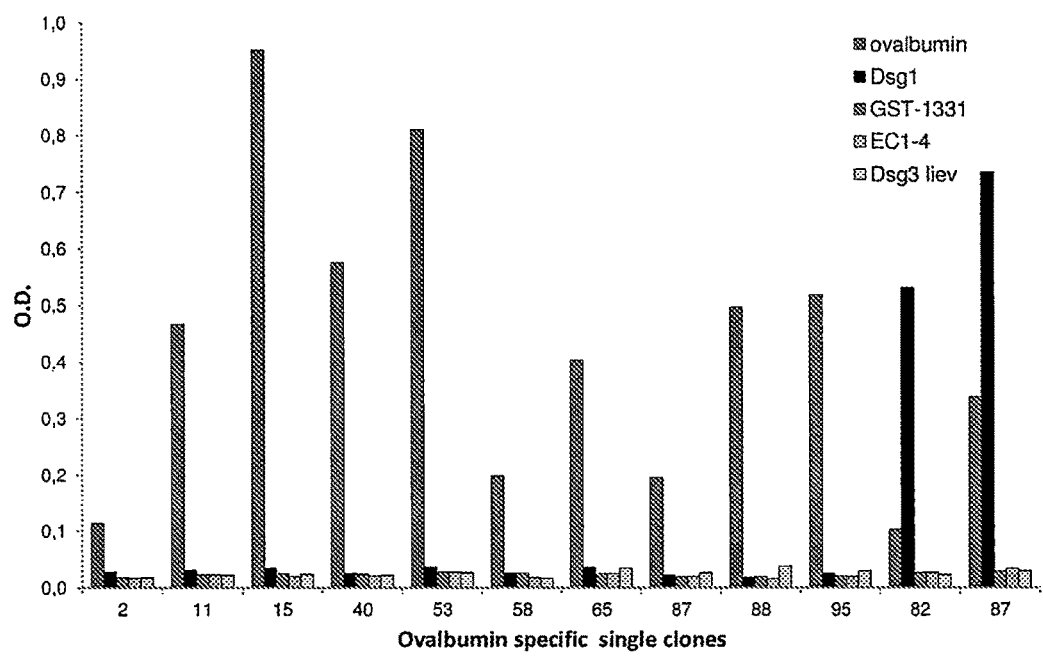

For this target the selection of positive phages from $9.3 \times 10^{12}$ TU as total clones was performed by coating an immunotube with OVA at a concentration of 50 µg/ml (1st round), that was scaled down to 30 and 10 µg/ml in the two following rounds of selection, respectively. The input/output ratio suggested a possible enrichment of specific clones from the 1st round to the $2^{nd}$ and 3rd rounds of panning (FIG. 13A). Polyclonal phages were tested by phage ELISA on OVA and several unrelated antigens. Anti-OVA M13-scFv clones were present in the II and III rounds of selection without any unspecific binding to other antigens (FIG. 13B). The percentage of anti-OVA clones in the third round of selection was 81 of 94 (86%) (FIG. 13C). The analysis of 10 positive clones showed that all of them were specific for OVA (FIG. 13D).

Example 9. Identification of Selective Binders to Desmoglein 1 (Dsg1)

Figure 14A:
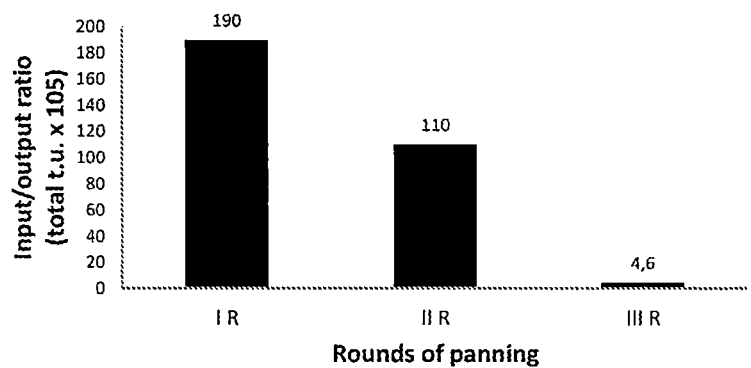
Figure 14B:
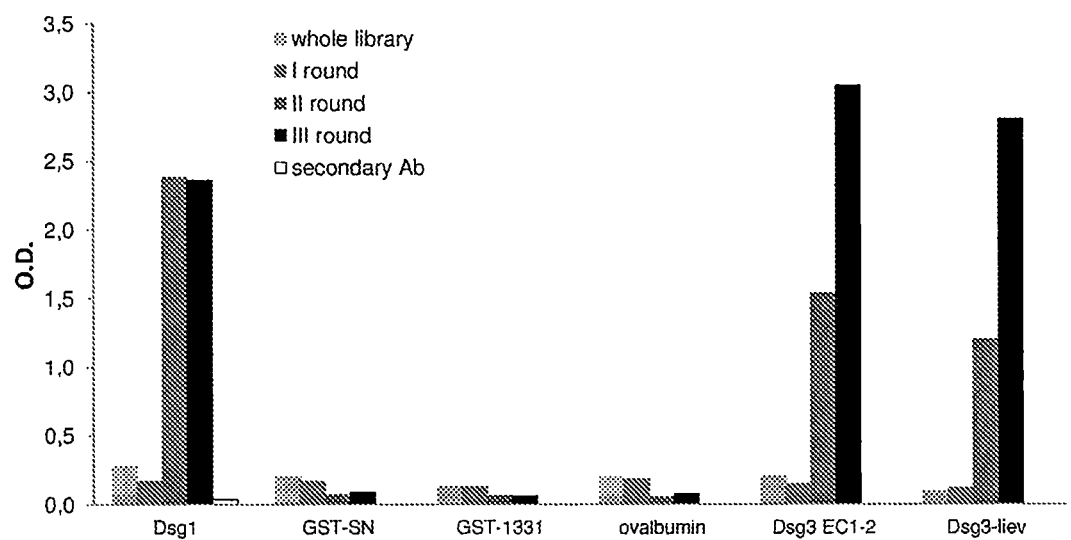

The library selection was performed by using ten Dsg1 pre-coated wells (MBL ELISA kit) and $9.3 \times 10^{12}$ TU in 1600 µl of library-containing buffer (160 µl/well). The concentration of coated antigen is unknown. The input/output ratio suggested a possible enrichment of specific clones from the 1st round to the 3rd round of panning (FIG. 14A). Polyclonal phages were tested by phage ELISA on Dsg1 pre-coated wells and several unrelated antigens. Anti-Dsg1 M13-scFvs were present in the 2nd and 3rd rounds of selection without any unspecific binding to other antigens with the exception of Dsg3 and Dsg3-derived constructs (EC1-2) (FIG. 14B). The detected cross-reactivity was likely due to the high sequence homology between Dsg1 and 3. The percentage of anti-Dsg1 clones in the 3rd round of selection was 86 of 94 (91%) (FIG. 14C). The analysis of 8 positive clones showed that all of them were specific for Dsg1 (FIG. 14D).

Example 10. Identification of Selective Binders to Fibroblast Growth Factor Receptor 4 (FGFR4)

Figure 15A:
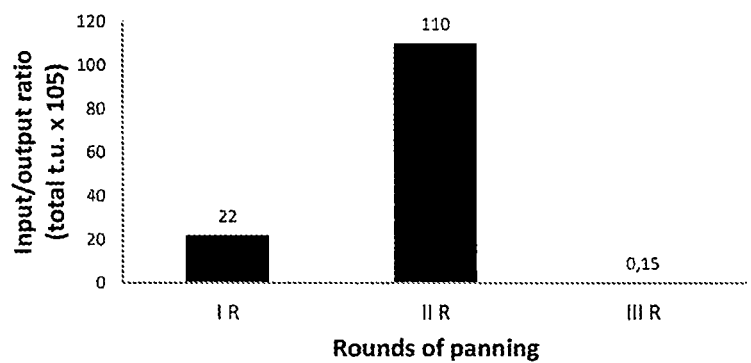
Figure 15B:
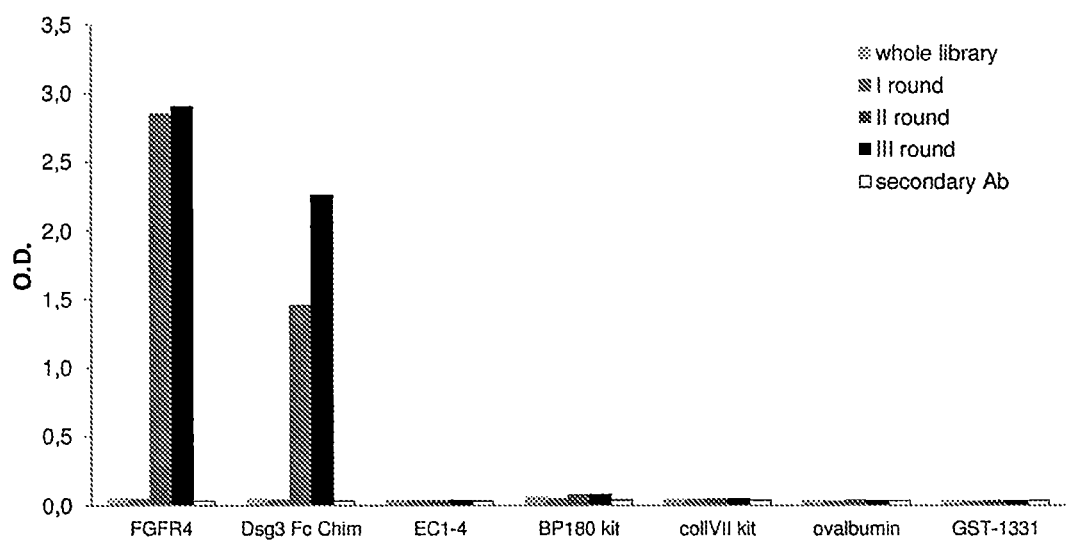
Figure 15C:
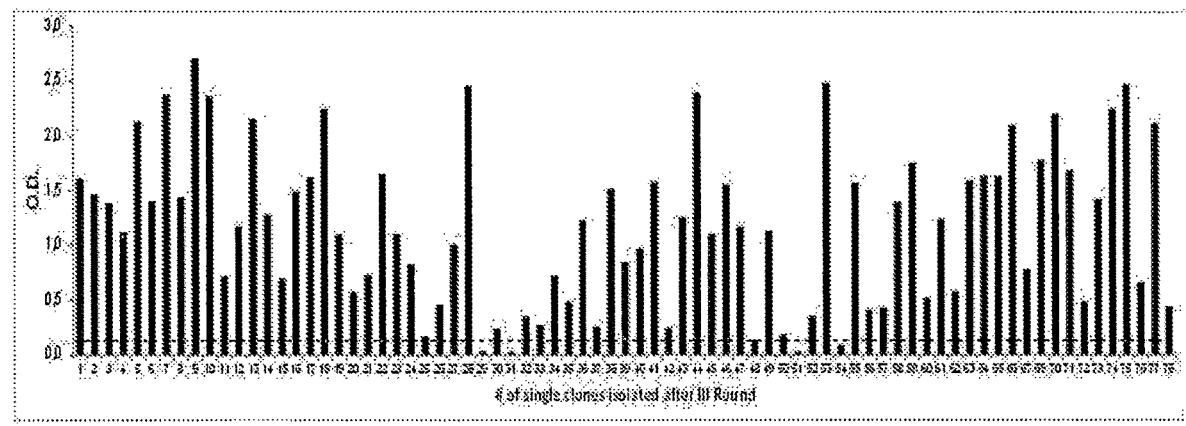
Figure 15D:
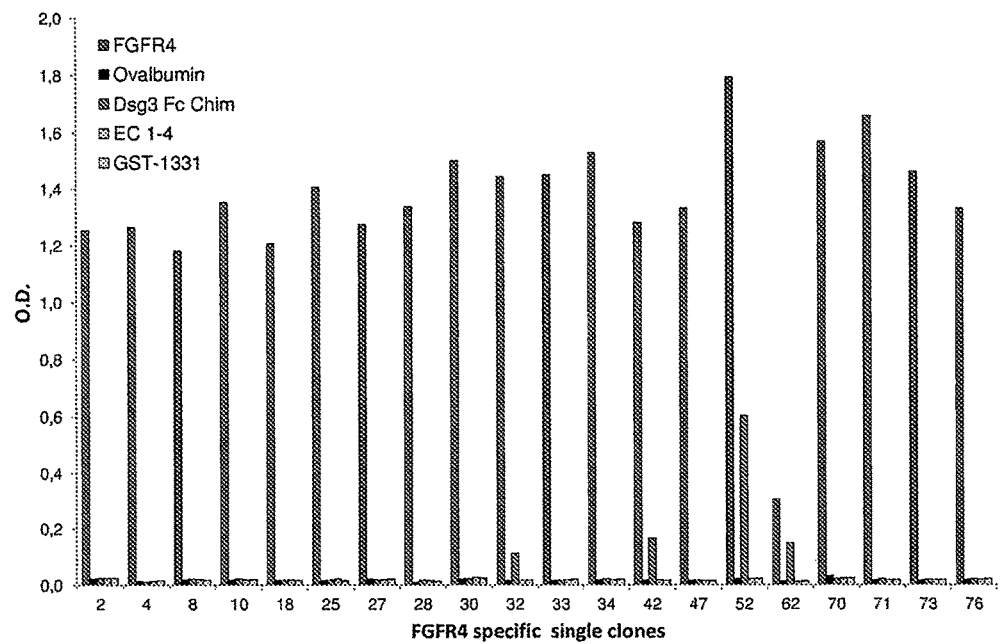

The library selection was performed by using 1600 µl of the library (160 µl/well) in 10 microplate wells, coated with FGFR-4 at a concentration of 10 µg/ml. All three rounds of selection were performed on wells coated with the same concentration of FGFR-4. Since the FGFR-4 recombinant protein is a chimeric protein fused to human IgG1 FC and in order to reduce the amount of anti-FC phages selected, the first round was performed using a different recombinant protein fused to FC (8 µg/ml of Dsg3-FC). The input/output ratio suggested a possible enrichment of specific clones from the I round to the III round of panning (FIG. 15A). Polyclonal phages were tested by phage ELISA on FGFR-4 and several unrelated antigens. Anti-FGFR-4 M13-scFv clones were present in the 2nd and 3rd rounds of the selection without any unspecific binding to other antigens (FIG. 15B). Of note, the competitive selection with Dsg3-FC did not eliminate all anti-FC phages. In fact, the polyclonal mixtures reacted with both FGFR-4 and Dsg3-FC (FIG. 15B). The percentage of anti-FGFR-4-FC clones in the 3rd round of selection was 72 of 77 (94%) (FIG. 15C). Twenty positive clones analyzed bound to FGFR-4 and four weakly reacted also to Dsg3-FC (FIG. 15D). Thus, the competitive biopanning with Dsg3-FC had succeeded in reducing the amount of anti-FC clones.

The results from the selections on the four targets are summarized in Table 4.

TABLE 4

Summary of the results of library screening on four different validation targets. A) Number and percentage of phages positively selected against every target; B) Specificity in terms of binding vs the specific target or other unrelated recombinant proteins, and number of different sequences found for each target (see below).

A

| Antigen | Number of rounds | # analyzed clones | # positive clones | % anti-target positive clones | Specificity for target |
|---|---|---|---|---|---|
| BSA | 3 | 89 | 50 | 56% | 10/12 |
| OVA | 3 | 94 | 81 | 86% | 10/10 |
| DSG1 | 3 | 94 | 86 | 91% | 8/8 |
| FGFR4 | 3 | 77 | 72 | 94% | 17/20 |

B

| Antigen | # positive clones | Sequence clones | # of different sequences | # groups of sequences |
|---|---|---|---|---|
| BSA | 50 | 5 | 1 | 1 |
| OVA | 81 | 10 | 10 | 4 |
| DSG1 | 86 | 8 | 5 | 3 |
| FGFR4 | 72 | 10 | 3 | 3 |

For all four target antigens, the selections were successful generating a large number of clones and, importantly, clones that recognize the target antigen with high specificity.

Example 11. Identification of the HC-CDR3 DNA Sequence of the Selected Phages As reported in panel B of Table 4, a number of clones were sequenced for each target and the sequences were analyzed and aligned as depicted in Table 5 (see below).

In the case of BSA, 5 clones were sequenced, and all of them showed the same HC-CDR3 sequence. Instead, all 10 OVA-positive clones sequenced were unique clones and correspond to at least four different family of clones. Also in the case of Dsg1, 8 positive clones were sequenced and all of them were specific and 5 out of 8 were unique, with three different families of clones.

Lastly, 10 FGFR-4 specific clones were sequenced and seven were shown to have identical sequences. Three different family of clones were identified.

The affinity of M13-scFv clone (cl. 33) for its target FGFR-4 was determined by phage ELISA and found to be in the nanomolar range ($8.7 \times 10^{-8}$ M). This value compares favorably to values reported by Pfizer (Mahon et al. J. Mol: Biol. 405, 1712, 2013), who found affinities between 105 and 457 nM for phages selected with their HC-CDR3-only library.

TABLE 5

Sequence analysis of a subset of clones isolated through the selections.
For each target 5 to 10 clones were sequenced.

| ANTIGEN | CLONES | | Pos 94 | H-CDR3 | | Pos 103 | CDR3 | SEQ ID NO |
|---|---|---|---|---|---|---|---|---|
| BSA | 40,46,56,58,82 | CA | R | DPLDIYSWGYFDY | | W | 13 | 12 |
| | | | | | | | | |
| OVA | 2 | CA | V | VTGVLWGFDY | | W | 10 | 13 |
| OVA | 11 | CA | K | DYASGYGYFDY | | W | 11 | 14 |
| OVA | 58 | CA | K | DYASGWGYFDY | | W | 11 | 15 |
| OVA | 15 | CA | K | DFGRGYGYFDY | | W | 11 | 16 |
| OVA | 65 | CA | K | DFRSGYGYFDY | | W | 11 | 17 |
| OVA | 40 | CA | Q | DVRRGCGYFDY | | W | 11 | 18 |
| OVA | 53 | CA | K | DVARGYGYFDY | | W | 11 | 19 |
| OVA | 95 | CA | K | DVWRGYGYFDY | | W | 11 | 20 |
| OVA | 88 | CA | K | DVGRGVGYFDY | | W | 11 | 21 |
| OVA | 87 | CA | K | VVGGVLYAFDY | | W | 11 | 22 |
| | | | | | | | | |
| DSG1 | 24,32,37,47 | CA | R | GAGYYGLPVYAFDY | | W | 14 | 23 |
| DSG1 | 73 | CA | R | GAGYSGLPVYAFDY | | W | 14 | 24 |
| DSG1 | 80 | CA | R | GAGYLGYPVYAFDY | | W | 14 | 25 |
| DSG1 | 91 | CA | R | ANWASSYEFDY | | W | 11 | 26 |
| DSG1 | 1 | CA | R | VGRYGYYDAAFDY | | W | 13 | 27 |
| | | | | | | | | |
| FGFR4 | 2,10,27,28,33,70,73 | CA | R | EGDPDLYFFDY | | W | 11 | 28 |
| FGFR4 | 18,25 | CA | R | GYAWPSWFDY | | W | 10 | 29 |
| FGFR4 | 30 | CA | R | EWWDYLYLDY | | W | 10 | 30 |

CONCLUSION

From the results obtained the library design was successful for all four target antigens tested. Besides the high target specificity obtained (Table 4), the library provides also a variety of distinct clone sequence families for each target. Importantly, the results obtained also well reflect the basic design principle of the library with most sequences having a HC-CDR3 length of 11. In addition, the presence of a number of selected clones with only a small number (often only 1) of different amino acid confirms that the library provides a large coverage for all HC-CDR3 loop variants for the most important HC-CDR3 length 9 to 11, as implemented in the design.

REFERENCES

Barbas C F 3rd, Bain J D, Hoekstra D M, Lerner R A. Semisynthetic combinatorial antibody libraries: a chemical solution to the diversity problem. Proc Natl Acad Sci USA. 1992 May 15; 89(10):4457-61.

Braunagel M, Little M. Construction of a semisynthetic antibody library using trinucleotide oligos. Nucleic Acids Res. 1997 Nov. 15; 25(22):4690-1.

Chothia C, Lesk A M. Canonical structures for the hyper-variable regions of immunoglobulins. J Mol Biol. 1987 Aug. 20; 196(4):901-17.

DeKosky B J, Ippolito G C, Deschner R P, Lavinder J J, Wine Y, Rawlings B M, Varadarajan N, Giesecke C, Dörner T, Andrews S F, Wilson P C, Hunicke-Smith S P, Willson C G, Ellington A D, Georgiou G.: High-throughput sequencing of the paired human immunoglobulin heavy and light chain repertoire. Nat Biotechnol. 2013 February; 31(2):166-9.

de Wildt R M 1, Hoet R M, van Venrooij W J, Tomlinson I M, Winter G. Analysis of heavy and light chain pairings indicates that receptor editing shapes the human antibody repertoire. J Mol Biol. 1999 Jan. 22; 285(3):895-901.

Ewert S 1, Huber T, Honegger A, Plückthun A. Biophysical properties of human antibody variable domains. Mol Biol. 2003 Jan. 17; 325(3):531-53.

Fellouse F A, Esaki K, Birtalan S, Raptis D, Cancasci V J, Koide A, Jhurani P, Vasser M, Wiesmann C, Kossiakoff A A, Koide S, Sidhu S S. High-throughput generation of synthetic antibodies from highly functional minimalist phage-displayed libraries. J Mol Biol. 2007 Nov. 2; 373 (4):924-40.

Glanville J 1, Zhai W, Berka J, Telman D, Huerta G, Mehta G R, Ni I, Mei L, Sundar P D, Day G M, Cox D, Rajpal A, Pons J. Precise determination of the diversity of a combinatorial antibody library gives insight into the human immunoglobulin repertoire. Proc Natl Acad Sci USA. 2009 Dec. 1; 106(48):20216-21.

Green L L. Transgenic mouse strains as platforms for the successful discovery and development of human therapeutic monoclonal antibodies. Curr Drug Discov Technol. 2014 March; 11(1):74-84.

Hoet R M, Cohen E H, Kent R B, Rookey K, Schoonbroodt S, Hogan S, Rem L, Frans N, Daukandt M, Pieters H, van Hegelsom R, Neer N C, Nastri H G, Rondon I J, Leeds J A, Hufton S E, Huang L, Kashin I, Devlin M, Kuang G, Steukers M, Viswanathan M, Nixon A E, Sexton D J, Hoogenboom H R, Ladner R C. Generation of high-affinity human antibodies by combining donor-derived and synthetic complementarity-determining-region diversity. Nat Biotechnol. 2005 March; 23(3):344-8.

Huang, S. C., Jiang, R., Glas, A. M. & Milner, E. C. Non-stochastic utilization of Ig V region genes in unselected human peripheral B cells. Mol. Immunol. 1996 33, 553-560.

Ippolito G C 1, Hoi K H, Reddy S T, Carroll S M, Ge X, Rogosch T, Zemlin M, Shultz L D, Ellington A D, Vandenberg C L, Georgiou G. Antibody repertoires in humanized NOD-scid-IL2Rγ(null) mice and human B cells reveals human-like diversification and tolerance checkpoints in the mouse. PLoS One. 2012; 7(4):e35497.

Kabat E A. Sequence of proteins of immunological interest. Bethesda: National Institute of Health; 1991, Vol. 1. Fifth Ed.

Knappik A, Ge L, Honegger A, Pack P, Fischer M, Wellnhofer G, Hoess A, Wölle J, Plückthun A, Virnekäs B. Fully synthetic human combinatorial antibody libraries (HuCAL) based on modular consensus frameworks and CDRs randomized with trinucleotides. J Mol Biol. 2000 Feb. 11; 296(1):57-86.

Mahon C M, Lambert M A, Glanville J, Wade J M, Fennell B J, Krebs M R, Armellino D, Yang S, Liu X, O'Sullivan C M, Autin B, Oficjalska K, Bloom L, Paulsen J, Gill D, Damelin M, Cunningham O, Finlay W J.: Comprehensive interrogation of a minimalist synthetic CDR-H3 library and its ability to generate antibodies with therapeutic potential. J Mol Biol. 2013 May 27; 425(10):1712-30.

McCafferty J 1, Fitzgerald K J, Earnshaw J, Chiswell D J, Link J, Smith R, Kenten J. Selection and rapid purification of murine antibody fragments that bind a transition-state analog by phage display. Appl Biochem Biotechnol. 1994 May-June; 47(2-3):157-71

Mondon P, Dubreuil O, Bouayadi K, Kharrat H. Human antibody libraries: a race to engineer and explore a larger diversity. Front Biosci. 2008 Jan. 1; 13:1117-29.

Pini A, Viti F, Santucci A, Carnemolla B, Zardi L, Neri P, Neri D. Design and use of a phage display library. Human antibodies with subnanomolar affinity against a marker of angiogenesis eluted from a two-dimensional gel. J Biol Chem. 1998 Aug. 21; 273(34):21769-76.

Philibert P, Stoessel A, Wang W, Sibler A P, Bec N, Larroque C, Saven J G, Courtête J, Weiss E, Martineau P.: A focused antibody library for selecting scFvs expressed at high levels in the cytoplasm. BMC Biotechnol. 2007 Nov. 22; 7:81.

Prassler J, Thiel S, Pracht C, Polzer A, Peters S, Bauer M, Nörenberg S, Stark Y, Kölln J, Popp A, Urlinger S, Enzelberger M. HuCAL PLATINUM, a synthetic Fab library optimized for sequence diversity and superior performance in mammalian expression systems. J Mol Biol. 2011 Oct. 14; 413(1):261-78.

Silacci, M., Brack, S., Schirru, G., Marlind, J., Ettorre, A., Merlo, A., Viti, F., Neri, D.: Design, construction, and characterization of a large synthetic human antibody phage display library. Proteomics. 2005 June; 5(9):2340-50.

Tonegawa S. Somatic generation of antibody diversity. Nature. 1983 Apr. 14; 302(5909):575-81.

Zemlin M, Klinger M, Link J, Zemlin C, Bauer K, Engler J A, Schroeder H W Jr, Kirkham P M.: Expressed murine and human CDR-H3 intervals of equal length exhibit distinct repertoires that differ in their amino acid composition and predicted range of structures. J Mol Biol. 2003 Dec. 5; 334(4):733-49.

The invention claimed is:

1. A library of DNA expression vectors, wherein each DNA expression vector encodes amino acid sequences of an antibody or functional fragment thereof, wherein the library of vectors encodes at least $1.3 \times 10^{10}$ unique amino acid sequences of antibodies or functional fragments thereof, wherein the diversity of the encoded unique amino acid sequences is generated by diversity of variegated DNA sequences that encode unique amino acid sequences in the antibody HC-CDR3 region and the position proceeding the antibody HC-CDR region (Kabat position 94), wherein the DNA expression vectors encode amino acid sequences in the antibody HC-CDR3 region and the position proceeding the antibody HC-CDR region with a HC-CDR3 length of 7, 8, 9, 10, 11, 12, 13, 14 and 15 amino acid residues, wherein the percentage of each length of the antibody HC-CDR3 region and the position proceeding the antibody HC-CDR region encoded by the library of DNA expression vectors is 0.1% for the length of 7 amino acid residues, 1.0% for the length of 8 amino acid residues, 2.5% for the length of 9 amino acid residues, 11.5% for the length of 10 amino acid residues, 28.3% for the length of 11 amino acid residues, 19.8% for the length of 12 amino acid residues, 17.7% for the length of 13 amino acid residues, 13.1% for the length of 14 amino acid residues, and 6.0% for the length of 15 amino acid residues, and wherein:

the 7 residue length of the antibody HC-CDR3 region and the position proceeding the antibody HC-CDR region encoded by the library of DNA expression vectors are encoded by the relative frequencies of amino acids at Kabat positions 94, 95, 96, 97, 98, 99, 101 and 102 as defined in Table 3A;

the 8 residue length of the antibody HC-CDR3 region and the position proceeding the antibody HC-CDR region encoded by the library of DNA expression vectors are encoded by the relative frequencies of amino acids at Kabat positions 94, 95, 96, 97, 98, 99, 100, 101 and 102 as defined in Table 3B;

the 9 residue length of the antibody HC-CDR3 region and the position proceeding the antibody HC-CDR region encoded by the library of DNA expression vectors are encoded by the relative frequencies of amino acids at Kabat positions 94, 95, 96, 97, 98, 99, 100, 100A, 101 and 102 as defined in Table 3C;

the 10 residue length of the antibody HC-CDR3 region and the position proceeding the antibody HC-CDR region encoded by the library of DNA expression vectors are encoded by the relative frequencies of amino acids at Kabat positions 94, 95, 96, 97, 98, 99, 100, 100A, 100B, 101 and 102 as defined in Table 3D;

the 11 residue length of the antibody HC-CDR3 region and the position proceeding the antibody HC-CDR region encoded by the library of DNA expression vectors are encoded by the relative frequencies of amino acids at Kabat positions 94, 95, 96, 97, 98, 99, 100, 100A, 100B, 100C, 101 and 102 as defined in Table 3E;

the 12 residue length of the antibody HC-CRD3 region and the position proceeding the antibody HC-CDR region encoded by the library of DNA expression vectors are encoded by the relative frequencies of amino acids at Kabat positions 94, 95, 96, 97, 98, 99, 100, 100A, 100B, 100C, 100D, 101 and 102 as defined in Table 3F;

the 13 residue length of the antibody HC-CDR3 region and the position proceeding the antibody HC-CDR region encoded by the library of DNA expression vectors is encoded by the relative frequencies of amino acids at Kabat positions 94, 95, 96, 97, 98, 99, 100, 100A, 100B, 100C, 100D, 100E, 101 and 102 as defined in Table 3G;

the 14 residue length of the antibody HC-CDR3 region and the position proceeding the antibody HC-CDR region encoded by the library of DNA expression vectors is encoded by the relative frequenies of amino acids at Kabat positions 94, 95, 96, 97, 98, 99, 100, 100A, 100B, 100C, 100D, 100E, 100F, 101 and 102 as defined in Table 3H; and the 15 residue length of the antibody HC-CDR3 region and the position proceeding the antibody HC-CDR region encoded by the library of DNA expression vectors is encoded by the relative frequencies of amino acids at Kabat positions 94 95, 96, 97, 98, 99, 100, 100A, 100B, 100C, 100D, 100E, 100F, 100G, 101 and 102 as defined in Table 3I.

2. A library of DNA expression vectors according to claim 1, wherein the antibody or functional fragment thereof is a single-chain antibody, a Fab fragment, a heavy chain only antibody or a variable heavy chain only domain.

3. A library of DNA expression vectors according to claim 1, wherein the antibodies or functional fragments thereof comprise human antibody germline variable segments.

4. A library of DNA expression vectors according to claim 1, wherein the antibodies or functional fragments thereof comprise a human antibody VK1 light chain variable domain containing human germline sequences and a human antibody VH3 heavy chain variable domain containing human germline sequences.

5. A library of DNA expression vectors according to claim 4, wherein the VK1 kappa light chain variable domain contains the human germline sequences SEQ ID NO: 3 and SEQ ID NO. 4, the light chain CDR3 region contains the sequence SEQ ID NO: 5 and the VH3 heavy chain variable domain contains the human germline sequences SEQ ID NO: 1 and SEQ ID NO: 2.

6. A library of DNA expression vectors according to claim 4, wherein the VH3 heavy chain variable domain comprising the human germline sequences is connected to a human antibody VK1 kappa light chain variable domain comprising the human germline sequences with a linker of SEQ ID NO: 6.

7. A library of DNA expression vectors according to claim 1, wherein the DNA expression vector comprises both a DNA backbone and DNA encoding the antibodies or functional fragments thereof, where the DNA backbone is encoded by SEQ ID NO: 8.

* * * * *

SEQUENCE LISTING

```
<160> NUMBER OF SEQ ID NOS: 168

<210> SEQ ID NO 1
<211> LENGTH: 97
<212> TYPE: PRT
<213> ORGANISM: Homo sapiens
<220> FEATURE:
<223> OTHER INFORMATION: Heavy chain VH3 translated germline segment
      V3-23

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala

<210> SEQ ID NO 2
<211> LENGTH: 11
<212> TYPE: PRT
<213> ORGANISM: Homo sapiens
<220> FEATURE:
<223> OTHER INFORMATION: Heavy chain translated J4 germline segment

<400> SEQUENCE: 2

Trp Gly Gln Gly Thr Leu Val Thr Val Ser Ser
1               5                   10
```

<210> SEQ ID NO 3
<211> LENGTH: 88
<212> TYPE: PRT
<213> ORGANISM: Homo sapiens
<220> FEATURE:
<223> OTHER INFORMATION: Kappa light chain VK1 translated germline
      segment

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys
                85

<210> SEQ ID NO 4
<211> LENGTH: 11
<212> TYPE: PRT
<213> ORGANISM: Homo sapiens
<220> FEATURE:
<223> OTHER INFORMATION: Kappa light chain VK1 translated germline
      segment J1

<400> SEQUENCE: 4

Phe Gly Gln Gly Thr Lys Val Glu Ile Lys Arg
1               5                   10

<210> SEQ ID NO 5
<211> LENGTH: 9
<212> TYPE: PRT
<213> ORGANISM: Homo sapiens
<220> FEATURE:
<223> OTHER INFORMATION: Kappa light chain CDR3

<400> SEQUENCE: 5

Gln Gln Ser Tyr Ser Thr Pro Leu Thr
1               5

<210> SEQ ID NO 6
<211> LENGTH: 15
<212> TYPE: PRT
<213> ORGANISM: Homo sapiens
<220> FEATURE:
<223> OTHER INFORMATION: VH/VL linker

<400> SEQUENCE: 6

Gly Gly Gly Gly Ser Gly Gly Gly Gly Ser Gly Gly Gly Gly Ser
1               5                   10                  15

<210> SEQ ID NO 7
<211> LENGTH: 1032
<212> TYPE: DNA
<213> ORGANISM: Homo sapiens
<220> FEATURE:
<221> NAME/KEY: source
<222> LOCATION: 1..1032
<223> OTHER INFORMATION: /mol_type="unassigned DNA"

/note="Scaffold including stuffer"
/organism="Homo sapiens"

<400> SEQUENCE: 7

| | | | | | |
|---|---|---|---|---|---|
| gaagttcagc | tgctggaatc | tggtggtggt | ctggttcagc | cgggtggttc | tctgcgtctg | 60 |
| tcttgcgctg | cttctggttt | caccttctct | tcttacgcta | tgtcttgggt | tcgtcaggct | 120 |
| ccgggtaaag | gtctggaatg | ggttctgctg | atctctggtt | ctggtggttc | tacctactac | 180 |
| gctgactctg | ttaaaggtcg | tttcaccatc | tctcgtgaca | actctaaaaa | caccctgtac | 240 |
| ctgcaaatga | actctctgcg | tgctgaagac | actgcagggc | actaaatatg | taacacactc | 300 |
| aatatcaaca | tgacctcaaa | cacaggctct | tacaaaggta | agaaatttt | tagttatgga | 360 |
| aaattgagct | atgctaattg | ttcccatagt | ggaagtttga | actgaagtcg | tgcgcagaac | 420 |
| atcaagggca | gtagaaactt | tctatatcac | gcaaggacat | cgatatcgaa | gcccgtaccg | 480 |
| tgagaacttt | ttcagtacgg | caaagtatac | taggcctatt | gcccttttcg | taacttgtgc | 540 |
| gtattctctt | tcatcactgt | tcacaaccag | taccttgtcc | tcaaaaggtc | atcacgttta | 600 |
| tttaaattcc | cattcgaaag | gcatacatcg | tagtgccaag | gcacactcgt | taccgtctca | 660 |
| agtggtggcg | gaggatccgg | aggaggtggc | tctggaggtg | gcggttcaga | catccagatg | 720 |
| acccagtctc | cgtcttctct | gtctgctagc | gttggcgatc | gtgttaccat | cacctgccgt | 780 |
| gcttctcagt | ctatctcttc | ttacctgaac | tggtatcagc | agaaacccgg | aaagctccg | 840 |
| aaactgctga | tctacgctgc | ttcttctctt | cagtctggtg | ttccgtctcg | tttctctggt | 900 |
| tctggttctg | gcaccgactt | caccctgacc | atctcgagcc | ttcagccgga | agacttcgct | 960 |
| acctactact | gccagcagtc | ttactctacc | ccgctgacct | tcggtcaggg | taccaaagtt | 1020 |
| gaaatcaaac | gt | | | | | 1032 |

<210> SEQ ID NO 8
<211> LENGTH: 5540
<212> TYPE: DNA
<213> ORGANISM: Homo sapiens
<220> FEATURE:
<221> NAME/KEY: source
<222> LOCATION: 1..5540
<223> OTHER INFORMATION: /mol_type="other DNA"
    /note="Base vector VH3_VK1_v22"
    /organism="Homo sapiens"

<400> SEQUENCE: 8

| | | | | | |
|---|---|---|---|---|---|
| gacgaaaggg | cctcgtgata | cgcctatttt | tataggttaa | tgtcatgata | ataatggttt | 60 |
| cttagacgtc | aggtggcact | tttcggggaa | atgtgcgcgg | aacccctatt | tgtttatttt | 120 |
| tctaaataca | ttcaaatatg | tatccgctca | tgagacaata | accctgataa | atgcttcaat | 180 |
| aatattgaaa | aaggaagagt | atgagtattc | aacatttccg | tgtcgccctt | attccctttt | 240 |
| ttgcggcatt | ttgccttcct | gtttttgctc | acccagaaac | gctggtgaaa | gtaaaagatg | 300 |
| ctgaagatca | gttgggtgcc | cgagtgggtt | acatcgaact | ggatctcaac | agcggtaaga | 360 |
| tccttgagag | ttttcgcccc | gaagaacgtt | ttccaatgat | gagcactttt | aaagttctgc | 420 |
| tatgtggcgc | ggtattatcc | cgtattgacg | ccgggcaaga | gcaactcggt | cgccgcatac | 480 |
| actattctca | gaatgacttg | gttgagtact | caccagtcac | agaaaagcat | cttacggatg | 540 |
| gcatgacagt | aagagaatta | tgcagtgctg | ccataaccat | gagtgataac | actgcggcca | 600 |
| acttacttct | gacaaccatc | ggaggaccga | aggagctaac | cgcttttttg | cacaacatgg | 660 |
| gggatcatgt | aactcgcctt | gatcgttggg | aaccggagct | gaatgaagcc | ataccaaacg | 720 |

```
acgagcgtga caccacgatg cctgtagcaa tggcaacaac gttgcgcaaa ctattaactg    780
gcgaactact tactctagct tcccggcaac aattaataga ctggatggag gcggataaag    840
ttgcaggacc acttctgcgc tcggcccttc cggctggctg gtttattgct gataaatctg    900
gagccggtga gcgtgggtct cgcggtatca ttgcagcact ggggccagat ggtaagccct    960
cccgtatcgt agttatctac acgacgggga gtcaggcaac tatggatgaa cgaaatagac   1020
agatcgctga gataggtgcc tcactgatta agcattggta actgtcagac caagtttact   1080
catatatact ttagattgat ttaaaacttc attttttaatt taaaaggatc taggtgaaga   1140
tcctttttga taatctcatg accaaaatcc cttaacgtga gttttcgttc cactgagcgt   1200
cagaccccgt agaaaagatc aaaggatctt cttgagatcc ttttttttctg cgcgtaatct   1260 gctgcttgca acaaaaaaaa ccaccgctac cagcggtggt ttgtttgccg gatcaagagc   1320
taccaactct tttttccgaag gtaactggct tcagcagagc gcagatacca aatactgtcc   1380
ttctagtgta gccgtagtta ggccaccact tcaagaactc tgtagcaccg cctacatacc   1440
tcgctctgct aatcctgtta ccagtggctg ctgccagtgg cgataagtcg tgtcttaccg   1500
ggttggactc aagacgatag ttaccggata aggcgcagcg tcgggctgaa cggggggtt   1560 cgtgcataca gcccagcttg gagcgaacga cctacaccga actgagatac ctacagcgtg   1620
agcattgaga aagcgccacg cttcccgaag ggagaaaggc ggacaggtat ccggtaagcg   1680
gcagggtcgg aacaggagag cgcacgaggg agcttccagg gggaaacgcc tggtatcttt   1740
atagtcctgt cgggtttcgc cacctctgac ttgagcgtcg attttttgtga tgctcgtcag   1800 gggggcggag cctatggaaa aacgccagca acgcggcctt tttacggttc ctggccttt    1860 gctggccttt tgctcacatg ttctttcctg cgttatcccc tgattctgtg gataaccgta    1920
ttaccgcctt tgagtgagct gataccgctc gccgcagccg aacgaccgag cgcagcgagt   1980
cagtgagcga ggaagcggaa gagcgcccaa tacgcaaacc gcctctcccc gcgcgttggc   2040
cgattcatta atgcagctgg cacgacaggt ttcccgactg gaaagcgggc agtgagcgca   2100
acgcaattaa tgtgagttag ctcactcatt aggcacccca ggctttacac tttatgcttc   2160
cggctcgtat gttgtgtgga attgtgagcg gataacaatt tcacacagga aacagctatg   2220
accatgatta cgccaagctt tggagccttt ttttttggaga ttttcaacgt gaaaaaatta   2280
ttattcgcaa ttccttttagt tgttcctttc tatgcggccc agccggcgat ggccgaagtt   2340
cagctgctgg aatctggtgg tggtctggtt cagccgggtg gttctctgcg tctgtcttgc   2400
gctgcttctg gtttcacctt ctcttcttac gctatgtctt gggttcgtca ggctccgggt   2460
aaaggtctgg aatgggtttc tgctatctct ggttctggtg gttctaccta ctacgctgac   2520
tctgttaaag gtcgtttcac catctctcgt gacaactcta aaaacacccct gtacctgcaa   2580 atgaactctc tgcgtgctga agacactgca gggcactaaa tatgtaacac actcaatatc   2640
aacatgacct caaacacagg ctcttacaaa ggtagaagaa attttagtta tggaaaattg   2700
agctatgcta attgttccca tagtggaagt ttgaactgaa gtcgtgcgca gaacatcaag   2760
ggcagtagaa actttctata tcacgcaagg acatcgatat cgaagcccgt accgtgagaa   2820 cttttttcagt acggcaaagt atactaggcc tattgccctt ttcgtaactt gtgcgtattc   2880
tctttcatca ctgttcacaa ccagtacctt gtcctcaaaa ggtcatcacg tttatttaaa   2940
ttcccattcg aaaggcatac atcgtagtgc caaggcacac tcgttaccgt ctcaagtggt   3000
ggcggaggat ccgaggagg tggctctgga ggtggcggtt cagacatcca gatgacccag   3060
tctccgtctt ctctgtctgc tagcgttggc gatcgtgtta ccatcacctg ccgtgcttct   3120
```

```
cagtctatct cttcttacct gaactggtat cagcagaaac ccgggaaagc tccgaaactg    3180
ctgatctacg ctgcttcttc tcttcagtct ggtgttccgt ctcgtttctc tggttctggt    3240
tctggcaccg acttcaccct gaccatctcg agccttcagc cggaagactt cgctacctac    3300
tactgccagc agtcttactc taccccgctg accttcggtc agggtaccaa agttgaaatc    3360
aaacgtgcgg ccgcacatca tcatcaccat cacggggccg cagaacaaaa actcatctca    3420
gaagaggatc tgaatggggc cgcatagact gttgaaagtt gtttagcaaa acctcataca    3480
gaaaattcat ttactaacgt ctggaaagac gacaaaactt tagatcgtta cgctaactat    3540
gagggctgtc tgtggaatgc tacaggcgtt gtggtttgta ctggtgacga aactcagtgt    3600
tacggtacat gggttcctat tgggcttgct atccctgaaa atgagggtgg tggctctgag    3660
ggtggcggtt ctgaggggtgg cggttctgag ggtggcggta ctaaacctcc tgagtacggt    3720
```

-continued

```
atccgcttac agacaagctg tgaccgtctc cgggagctgc atgtgtcaga ggttttcacc    5520
gtcatcaccg aaacgcgcga                                                5540
```

<210> SEQ ID NO 9
<211> LENGTH: 15
<212> TYPE: DNA
<213> ORGANISM: Homo sapiens
<220> FEATURE:
<221> NAME/KEY: source
<222> LOCATION: 1..15
<223> OTHER INFORMATION: /mol_type="other DNA"
      /note="Sty_rev_1"
      /organism="Homo sapiens"

<400> SEQUENCE: 9

```
ccgaccttgg cccca                                                     15
```

<210> SEQ ID NO 10
<211> LENGTH: 27
<212> TYPE: DNA
<213> ORGANISM: Homo sapiens
<220> FEATURE:
<221> NAME/KEY: source
<222> LOCATION: 1..27
<223> OTHER INFORMATION: /mol_type="other DNA"
      /note="PstI_for _1 primer"
      /organism="Homo sapiens"

<400> SEQUENCE: 10

```
cgaaaagcac ctgcagtgta ttactgc                                        27
```

<210> SEQ ID NO 11
<211> LENGTH: 19
<212> TYPE: DNA
<213> ORGANISM: Homo sapiens
<220> FEATURE:
<221> NAME/KEY: source
<222> LOCATION: 1..19
<223> OTHER INFORMATION: /mol_type="other DNA"
      /note="Sty_rev_2 primer"
      /organism="Homo sapiens"

<400> SEQUENCE: 11

```
ctgaccgacc tgggcccca                                                 19
```

<210> SEQ ID NO 12
<211> LENGTH: 17
<212> TYPE: PRT
<213> ORGANISM: Homo sapiens

<400> SEQUENCE: 12

Cys Ala Arg Asp Pro Leu Asp Ile Tyr Ser Trp Gly Tyr Phe Asp Tyr
1               5                   10                  15

Trp

<210> SEQ ID NO 13
<211> LENGTH: 14
<212> TYPE: PRT
<213> ORGANISM: Homo sapiens

<400> SEQUENCE: 13

Cys Ala Val Val Thr Gly Val Leu Trp Gly Phe Asp Tyr Trp
1               5                   10

<210> SEQ ID NO 14
<211> LENGTH: 15

```
<212> TYPE: PRT
<213> ORGANISM: Homo sapiens

<400> SEQUENCE: 14

Cys Ala Lys Asp Tyr Ala Ser Gly Tyr Gly Tyr Phe Asp Tyr Trp
1               5                   10                  15

<210> SEQ ID NO 15
<211> LENGTH: 15
<212> TYPE: PRT
<213> ORGANISM: Homo sapiens

<400> SEQUENCE: 15

Cys Ala Lys Asp Tyr Ala Ser Gly Trp Gly Tyr Phe Asp Tyr Trp
1               5                   10                  15

<210> SEQ ID NO 16
<211> LENGTH: 15
<212> TYPE: PRT
<213> ORGANISM: Homo sapiens

<400> SEQUENCE: 16

Cys Ala Lys Asp Phe Gly Arg Gly Tyr Gly Tyr Phe Asp Tyr Trp
1               5                   10                  15

<210> SEQ ID NO 17
<211> LENGTH: 15
<212> TYPE: PRT
<213> ORGANISM: Homo sapiens

<400> SEQUENCE: 17

Cys Ala Lys Asp Phe Arg Ser Gly Tyr Gly Tyr Phe Asp Tyr Trp
1               5                   10                  15

<210> SEQ ID NO 18
<211> LENGTH: 15
<212> TYPE: PRT
<213> ORGANISM: Homo sapiens

<400> SEQUENCE: 18

Cys Ala Gln Asp Val Arg Arg Gly Cys Gly Tyr Phe Asp Tyr Trp
1               5                   10                  15

<210> SEQ ID NO 19
<211> LENGTH: 15
<212> TYPE: PRT
<213> ORGANISM: Homo sapiens

<400> SEQUENCE: 19

Cys Ala Lys Asp Val Ala Arg Gly Tyr Gly Tyr Phe Asp Tyr Trp
1               5                   10                  15

<210> SEQ ID NO 20
<211> LENGTH: 15
<212> TYPE: PRT
<213> ORGANISM: Homo sapiens

<400> SEQUENCE: 20

Cys Ala Lys Asp Val Trp Arg Gly Tyr Gly Tyr Phe Asp Tyr Trp
1               5                   10                  15

<210> SEQ ID NO 21
<211> LENGTH: 15
<212> TYPE: PRT
```

-continued

```
<400> SEQUENCE: 21

Cys Ala Lys Asp Val Gly Arg Gly Val Gly Tyr Phe Asp Tyr Trp
1               5                   10                  15

<210> SEQ ID NO 22
<211> LENGTH: 15
<212> TYPE: PRT
<213> ORGANISM: Homo sapiens

<400> SEQUENCE: 22

Cys Ala Lys Val Val Gly Gly Val Leu Tyr Ala Phe Asp Tyr Trp
1               5                   10                  15

<210> SEQ ID NO 23
<211> LENGTH: 18
<212> TYPE: PRT
<213> ORGANISM: Homo sapiens

<400> SEQUENCE: 23

Cys Ala Arg Gly Ala Gly Tyr Tyr Gly Leu Pro Val Tyr Ala Phe Asp
1               5                   10                  15

Tyr Trp

<210> SEQ ID NO 24
<211> LENGTH: 18
<212> TYPE: PRT
<213> ORGANISM: Homo sapiens

<400> SEQUENCE: 24

Cys Ala Arg Gly Ala Gly Tyr Ser Gly Leu Pro Val Tyr Ala Phe Asp
1               5                   10                  15

Tyr Trp

<210> SEQ ID NO 25
<211> LENGTH: 18
<212> TYPE: PRT
<213> ORGANISM: Homo sapiens

<400> SEQUENCE: 25

Cys Ala Arg Gly Ala Gly Tyr Leu Gly Tyr Pro Val Tyr Ala Phe Asp
1               5                   10                  15

Tyr Trp

<210> SEQ ID NO 26
<211> LENGTH: 15
<212> TYPE: PRT
<213> ORGANISM: Homo sapiens

<400> SEQUENCE: 26

Cys Ala Arg Ala Asn Trp Ala Ser Ser Tyr Glu Phe Asp Tyr Trp
1               5                   10                  15

<210> SEQ ID NO 27
<211> LENGTH: 17
<212> TYPE: PRT
<213> ORGANISM: Homo sapiens

<400> SEQUENCE: 27

Cys Ala Arg Val Gly Arg Tyr Gly Tyr Tyr Asp Ala Ala Phe Asp Tyr
1               5                   10                  15

Trp
```

<210> SEQ ID NO 28
<211> LENGTH: 14
<212> TYPE: PRT
<213> ORGANISM: Homo sapiens

<400> SEQUENCE: 28

Cys Ala Arg Glu Gly Asp Pro Asp Leu Tyr Phe Phe Asp Tyr
1               5                   10

<210> SEQ ID NO 29
<211> LENGTH: 14
<212> TYPE: PRT
<213> ORGANISM: Homo sapiens

<400> SEQUENCE: 29

Cys Ala Arg Gly Tyr Ala Trp Pro Ser Trp Phe Asp Tyr Trp
1               5                   10

<210> SEQ ID NO 30
<211> LENGTH: 14
<212> TYPE: PRT
<213> ORGANISM: Homo sapiens

<400> SEQUENCE: 30

Cys Ala Arg Glu Trp Trp Asp Tyr Leu Tyr Leu Asp Tyr Trp
1               5                   10

<210> SEQ ID NO 31
<211> LENGTH: 10
<212> TYPE: PRT
<213> ORGANISM: Homo sapiens

<400> SEQUENCE: 31

Cys Ala Ser Gly Asp Tyr Trp Gly Gln Gly
1               5                   10

<210> SEQ ID NO 32
<211> LENGTH: 11
<212> TYPE: PRT
<213> ORGANISM: Homo sapiens

<400> SEQUENCE: 32

Cys Ala Thr Asn Asp Asp Tyr Trp Gly Gln Gly
1               5                   10

<210> SEQ ID NO 33
<211> LENGTH: 12
<212> TYPE: PRT
<213> ORGANISM: Homo sapiens

<400> SEQUENCE: 33

Cys Ala Thr Glu Leu Phe Asp Leu Trp Gly Gln Gly
1               5                   10

<210> SEQ ID NO 34
<211> LENGTH: 12
<212> TYPE: PRT
<213> ORGANISM: Homo sapiens

<400> SEQUENCE: 34

Cys Ala Arg Glu Gly Ile Tyr Trp Trp Gly Arg Gly
1               5                   10

```
<210> SEQ ID NO 35
<211> LENGTH: 12
<212> TYPE: PRT
<213> ORGANISM: Homo sapiens

<400> SEQUENCE: 35

Cys Val Lys Pro Gly Gly Asp Tyr Trp Gly Gln Gly
1               5                   10

<210> SEQ ID NO 36
<211> LENGTH: 12
<212> TYPE: PRT
<213> ORGANISM: Homo sapiens

<400> SEQUENCE: 36

Cys Lys Arg Ser Tyr Tyr Gly His Trp Gly His Gly
1               5                   10

<210> SEQ ID NO 37
<211> LENGTH: 13
<212> TYPE: PRT
<213> ORGANISM: Homo sapiens

<400> SEQUENCE: 37

Cys Lys Thr His Gly Ser His Asp Asn Arg Gly Gln Gly
1               5                   10

<210> SEQ ID NO 38
<211> LENGTH: 13
<212> TYPE: PRT
<213> ORGANISM: Homo sapiens

<400> SEQUENCE: 38

Cys Glu Arg Glu Gly Gly Val Asn Asn Trp Gly Gln Gly
1               5                   10

<210> SEQ ID NO 39
<211> LENGTH: 13
<212> TYPE: PRT
<213> ORGANISM: Homo sapiens

<400> SEQUENCE: 39

Cys Ala Arg Ser Pro Ser Gly Phe Asn Trp Gly Gln Gly
1               5                   10

<210> SEQ ID NO 40
<211> LENGTH: 14
<212> TYPE: PRT
<213> ORGANISM: Homo sapiens

<400> SEQUENCE: 40

Cys Ala Arg Arg Gln Leu Tyr Phe Asp Tyr Trp Gly Gln Gly
1               5                   10

<210> SEQ ID NO 41
<211> LENGTH: 14
<212> TYPE: PRT
<213> ORGANISM: Homo sapiens

<400> SEQUENCE: 41

Cys Ala Gln Asn Leu Glu Ile Pro Arg Thr Phe Gly Gln Gly
1               5                   10

<210> SEQ ID NO 42
<211> LENGTH: 14
```

<212> TYPE: PRT
<213> ORGANISM: Homo sapiens

<400> SEQUENCE: 42

Cys Ala Arg Gly Gly Gly Val Phe Asp Tyr Trp Gly Gln Gly
1               5                   10

<210> SEQ ID NO 43
<211> LENGTH: 14
<212> TYPE: PRT
<213> ORGANISM: Homo sapiens

<400> SEQUENCE: 43

Cys Ala Gln Asn Leu Glu Ile Pro Arg Thr Phe Gly Gln Gly
1               5                   10

<210> SEQ ID NO 44
<211> LENGTH: 14
<212> TYPE: PRT
<213> ORGANISM: Homo sapiens

<400> SEQUENCE: 44

Cys Ala Ser Leu Tyr Ser Leu Pro Val Tyr Trp Gly Gln Gly
1               5                   10

<210> SEQ ID NO 45
<211> LENGTH: 14
<212> TYPE: PRT
<213> ORGANISM: Homo sapiens

<400> SEQUENCE: 45

Cys Ala Lys Pro Phe Pro Tyr Phe Asp Tyr Trp Gly Gln Gly
1               5                   10

<210> SEQ ID NO 46
<211> LENGTH: 14
<212> TYPE: PRT
<213> ORGANISM: Homo sapiens

<400> SEQUENCE: 46

Cys Ala Arg Val Thr Asp Ala Phe Asp Ile Trp Gly Gln Gly
1               5                   10

<210> SEQ ID NO 47
<211> LENGTH: 14
<212> TYPE: PRT
<213> ORGANISM: Homo sapiens

<400> SEQUENCE: 47

Cys Ala Lys Gly Arg Asp Ser Phe Asp Ile Trp Gly Gln Gly
1               5                   10

<210> SEQ ID NO 48
<211> LENGTH: 14
<212> TYPE: PRT
<213> ORGANISM: Homo sapiens

<400> SEQUENCE: 48

Cys Ala Arg Asp Pro Ile Ala Ala Gly Tyr Trp Gly Gln Gly
1               5                   10

<210> SEQ ID NO 49
<211> LENGTH: 14
<212> TYPE: PRT
<213> ORGANISM: Homo sapiens

<400> SEQUENCE: 49

Cys Ala Arg Asn Trp Met Asn Phe Asp Tyr Trp Gly Gln Gly
1               5                   10

<210> SEQ ID NO 50
<211> LENGTH: 15
<212> TYPE: PRT
<213> ORGANISM: Homo sapiens

<400> SEQUENCE: 50

Cys Val Arg Ile Gly Glu Asp Ala Leu Asp Tyr Trp Gly Gln Gly
1               5                   10                  15

<210> SEQ ID NO 51
<211> LENGTH: 15
<212> TYPE: PRT
<213> ORGANISM: Homo sapiens

<400> SEQUENCE: 51

Cys Ser Arg Asp Tyr Gly Tyr Tyr Phe Asp Phe Trp Gly Gln Gly
1               5                   10                  15

<210> SEQ ID NO 52
<211> LENGTH: 15
<212> TYPE: PRT
<213> ORGANISM: Homo sapiens

<400> SEQUENCE: 52

Cys Ala Asn Tyr Gly Asn Tyr Trp Phe Ala Tyr Trp Gly Gln Gly
1               5                   10                  15

<210> SEQ ID NO 53
<211> LENGTH: 15
<212> TYPE: PRT
<213> ORGANISM: Homo sapiens

<400> SEQUENCE: 53

Cys Ala Arg Trp Gly Arg Val Phe Phe Asp Trp Trp Gly Gln Gly
1               5                   10                  15

<210> SEQ ID NO 54
<211> LENGTH: 15
<212> TYPE: PRT
<213> ORGANISM: Homo sapiens

<400> SEQUENCE: 54

Cys Thr Gly Tyr Tyr Ala Asp Ala Met Asp Tyr Trp Gly Gln Gly
1               5                   10                  15

<210> SEQ ID NO 55
<211> LENGTH: 15
<212> TYPE: PRT
<213> ORGANISM: Homo sapiens

<400> SEQUENCE: 55

Cys Ala Arg His Leu His Gly Ser Phe Ala Ser Trp Gly Gln Gly
1               5                   10                  15

<210> SEQ ID NO 56
<211> LENGTH: 15
<212> TYPE: PRT
<213> ORGANISM: Homo sapiens

<400> SEQUENCE: 56

```
Cys Ala Arg Asp Arg Tyr Tyr Gly Pro Glu Met Trp Gly Gln Gly
1               5                   10                  15

<210> SEQ ID NO 57
<211> LENGTH: 15
<212> TYPE: PRT
<213> ORGANISM: Homo sapiens

<400> SEQUENCE: 57

Cys Ala Arg Asp Asn Trp Asp Ala Met Asp Tyr Trp Gly Gln Gly
1               5                   10                  15

<210> SEQ ID NO 58
<211> LENGTH: 15
<212> TYPE: PRT
<213> ORGANISM: Homo sapiens

<400> SEQUENCE: 58

Cys Ala Ser Trp Ile Ser Asp Phe Phe Asp Tyr Trp Gly Gln Gly
1               5                   10                  15

<210> SEQ ID NO 59
<211> LENGTH: 15
<212> TYPE: PRT
<213> ORGANISM: Homo sapiens

<400> SEQUENCE: 59

Cys Gly Arg Ser Lys Arg Asp Tyr Phe Asp Tyr Trp Gly Gln Gly
1               5                   10                  15

<210> SEQ ID NO 60
<211> LENGTH: 16
<212> TYPE: PRT
<213> ORGANISM: Homo sapiens

<400> SEQUENCE: 60

Cys Ala Lys Asp Ser Asn Trp Gly Asn Phe Asp Leu Trp Gly Arg Gly
1               5                   10                  15

<210> SEQ ID NO 61
<211> LENGTH: 16
<212> TYPE: PRT
<213> ORGANISM: Homo sapiens

<400> SEQUENCE: 61

Cys Ala Thr Gly Asp Thr Thr Tyr Lys Phe Asp Phe Trp Gly Gln Gly
1               5                   10                  15

<210> SEQ ID NO 62
<211> LENGTH: 16
<212> TYPE: PRT
<213> ORGANISM: Homo sapiens

<400> SEQUENCE: 62

Cys Ala Arg Asp Leu Arg Thr Gly Pro Phe Asp Tyr Trp Gly Gln Gly
1               5                   10                  15

<210> SEQ ID NO 63
<211> LENGTH: 16
<212> TYPE: PRT
<213> ORGANISM: Homo sapiens

<400> SEQUENCE: 63

Cys Ala Arg Thr Gly Ser Ser Gly Tyr Phe Asp Phe Trp Gly Gln Gly
```

```
1               5                   10                  15
```

<210> SEQ ID NO 64
<211> LENGTH: 16
<212> TYPE: PRT
<213> ORGANISM: Homo sapiens

<400> SEQUENCE: 64

```
Cys Ala Arg Asn Tyr Val Gly Ser Ile Phe Asp Tyr Trp Gly Gln Gly
1               5                   10                  15
```

<210> SEQ ID NO 65
<211> LENGTH: 16
<212> TYPE: PRT
<213> ORGANISM: Homo sapiens

<400> SEQUENCE: 65

```
Cys Ala Arg Gln Met Gly Tyr Trp His Phe Asp Leu Trp Gly Arg Gly
1               5                   10                  15
```

<210> SEQ ID NO 66
<211> LENGTH: 16
<212> TYPE: PRT
<213> ORGANISM: Homo sapiens

<400> SEQUENCE: 66

```
Cys Ala Arg Gly Tyr Asn Trp Asn Tyr Phe Asp Tyr Trp Gly Gln Gly
1               5                   10                  15
```

<210> SEQ ID NO 67
<211> LENGTH: 16
<212> TYPE: PRT
<213> ORGANISM: Homo sapiens

<400> SEQUENCE: 67

```
Cys Ala Arg Met Arg Lys Gly Tyr Ala Met Asp Tyr Trp Gly Gln Gly
1               5                   10                  15
```

<210> SEQ ID NO 68
<211> LENGTH: 16
<212> TYPE: PRT
<213> ORGANISM: Homo sapiens

<400> SEQUENCE: 68

```
Cys Ala Arg Glu Ser Tyr Tyr Gly Phe Thr Ser Tyr Trp Gly Gln Gly
1               5                   10                  15
```

<210> SEQ ID NO 69
<211> LENGTH: 15
<212> TYPE: PRT
<213> ORGANISM: Homo sapiens

<400> SEQUENCE: 69

```
Cys Ser Arg Pro Thr Met Leu Pro Trp Phe Ala Tyr Trp Gly Gln
1               5                   10                  15
```

<210> SEQ ID NO 70
<211> LENGTH: 16
<212> TYPE: PRT
<213> ORGANISM: Homo sapiens

<400> SEQUENCE: 70

```
Cys Ala Arg Asp Lys Trp Thr Trp Tyr Phe Asp Leu Trp Gly Arg Gly
1               5                   10                  15
```

```
<210> SEQ ID NO 71
<211> LENGTH: 16
<212> TYPE: PRT
<213> ORGANISM: Homo sapiens

<400> SEQUENCE: 71

Cys Ser Arg Gly Ile Pro Gly Tyr Ala Met Asp Tyr Trp Gly Gln Gly
1               5                   10                  15

<210> SEQ ID NO 72
<211> LENGTH: 16
<212> TYPE: PRT
<213> ORGANISM: Homo sapiens

<400> SEQUENCE: 72

Cys Ala Arg Glu Leu Gly Arg Arg Tyr Phe Asp Leu Trp Gly Arg Gly
1               5                   10                  15

<210> SEQ ID NO 73
<211> LENGTH: 16
<212> TYPE: PRT
<213> ORGANISM: Homo sapiens

<400> SEQUENCE: 73

Cys Ala Arg Tyr Asp Tyr Asn Tyr Ala Met Asp Tyr Trp Gly Gln Gly
1               5                   10                  15

<210> SEQ ID NO 74
<211> LENGTH: 16
<212> TYPE: PRT
<213> ORGANISM: Homo sapiens

<400> SEQUENCE: 74

Cys Ala Arg Asp Tyr Gly Asp Tyr Gly Met Asp Tyr Trp Gly Gln Gly
1               5                   10                  15

<210> SEQ ID NO 75
<211> LENGTH: 17
<212> TYPE: PRT
<213> ORGANISM: Homo sapiens

<400> SEQUENCE: 75

Cys Ala Arg Tyr Tyr Asp Asp His Tyr Cys Leu Asp Tyr Trp Gly Gln
1               5                   10                  15

Gly

<210> SEQ ID NO 76
<211> LENGTH: 17
<212> TYPE: PRT
<213> ORGANISM: Homo sapiens

<400> SEQUENCE: 76

Cys Ala Arg Gly Glu Gly Asn Tyr Ala Trp Phe Ala Tyr Trp Gly Gln
1               5                   10                  15

Gly

<210> SEQ ID NO 77
<211> LENGTH: 17
<212> TYPE: PRT
<213> ORGANISM: Homo sapiens

<400> SEQUENCE: 77

Cys Val Arg Pro Leu Tyr Asp Tyr Tyr Ala Met Asp Tyr Trp Gly Gln
```

```
1               5                   10                  15
Gly

<210> SEQ ID NO 78
<211> LENGTH: 17
<212> TYPE: PRT
<213> ORGANISM: Homo sapiens

<400> SEQUENCE: 78

Cys Ala Arg Asn Val Phe Asp Gly Tyr Trp Leu Val Tyr Trp Gly Gln
1               5                   10                  15

Gly

<210> SEQ ID NO 79
<211> LENGTH: 17
<212> TYPE: PRT
<213> ORGANISM: Homo sapiens

<400> SEQUENCE: 79

Cys Ala Arg Glu Gly His Thr Ala Ala Pro Phe Asp Tyr Trp Gly Gln
1               5                   10                  15

Gly

<210> SEQ ID NO 80
<211> LENGTH: 17
<212> TYPE: PRT
<213> ORGANISM: Homo sapiens

<400> SEQUENCE: 80

Cys Ala Arg Gly Gly Tyr Asp Gly Arg Gly Phe Asp Tyr Trp Gly Ser
1               5                   10                  15

Gly

<210> SEQ ID NO 81
<211> LENGTH: 17
<212> TYPE: PRT
<213> ORGANISM: Homo sapiens

<400> SEQUENCE: 81

Cys Ala Arg Leu Asp Gly Tyr Tyr Phe Gly Phe Ala Tyr Trp Gly Gln
1               5                   10                  15

Gly

<210> SEQ ID NO 82
<211> LENGTH: 17
<212> TYPE: PRT
<213> ORGANISM: Homo sapiens

<400> SEQUENCE: 82

Cys Thr Arg Asp Arg Gly Leu Arg Phe Tyr Phe Asp Tyr Trp Gly Gln
1               5                   10                  15

Gly

<210> SEQ ID NO 83
<211> LENGTH: 17
<212> TYPE: PRT
<213> ORGANISM: Homo sapiens

<400> SEQUENCE: 83

Cys Ala Arg Arg Arg Asn Trp Gly Asn Ala Phe Asp Ile Trp Gly Gln
1               5                   10                  15
```

Gly

<210> SEQ ID NO 84
<211> LENGTH: 17
<212> TYPE: PRT
<213> ORGANISM: Homo sapiens

<400> SEQUENCE: 84

Cys Ala Arg Arg Gly Pro Tyr Asn Trp Tyr Phe Asp Val Trp Gly Gln
1               5                   10                  15

Gly

<210> SEQ ID NO 85
<211> LENGTH: 17
<212> TYPE: PRT
<213> ORGANISM: Homo sapiens

<400> SEQUENCE: 85

Cys Ala Arg Tyr Asp Gly Ile Tyr Gly Glu Leu Asp Phe Trp Gly Gln
1               5                   10                  15

Gly

<210> SEQ ID NO 86
<211> LENGTH: 17
<212> TYPE: PRT
<213> ORGANISM: Homo sapiens

<400> SEQUENCE: 86

Cys Ala Arg Gly Phe Gly Gly Ser Tyr Gly Phe Ala Tyr Trp Gly Gln
1               5                   10                  15

Gly

<210> SEQ ID NO 87
<211> LENGTH: 17
<212> TYPE: PRT
<213> ORGANISM: Homo sapiens

<400> SEQUENCE: 87

Cys Ala Arg Asp Tyr Asp Tyr Asp Val Gly Met Asp Tyr Trp Gly Gln
1               5                   10                  15

Gly

<210> SEQ ID NO 88
<211> LENGTH: 17
<212> TYPE: PRT
<213> ORGANISM: Homo sapiens

<400> SEQUENCE: 88

Cys Ala Arg Pro Asp Gly Asn Tyr Trp Tyr Phe Asp Val Trp Gly Gln
1               5                   10                  15

Gly

<210> SEQ ID NO 89
<211> LENGTH: 16
<212> TYPE: PRT
<213> ORGANISM: Homo sapiens

<400> SEQUENCE: 89

Cys Ala Arg His Gly Asp Asp Pro Ala Trp Phe Ala Tyr Trp Gly Gln
1               5                   10                  15

```
<210> SEQ ID NO 90
<211> LENGTH: 17
<212> TYPE: PRT
<213> ORGANISM: Homo sapiens

<400> SEQUENCE: 90

Cys Ser Thr Ile Phe Gly Val Val Thr Asn Phe Asp Asn Trp Gly Gln
1               5                   10                  15

Gly

<210> SEQ ID NO 91
<211> LENGTH: 17
<212> TYPE: PRT
<213> ORGANISM: Homo sapiens

<400> SEQUENCE: 91

Cys Ala Pro Arg Tyr Ser Ser Trp Tyr Leu Asp Tyr Trp Gly Gln
1               5                   10                  15

Gly

<210> SEQ ID NO 92
<211> LENGTH: 17
<212> TYPE: PRT
<213> ORGANISM: Homo sapiens

<400> SEQUENCE: 92

Cys Ala Lys Val Ala Val Ala Gly Thr His Phe Asp Tyr Trp Gly Gln
1               5                   10                  15

Gly

<210> SEQ ID NO 93
<211> LENGTH: 17
<212> TYPE: PRT
<213> ORGANISM: Homo sapiens

<400> SEQUENCE: 93

Cys Ala Arg Asn Arg Tyr Asp Pro Pro Trp Phe Val Asp Trp Gly Gln
1               5                   10                  15

Gly

<210> SEQ ID NO 94
<211> LENGTH: 17
<212> TYPE: PRT
<213> ORGANISM: Homo sapiens

<400> SEQUENCE: 94

Cys Ala Arg His Arg Ser Gly Tyr Phe Ser Met Asp Tyr Trp Gly Gln
1               5                   10                  15

Gly

<210> SEQ ID NO 95
<211> LENGTH: 17
<212> TYPE: PRT
<213> ORGANISM: Homo sapiens

<400> SEQUENCE: 95

Cys Ala Arg Glu Ala Arg Gly Ser Tyr Ala Phe Asp Ile Trp Gly Gln
1               5                   10                  15

Gly
```

```
<210> SEQ ID NO 96
<211> LENGTH: 17
<212> TYPE: PRT
<213> ORGANISM: Homo sapiens

<400> SEQUENCE: 96

Cys Ala Arg Arg Asp Tyr Asp Leu Asp Tyr Phe Asp Ser Trp Gly Gln
1               5                   10                  15

Gly

<210> SEQ ID NO 97
<211> LENGTH: 17
<212> TYPE: PRT
<213> ORGANISM: Homo sapiens

<400> SEQUENCE: 97

Cys Ala Arg Tyr Asp Tyr Phe Thr Gly Thr Gly Val Tyr Trp Gly Gln
1               5                   10                  15

Gly

<210> SEQ ID NO 98
<211> LENGTH: 17
<212> TYPE: PRT
<213> ORGANISM: Homo sapiens

<400> SEQUENCE: 98

Cys Ala Gly Asp Gly Tyr Tyr Pro Tyr Ala Met Asp Asn Trp Gly Gln
1               5                   10                  15

Gly

<210> SEQ ID NO 99
<211> LENGTH: 17
<212> TYPE: PRT
<213> ORGANISM: Homo sapiens

<400> SEQUENCE: 99

Cys Gly Arg His Ser Asp Gly Asn Phe Ala Phe Gly Tyr Trp Gly Gln
1               5                   10                  15

Gly

<210> SEQ ID NO 100
<211> LENGTH: 17
<212> TYPE: PRT
<213> ORGANISM: Homo sapiens

<400> SEQUENCE: 100

Cys Ala Arg Asp Met Ile Phe Asn Phe Tyr Phe Asp Val Trp Gly Gln
1               5                   10                  15

Gly

<210> SEQ ID NO 101
<211> LENGTH: 17
<212> TYPE: PRT
<213> ORGANISM: Homo sapiens

<400> SEQUENCE: 101

Cys Thr Arg Thr Thr Leu Ile Ser Val Tyr Phe Asp Tyr Trp Gly Gln
1               5                   10                  15

Gly

<210> SEQ ID NO 102
```

```
<211> LENGTH: 17
<212> TYPE: PRT
<213> ORGANISM: Homo sapiens

<400> SEQUENCE: 102

Cys Ala Thr Tyr Arg Ser Tyr Val Thr Pro Leu Asp Tyr Trp Gly Gln
1               5                   10                  15

Gly

<210> SEQ ID NO 103
<211> LENGTH: 17
<212> TYPE: PRT
<213> ORGANISM: Homo sapiens

<400> SEQUENCE: 103

Cys Ala Lys Phe Arg Gln Tyr Ser Gly Gly Phe Asp Tyr Trp Gly Gln
1               5                   10                  15

Gly

<210> SEQ ID NO 104
<211> LENGTH: 17
<212> TYPE: PRT
<213> ORGANISM: Homo sapiens

<400> SEQUENCE: 104

Cys Ala Arg Leu Gly Asn Phe Tyr Tyr Gly Met Asp Val Trp Gly Gln
1               5                   10                  15

Gly

<210> SEQ ID NO 105
<211> LENGTH: 17
<212> TYPE: PRT
<213> ORGANISM: Homo sapiens

<400> SEQUENCE: 105

Cys Ala Arg Gly Leu Trp Gly Tyr Tyr Ala Leu Asp Tyr Trp Gly Gln
1               5                   10                  15

Gly

<210> SEQ ID NO 106
<211> LENGTH: 17
<212> TYPE: PRT
<213> ORGANISM: Homo sapiens

<400> SEQUENCE: 106

Cys Ala Arg Gln Leu Trp Gly Tyr Tyr Ala Leu Asp Ile Trp Gly Gln
1               5                   10                  15

Gly

<210> SEQ ID NO 107
<211> LENGTH: 17
<212> TYPE: PRT
<213> ORGANISM: Homo sapiens

<400> SEQUENCE: 107

Cys Ala Arg Leu Arg Asn Trp Asp Glu Pro Met Asp Tyr Trp Gly Gln
1               5                   10                  15

Gly

<210> SEQ ID NO 108
<211> LENGTH: 17
```

<212> TYPE: PRT
<213> ORGANISM: Homo sapiens

<400> SEQUENCE: 108

Cys Ala Arg Arg Asp Gly Asn Tyr Gly Trp Phe Ala Tyr Trp Gly Gln
1               5                   10                  15

Gly

<210> SEQ ID NO 109
<211> LENGTH: 17
<212> TYPE: PRT
<213> ORGANISM: Homo sapiens

<400> SEQUENCE: 109

Cys Ala Arg Arg Gly Asp Ser Met Ile Thr Thr Asp Tyr Trp Gly Gln
1               5                   10                  15

Gly

<210> SEQ ID NO 110
<211> LENGTH: 17
<212> TYPE: PRT
<213> ORGANISM: Homo sapiens

<400> SEQUENCE: 110

Cys Val Arg Tyr Tyr Gly Tyr Asp Glu Ala Met Asp Tyr Trp Gly Gln
1               5                   10                  15

Gly

<210> SEQ ID NO 111
<211> LENGTH: 18
<212> TYPE: PRT
<213> ORGANISM: Homo sapiens

<400> SEQUENCE: 111

Cys Val Lys Gly Gly Tyr Tyr Gly His Trp Tyr Phe Asp Val Trp Gly
1               5                   10                  15

Ala Gly

<210> SEQ ID NO 112
<211> LENGTH: 18
<212> TYPE: PRT
<213> ORGANISM: Homo sapiens

<400> SEQUENCE: 112

Cys Ala Arg Ala Leu Thr Tyr Tyr Asp Tyr Glu Phe Ala Tyr Trp Gly
1               5                   10                  15

Gln Gly

<210> SEQ ID NO 113
<211> LENGTH: 18
<212> TYPE: PRT
<213> ORGANISM: Homo sapiens

<400> SEQUENCE: 113

Cys Ala Arg Gly Gly Arg Asp Phe Gly Asp Ser Phe Asp Tyr Trp Gly
1               5                   10                  15

Gln Gly

<210> SEQ ID NO 114
<211> LENGTH: 18
<212> TYPE: PRT

-continued

<213> ORGANISM: Homo sapiens

<400> SEQUENCE: 114

Cys Ala Ser Thr Leu Gly Leu Val Leu Asp Ala Met Asp Tyr Trp Gly
1               5                   10                  15

Gln Gly

<210> SEQ ID NO 115
<211> LENGTH: 18
<212> TYPE: PRT
<213> ORGANISM: Homo sapiens

<400> SEQUENCE: 115

Cys Ala Arg Leu Ser Pro Gly Gly Tyr Tyr Val Met Asp Ala Trp Gly
1               5                   10                  15

Gln Gly

<210> SEQ ID NO 116
<211> LENGTH: 18
<212> TYPE: PRT
<213> ORGANISM: Homo sapiens

<400> SEQUENCE: 116

Cys Ala Arg Asp Gly Gly Ile Ala Ala Pro Gly Pro Asp Tyr Trp Gly
1               5                   10                  15

Gln Gly

<210> SEQ ID NO 117
<211> LENGTH: 18
<212> TYPE: PRT
<213> ORGANISM: Homo sapiens

<400> SEQUENCE: 117

Cys Ala Ile Val Gly Ser Phe Ser Pro Leu Thr Leu Gly Leu Trp Gly
1               5                   10                  15

Gln Gly

<210> SEQ ID NO 118
<211> LENGTH: 18
<212> TYPE: PRT
<213> ORGANISM: Homo sapiens

<400> SEQUENCE: 118

Cys Ser Arg Ser Arg Gly Lys Asn Glu Ala Trp Phe Ala Tyr Trp Gly
1               5                   10                  15

Gln Gly

<210> SEQ ID NO 119
<211> LENGTH: 18
<212> TYPE: PRT
<213> ORGANISM: Homo sapiens

<400> SEQUENCE: 119

Cys Ala Arg Ser Thr Met Ile Thr Asn Tyr Val Met Asp Tyr Trp Gly
1               5                   10                  15

Gln Gly

<210> SEQ ID NO 120
<211> LENGTH: 18
<212> TYPE: PRT
<213> ORGANISM: Homo sapiens

```
<400> SEQUENCE: 120

Cys Ala Arg Val Ser Ile Phe Gly Val Gly Thr Phe Asp Tyr Trp Gly
1               5                   10                  15

Gln Gly

<210> SEQ ID NO 121
<211> LENGTH: 18
<212> TYPE: PRT
<213> ORGANISM: Homo sapiens

<400> SEQUENCE: 121

Cys Ala Arg Gly Gly Gly Ser Ile Tyr Tyr Ala Met Asp Tyr Trp Gly
1               5                   10                  15

Gln Gly

<210> SEQ ID NO 122
<211> LENGTH: 18
<212> TYPE: PRT
<213> ORGANISM: Homo sapiens

<400> SEQUENCE: 122

Cys Ser Arg Trp Gly Gly Asp Gly Phe Tyr Ala Met Asp Tyr Trp Gly
1               5                   10                  15

Gln Gly

<210> SEQ ID NO 123
<211> LENGTH: 18
<212> TYPE: PRT
<213> ORGANISM: Homo sapiens

<400> SEQUENCE: 123

Cys Ala Arg Ala Asn Asp Gly Val Tyr Tyr Ala Met Asp Tyr Trp Gly
1               5                   10                  15

Gln Gly

<210> SEQ ID NO 124
<211> LENGTH: 19
<212> TYPE: PRT
<213> ORGANISM: Homo sapiens

<400> SEQUENCE: 124

Cys Gly Arg Glu Gly Ile Arg Tyr Tyr Gly Leu Leu Gly Asp Tyr Trp
1               5                   10                  15

Gly Gln Gly

<210> SEQ ID NO 125
<211> LENGTH: 19
<212> TYPE: PRT
<213> ORGANISM: Homo sapiens

<400> SEQUENCE: 125

Cys Ala Arg Asp Asp Ser Ser Asp Trp Asp Ala Lys Phe Asn Leu Trp
1               5                   10                  15

Gly Gln Gly

<210> SEQ ID NO 126
<211> LENGTH: 19
<212> TYPE: PRT
<213> ORGANISM: Homo sapiens
```

-continued

<400> SEQUENCE: 126

Cys Ala Arg Asp Arg Gly Gly Asp Tyr Tyr Tyr Gly Met Asp Val Trp
1               5                   10                  15

Gly Gln Gly

<210> SEQ ID NO 127
<211> LENGTH: 19
<212> TYPE: PRT
<213> ORGANISM: Homo sapiens

<400> SEQUENCE: 127

Cys Ala Lys Ile Leu Gly Ala Gly Arg Gly Trp Tyr Phe Asp Leu Trp
1               5                   10                  15

Gly Lys Gly

<210> SEQ ID NO 128
<211> LENGTH: 19
<212> TYPE: PRT
<213> ORGANISM: Homo sapiens

<400> SEQUENCE: 128

Cys Ala Arg Glu Ser Arg Val Ser Phe Glu Ala Met Asp Tyr Trp
1               5                   10                  15

Gly Gln Gly

<210> SEQ ID NO 129
<211> LENGTH: 19
<212> TYPE: PRT
<213> ORGANISM: Homo sapiens

<400> SEQUENCE: 129

Cys Ala Arg Glu Pro Glu Lys Phe Asp Ser Asp Ser Asp Val Trp
1               5                   10                  15

Gly Arg Gly

<210> SEQ ID NO 130
<211> LENGTH: 19
<212> TYPE: PRT
<213> ORGANISM: Homo sapiens

<400> SEQUENCE: 130

Cys Ala Arg Ser Thr Tyr Val Gly Gly Asp Trp Gln Phe Asp Val Trp
1               5                   10                  15

Gly Lys Gly

<210> SEQ ID NO 131
<211> LENGTH: 19
<212> TYPE: PRT
<213> ORGANISM: Homo sapiens

<400> SEQUENCE: 131

Cys Ala Arg Gly Ser His Tyr Phe Gly His Trp His Phe Ala Val Trp
1               5                   10                  15

Gly Gln Gly

<210> SEQ ID NO 132
<211> LENGTH: 19
<212> TYPE: PRT
<213> ORGANISM: Homo sapiens

<400> SEQUENCE: 132

Cys Ala Arg Ile Arg Val Gly Pro Ser Gly Gly Ala Phe Asp Tyr Trp
1               5                   10                  15

Gly Gln Gly

<210> SEQ ID NO 133
<211> LENGTH: 19
<212> TYPE: PRT
<213> ORGANISM: Homo sapiens

<400> SEQUENCE: 133

Cys Ala Arg Glu Asp Tyr Tyr Asp Asn Ser Tyr Tyr Phe Asp Tyr Trp
1               5                   10                  15

Gly Gln Gly

<210> SEQ ID NO 134
<211> LENGTH: 19
<212> TYPE: PRT
<213> ORGANISM: Homo sapiens

<400> SEQUENCE: 134

Cys Ala Arg Gly Gly Tyr Asp Phe Trp Ser Gly Tyr Phe Asp Tyr Trp
1               5                   10                  15

Gly Gln Gly

<210> SEQ ID NO 135
<211> LENGTH: 19
<212> TYPE: PRT
<213> ORGANISM: Homo sapiens

<400> SEQUENCE: 135

Cys Ala Arg Ser Thr Tyr Tyr Gly Gly Asp Trp Tyr Phe Asn Val Trp
1               5                   10                  15

Gly Ala Gly

<210> SEQ ID NO 136
<211> LENGTH: 19
<212> TYPE: PRT
<213> ORGANISM: Homo sapiens

<400> SEQUENCE: 136

Cys Ala Arg Gly Gly Tyr Asp Gly Trp Asp Tyr Ala Ile Asp Tyr Trp
1               5                   10                  15

Gly Gln Gly

<210> SEQ ID NO 137
<211> LENGTH: 19
<212> TYPE: PRT
<213> ORGANISM: Homo sapiens

<400> SEQUENCE: 137

Cys Ala Arg Ser Thr Tyr Tyr Gly Gly Asp Trp Tyr Phe Asp Val Trp
1               5                   10                  15

Gly Gln Gly

<210> SEQ ID NO 138
<211> LENGTH: 20
<212> TYPE: PRT
<213> ORGANISM: Homo sapiens

<400> SEQUENCE: 138

Cys Ala Lys Asp Lys Ile Leu Trp Phe Gly Glu Pro Val Phe Asp Tyr
1               5                   10                  15

Trp Gly Gln Gly
            20

<210> SEQ ID NO 139
<211> LENGTH: 20
<212> TYPE: PRT
<213> ORGANISM: Homo sapiens

<400> SEQUENCE: 139

Cys Ala Arg Ala Asp Tyr Tyr Gly Ser Asp Tyr Val Lys Phe Asp Tyr
1               5                   10                  15

Trp Gly Gln Gly
            20

<210> SEQ ID NO 140
<211> LENGTH: 20
<212> TYPE: PRT
<213> ORGANISM: Homo sapiens

<400> SEQUENCE: 140

Cys Ala Arg Glu Lys Asp Asn Tyr Ala Thr Gly Ala Trp Phe Ala Tyr
1               5                   10                  15

Trp Gly Gln Gly
            20

<210> SEQ ID NO 141
<211> LENGTH: 20
<212> TYPE: PRT
<213> ORGANISM: Homo sapiens

<400> SEQUENCE: 141

Cys Ala Arg Glu Lys Asp Asn Tyr Ala Thr Gly Ala Trp Phe Ala Tyr
1               5                   10                  15

Trp Gly Gln Gly
            20

<210> SEQ ID NO 142
<211> LENGTH: 20
<212> TYPE: PRT
<213> ORGANISM: Homo sapiens

<400> SEQUENCE: 142

Cys Thr Arg Asp Gly Tyr Ser Ser Gly Arg His Tyr Gly Met Asp Val
1               5                   10                  15

Trp Gly Gln Gly
            20

<210> SEQ ID NO 143
<211> LENGTH: 20
<212> TYPE: PRT
<213> ORGANISM: Homo sapiens

<400> SEQUENCE: 143

Cys Ala Arg Asp Gly Asp Tyr Gly Ser Ser Tyr Gly Ala Met Asp Tyr
1               5                   10                  15

Trp Gly Gln Gly
            20

<210> SEQ ID NO 144
<211> LENGTH: 20

```
<212> TYPE: PRT
<213> ORGANISM: Homo sapiens

<400> SEQUENCE: 144

Cys Ala Arg Val Val Tyr Tyr Ser Asn Ser Tyr Trp Tyr Phe Asp Val
1               5                   10                  15

Trp Gly Thr Gly
            20

<210> SEQ ID NO 145
<211> LENGTH: 20
<212> TYPE: PRT
<213> ORGANISM: Homo sapiens

<400> SEQUENCE: 145

Cys Ala Arg Asp Ser Ser Ser Trp Ala Arg Trp Phe Phe Asp Leu
1               5                   10                  15

Trp Gly Arg Gly
            20

<210> SEQ ID NO 146
<211> LENGTH: 20
<212> TYPE: PRT
<213> ORGANISM: Homo sapiens

<400> SEQUENCE: 146

Cys Ser Ala Ser Tyr Tyr Arg Tyr Asp Val Gly Ala Trp Phe Ala Tyr
1               5                   10                  15

Trp Gly Gln Gly
            20

<210> SEQ ID NO 147
<211> LENGTH: 20
<212> TYPE: PRT
<213> ORGANISM: Homo sapiens

<400> SEQUENCE: 147

Cys Ala Arg Asp Tyr Gly Pro Gly Asn Tyr Asp Trp Tyr Phe Asp Leu
1               5                   10                  15

Trp Gly Arg Gly
            20

<210> SEQ ID NO 148
<211> LENGTH: 21
<212> TYPE: PRT
<213> ORGANISM: Homo sapiens

<400> SEQUENCE: 148

Cys Ala Lys Tyr Pro His Tyr Tyr Gly Ser Ser His Trp Tyr Phe Asp
1               5                   10                  15

Val Trp Gly Gln Gly
            20

<210> SEQ ID NO 149
<211> LENGTH: 21
<212> TYPE: PRT
<213> ORGANISM: Homo sapiens

<400> SEQUENCE: 149

Cys Ala Arg Asp His Asp Phe Arg Ser Gly Tyr Glu Gly Trp Phe Asp
1               5                   10                  15

Pro Trp Gly Gln Gly
```

```
<210> SEQ ID NO 150
<211> LENGTH: 21
<212> TYPE: PRT
<213> ORGANISM: Homo sapiens

<400> SEQUENCE: 150

Cys Ala Arg Val Tyr Ser Ser Gly Trp His Val Ser Asp Tyr Phe Asp
1               5                   10                  15

Tyr Trp Gly Gln Gly
            20

<210> SEQ ID NO 151
<211> LENGTH: 21
<212> TYPE: PRT
<213> ORGANISM: Homo sapiens

<400> SEQUENCE: 151

Cys Thr Arg Asn Gly Asp Tyr Tyr Val Ser Ser Gly Asp Ala Met Asp
1               5                   10                  15

Tyr Trp Gly Gln Gly
            20

<210> SEQ ID NO 152
<211> LENGTH: 21
<212> TYPE: PRT
<213> ORGANISM: Homo sapiens

<400> SEQUENCE: 152

Cys Ala Arg Phe Ser His Phe Ser Gly Ser Asn Tyr Asp Tyr Phe Asp
1               5                   10                  15

Tyr Trp Gly Gln Gly
            20

<210> SEQ ID NO 153
<211> LENGTH: 21
<212> TYPE: PRT
<213> ORGANISM: Homo sapiens

<400> SEQUENCE: 153

Cys Ala Arg Ile Pro Ser Gly Ser Tyr Tyr Tyr Asp Tyr Asp Met Asp
1               5                   10                  15

Val Trp Gly Gln Gly
            20

<210> SEQ ID NO 154
<211> LENGTH: 21
<212> TYPE: PRT
<213> ORGANISM: Homo sapiens

<400> SEQUENCE: 154

Cys Ala Arg His Ser Gly Tyr Gly Thr His Trp Gly Val Leu Phe Ala
1               5                   10                  15

Tyr Trp Gly Gln Gly
            20

<210> SEQ ID NO 155
<211> LENGTH: 21
<212> TYPE: PRT
<213> ORGANISM: Homo sapiens

<400> SEQUENCE: 155
```

Cys Ala Arg Glu Gly Val Tyr His Asp Tyr Asp Asp Tyr Ala Met Asp
1               5                   10                  15

Tyr Trp Gly Gln Gly
            20

<210> SEQ ID NO 156
<211> LENGTH: 21
<212> TYPE: PRT
<213> ORGANISM: Homo sapiens

<400> SEQUENCE: 156

Cys Ala Arg Leu Gly Tyr Asp Asp Ile Tyr Asp Asp Trp Tyr Phe Asp
1               5                   10                  15

Val Trp Gly Gln Gly
            20

<210> SEQ ID NO 157
<211> LENGTH: 21
<212> TYPE: PRT
<213> ORGANISM: Homo sapiens

<400> SEQUENCE: 157

Cys Ala Arg Gly Glu Leu Pro Tyr Tyr Arg Met Ser Lys Val Met Asp
1               5                   10                  15

Val Trp Gly Gln Gly
            20

<210> SEQ ID NO 158
<211> LENGTH: 22
<212> TYPE: PRT
<213> ORGANISM: Homo sapiens

<400> SEQUENCE: 158

Cys Ala Arg Arg Glu Thr Thr Thr Val Gly Arg Tyr Tyr Tyr Ala Met
1               5                   10                  15

Asp Tyr Trp Gly Gln Gly
            20

<210> SEQ ID NO 159
<211> LENGTH: 22
<212> TYPE: PRT
<213> ORGANISM: Homo sapiens

<400> SEQUENCE: 159

Cys Ala Arg Gly Tyr Tyr Asp Ile Leu Thr Gly Tyr Tyr Tyr Tyr Phe
1               5                   10                  15

Asp Tyr Trp Gly Gln Gly
            20

<210> SEQ ID NO 160
<211> LENGTH: 23
<212> TYPE: PRT
<213> ORGANISM: Homo sapiens

<400> SEQUENCE: 160

Cys Ala Lys Asp Leu Gly Trp Ser Asp Ser Tyr Tyr Tyr Tyr Tyr Gly
1               5                   10                  15

Met Asp Val Trp Gly Gln Gly
            20

<210> SEQ ID NO 161

```
<211> LENGTH: 23
<212> TYPE: PRT
<213> ORGANISM: Homo sapiens

<400> SEQUENCE: 161

Cys Ala Arg Gly Arg Tyr Ser Gly Ser Gly Tyr Tyr Asn Asp Trp
1               5                   10                  15

Phe Asp Pro Trp Gly Gln Gly
            20

<210> SEQ ID NO 162
<211> LENGTH: 24
<212> TYPE: PRT
<213> ORGANISM: Homo sapiens

<400> SEQUENCE: 162

Cys Ala Arg Gly Lys Gly Asn Thr His Lys Pro Tyr Gly Tyr Val Arg
1               5                   10                  15

Tyr Phe Asp Val Trp Gly Gln Gly
            20

<210> SEQ ID NO 163
<211> LENGTH: 24
<212> TYPE: PRT
<213> ORGANISM: Homo sapiens

<400> SEQUENCE: 163

Cys Ala Arg Asp His Tyr Gly Ser Gly Val His His Tyr Phe Tyr Tyr
1               5                   10                  15

Gly Leu Asp Val Trp Gly Gln Gly
            20

<210> SEQ ID NO 164
<211> LENGTH: 24
<212> TYPE: PRT
<213> ORGANISM: Homo sapiens

<400> SEQUENCE: 164

Cys Ala Arg Gln Ser Thr Tyr Tyr Tyr Gly Ser Gly Asn Tyr Tyr Gly
1               5                   10                  15

Trp Phe Asp Arg Trp Asp Gln Gly
            20

<210> SEQ ID NO 165
<211> LENGTH: 24
<212> TYPE: PRT
<213> ORGANISM: Homo sapiens

<400> SEQUENCE: 165

Cys Ala Arg Pro Val Arg Ser Arg Trp Leu Gln Leu Gly Leu Glu Asp
1               5                   10                  15

Ala Phe His Ile Trp Gly Gln Gly
            20

<210> SEQ ID NO 166
<211> LENGTH: 25
<212> TYPE: PRT
<213> ORGANISM: Homo sapiens

<400> SEQUENCE: 166

Cys Ala Arg Glu Asn Leu Asp Asn Ser Gly Tyr Thr Tyr Tyr Phe Ser
1               5                   10                  15
```

```
Gly Trp Phe Asp Pro Trp Gly Gln Gly
            20                  25

<210> SEQ ID NO 167
<211> LENGTH: 25
<212> TYPE: PRT
<213> ORGANISM: Homo sapiens

<400> SEQUENCE: 167

Cys Val Arg Asp Tyr Tyr Asp Ile Leu Thr Tyr Asp Tyr Ile His Tyr
1               5                   10                  15

Trp Tyr Phe Asp Leu Trp Gly Arg Gly
            20                  25

<210> SEQ ID NO 168
<211> LENGTH: 26
<212> TYPE: PRT
<213> ORGANISM: Homo sapiens

<400> SEQUENCE: 168

Cys Ala Ala Ala Gly Val Arg Ala Glu Asp Gly Val Arg Arg Thr Leu
1               5                   10                  15

Pro Ser Glu Tyr Thr Phe Trp Gly Gln Gly
            20                  25
```